(12) United States Patent
Fischer et al.

(10) Patent No.: US 6,849,744 B2
(45) Date of Patent: Feb. 1, 2005

(54) α-PHENYL-β-KETO SULFONES

(75) Inventors: Reiner Fischer, Monheim (DE); Oliver Kretschik, Köln (DE); Thomas Schenke, Bergisch Gladbach (DE); Ralf-Ingo Schenkel, Düsseldorf (DE); Jürgen Wiedemann, Leverkusen (DE); Christoph Erdelen, Leverkusen (DE); Peter Lösel, Leverkusen (DE); Mark Wilhelm Drewes, Langenfeld (DE); Dieter Feucht, Monheim (DE); Wolfram Andersch, Bergisch Gladbach (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/461,055

(22) Filed: Jun. 13, 2003

(65) Prior Publication Data

US 2004/0063669 A1 Apr. 1, 2004

Related U.S. Application Data

(62) Division of application No. 09/979,734, filed as application No. PCT/EP00/04415 on May 16, 2000, now Pat. No. 6,670,385.

(30) Foreign Application Priority Data

May 28, 1999 (DE) .......................... 199-24-668

(51) Int. Cl.⁷ ........................ C07D 327/04; A01N 31/00
(52) U.S. Cl. ......................................... 549/40; 504/289
(58) Field of Search ............................ 549/40; 504/289

(56) References Cited

U.S. PATENT DOCUMENTS

| | | | |
|---|---|---|---|
| 3,463,774 A | 8/1969 | Wenner et al. | 260/239.3 |
| 3,558,640 A | 1/1971 | Shen et al. | 260/294.8 |
| 3,725,361 A | 4/1973 | Boustany et al. | 260/79.5 B |
| 3,984,336 A | 10/1976 | Cier et al. | 252/47.5 |
| 4,285,858 A | 8/1981 | Cort et al. | 260/112.5 R |
| 4,639,447 A | 1/1987 | Roeser et al. | 514/222 |
| 4,744,812 A | 5/1988 | Parg et al. | 71/88 |
| 4,831,179 A | 5/1989 | Pomidor | 558/390 |
| 4,885,027 A | 12/1989 | Pomidor | 71/103 |

FOREIGN PATENT DOCUMENTS

| | | |
|---|---|---|
| DE | 24 317 34 | 1/1976 |
| EP | 342 440 | 11/1989 |
| EP | 447 891 | 9/1991 |
| EP | 737 682 | 10/1996 |
| GB | 1 077 272 | 7/1967 |
| WO | 93/13664 | 7/1993 |
| WO | 94/29268 | 12/1994 |

OTHER PUBLICATIONS

Patent Abstracts of Japan, vol. 2000, No. 02, Feb. 29, 2000 & JP 11 322731 A (Otsuka Chem Co Ltd), Nov. 24, 1999 Zusammenfassung.

H.-D. Stachel et al.: Archiv Der Pharmazie, Bd. 318, 1985, Seiten 304–11, XP000925897, in der Anmeldung erwähnt Seite 305, Formeln 3, 4, 5, 6; Seite 506, Tabelle 1, Verbindungen 3d, 3e, 3f, 4c, 4e, 5d, 5e, 5f, 6c, 6d, 6e.

Marco J L et al: "New and Unexpected Developments of the Carbanion–mediated Sulfonate (Sulfonamide) Intramolecular Cyclization Reaction (CSIC Reaction)" Tetrahedron Letters, NL, Elsevier Science Publishers, Amsterdam, Bd. 39, Nr. 23, Jun. 4, 1998, Seiten 4123–4124, XP004118827 ISSN: 0040–4039 in der Anmeldung erwänt das ganze Dokument.

Ingate S T et al: "Studies into the Synthesis of Derivatives of 4–Amino–2, 3–Dihydroisothiazole 1, 1–Dioxides and 4–Amino–1, 2–Oxathiole, 2, 2–Dioxides: The Search for linked pi–System Containing Analogues as Potential Inhibitors of HIV–1 Reverse Transcriptase" Tetrahedron, NL, Elsevier Science Publishers, Amsterdam, Bd. 53, Nr. 52, Dec. 29, 1997, Seiten 17795–17814, XP004126746, ISSN: 0040–4020, in der Anmeldung erwähnt Schemata 1, 2, 3, 4.

J. R. Beck: Journal of Heterocyclic Chemistry, Bd. 15, 1978, Seiten 513–4, XP000938993 in der Anmeldung erwähnt Seite 513, Linke Spalte, Verbindungen 1a, 1b, 1c, 3a, 3b; Seite 514, Herstellungsvoschriften für Verbindungen 3a und 3b.

J. G. Lombardino et al.: Journal of Medicinal Chemistry, Bd. 13, 1970, Seiten 206–10, XP000938994, in der Anmeldung erwä hnt Seite 207, linke Spalte, Reaktionsschema.

J. Am. Chem. Soc., 58, (month unavailable) 1936, pp. 1348–1352, "A New Method for the Preparation of Alkyl Sulfonyl Chlorides" by T. B. Johnson and J. M. Sprague.

(List continued on next page.)

*Primary Examiner*—Joseph K. McKane
*Assistant Examiner*—Rebecca Anderson
(74) *Attorney, Agent, or Firm*—Richard E.L. Henderson

(57) ABSTRACT

The present invention relates to novel aryl-substituted $S(O)_m$ cycles of the formula (I):

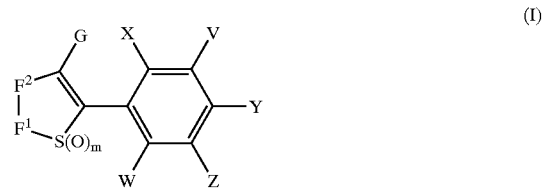

in which $F^1$, $F^2$, G, V, W, X, Y, Z and m are each as defined in the description, to processes for their preparation and to their use in agriculture, for example as crop protection agents (fungicides, herbicides and insecticides).

5 Claims, No Drawings

OTHER PUBLICATIONS

Phosphorus, Sulfur, and Silicon, (month unavailable) 1991, vol. 59, pp. 149–152, "Cyclization of Selected Benzyl Sulfone Derivatives Under Phase Transfer Catalytic Conditions" by N. F. El–Zohhry, A. M. El–Khawaga and Aboel–Magd A. Abel–Wahab.

Chem. Ind., London, Nov. 9, 1968, p. 1568, "Use of molecular sieves in the methyl esterification of carboxylic acids" by H. R. Harrison, W. M. Haynes, P. Arthur and E. J. Eisenbraun.

Organikum, VEB, Deutscher Verlag der Wissenschaften, Berlin, (month unavailable) 1977, pp. 505–507, "Reaktionen von Carbonsäuren und Carbonsäurenderivaten mit Basen".

J. Chem. Soc., (month unavailable) 1960, pp. 3063–3069, "Reactions of Some Arenesulphonyl Chlorides" by W. V. Farrar.

Helv. Chim. Acta., 14, (month unavailable) 1931, pp. 541–570, "Über o, ó—Dicyan–stilben" by von Paul Ruggli.

Ann. Chim., (month unavailable) 1970, t. 5, pp. 23–38, "Addition Des Réactifs Nucléophiles Sur La Triple Liaison Nitrille II.—Addition Des Alcools, Des Composés Azotés, des Organométalliques; Condensation de Plusieurs Molécules De Nitriles" P. L. Campagnon et M. Miocque.

Ann. Chim., (month unavailable) 1970, t. 5, pp. 11–22, "Addition Des Réactifs Nucléophiles Sur La L'Hydrogéne Sélénié" by P. L. Campagnon et M. Miocque.

J. Chem. Soc., (month unavailable) 1961, pp. 4372–4379, "Amino–acids of the Cyclohexane Series. Part I." by L. Munday.

Can. J. Chem., 53, (month unavailable) 1975, pp. 3339–3350, "Stereochemistry of the Bucherer–Bergs and Strecker Reactions of 4–tert–Butylcyclohexanone" by J. T. Edward and C. Jitrangsri.

Chem. Ind., 37, Oct. 1985, pp. 730–732, "Schiffsfarben—eine Spezialität der seenahen Lackindustrie" by H. R. Ungerer.

α-PHENYL-β-KETO SULFONES

This application is a division of application Ser. No. 09/979,734 filed on Nov. 26, 2001 now U.S. Pat. No. 6,670,385, which is the National Stage of International Application No. PCT/EP00/04415, filed May 16, 2000, which is entitled to the right of priority of German Patent Application No. 199 24 668.8, filed May 28, 1999.

The present invention relates to novel aryl-substituted $S(O)_m$ cycles (α-phenyl-β-keto sulphones), to a plurality of processes for their preparation and to their use in agriculture, for example as crop protection agents (for example as fungicides, herbicides and insecticides).

4-Amino-5-phenyl-3-ethyl-2-methyl-2,3-dihydroisothiazole 1,1-dioxide (J. L. Marco et al., Tetrahedron Letters 39, 4123 (1998)), 4-amino-5-phenyl-3,3-dimethyl-2-benzyl-2,3-dihydroisothiazole 1,1-dioxide and 4-amino-5-phenyl-3,3-dimethyl-2-(3-chloro-benzyl)-2,3-dihydroisothiazole 1,1-dioxide (S. T. Ingate, et al., Tetrahedron 53, 17795 (1997)) are known from the literature. Also known are 2-methyl-5-phenyl-isothiazolidin-4-one 1,1-dioxide, 2,3-dimethyl-5-phenyl-isothiazolidin-4-one 1,1-dioxide and 5-phenyl-2,3,3-trimethyl-isothiazolidin-4one 1,1-dioxide (H.-D. Stachel, G. Drasch, Archiv Pharm. 318, 304 (1985)). Use of these compounds as crop protection agents or pesticides has hitherto not been disclosed.

Furthermore known are 3-phenyl-1,2-oxathiolan-4-one 2,2-dioxide, 5-methyl-3-phenyl-1,2-oxathiolan-4-one 2,2-dioxide, 5,5-dimethyl-3-phenyl-1,2-oxathiolan-4-one 2,2-dioxide (H. D. Stachel, G. Drasch, Archiv Pharm. 318, 304 (1985)), 5-amino-5,5-dimethyl-3-phenyl-1,2-oxathiolane 2,2-dioxide and 4-amino-5-methyl-3-phenyl-5-phenylmethyl-1,2-oxathiolane 2,2-dioxide (S. T. Ingate et al., Tetrahedron 53, 17795 (1997)). Use of these compounds as crop protection agents or pesticides has hitherto not been disclosed.

2-Arylbenzo[b]thiophen-3(2H)-one 1,1-dioxides have been disclosed for use as anti-inflammatory agents and anticoagulants (J. G. Lombardino, E. H. Wiseman, J. Med. Chem., 13, 206 (1970)). Also known is 2-phenyl-3-keto-tetrahydrothiophene 1,1-dioxide (A. Abdel-Wahab et al., Phosphorus, Sulfur and Silicon, 59, 149 (1991)). Furthermore known are 2-phenylbenzo[b]thiophene-3-amine, 2-phenylbenzo[b]-thiophene-3-amine 1-oxide and 2-phenylbenzo[b]thiophene-3-amine 1,1-dioxide (J. R. Beck, J. Heterocyclic Chem. 15, 513 (1978)). Likewise, a use of these compounds as crop protection agents or pesticides has hitherto not been disclosed.

This invention, accordingly, provides aryl-substituted $S(O)_m$ cycles of the general formula (I):

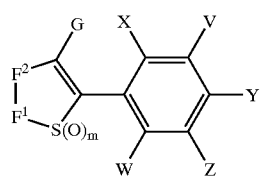

(I)

in which

V, W, X, Y and Z independently of one another each represent hydrogen, halogen, nitro, cyano or a radical from the group consisting of alkyl, alkenyl, alkinyl, alkoxy, $S(O)_n$-alkyl, halogenoalkyl, halogenoalkoxy, in each case optionally substituted aryl, phenylalkyl, aryloxy, phenyl-alkyloxy or aryl-$S(O)_n$—, where two adjacent radicals together with the carbon atoms to which they are attached form an optionally substituted ring which is optionally interrupted by one or more heteroatoms;

with the proviso that at least one radical of the substituents V, W, X, Y or Z has to be different from hydrogen, n represents the numbers 0 to 2, m represents the numbers 1 and 2, $F^1$ and $F^2$ represent one of the groups:

   (1)

   (2)

   (3)

(4)

in which

A represents hydrogen, in each case optionally halogen-substituted alkyl, alkenyl, alkoxyalkyl, polyalkoxyalkyl, alkylthioalkyl, saturated or unsaturated, optionally substituted cycloalkyl in which optionally at least one ring atom is replaced by a heteroatom, or represents in each case optionally halogen-, alkyl-, halogenoalkyl-, alkoxy-, halogenoalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkinyl, alkoxyalkyl, polyalkoxyalkyl, alkyl-thioalkyl, saturated or unsaturated, optionally substituted cycloalkyl in which optionally one or more ring members are replaced by heteroatoms, represents optionally substituted arylalkyl, aryl, hetarylalkyl, hetaryl or CO—$R^{11}$, or A and D together with the atoms to which they are attached represent a saturated or unsaturated cycle which is unsubstituted or substituted in the A,D-moiety and optionally contains at least one (in the case of —$F^1$—$F^2$=(4) further) heteroatom, or A and $Q^1$ together represent alkanediyl or alkenediyl, each of which is optionally substituted by in each case optionally substituted alkyl, hydroxyl, alkoxy, alkylthio, cycloalkyl, benzyloxy or aryl, or represent an optionally substituted alkanedienediyl, with the proviso that B and $Q^2$ together with the carbon atoms to which they are attached represent a double bond and at least one of the substituents W or X does not represent hydrogen, $Q^1$ represents hydrogen, alkyl, alkoxyalkyl, alkylthioalkyl, saturated or unsaturated, optionally substituted cycloalkyl in which optionally one or more ring members are replaced by heteroatoms, or represents optionally substituted phenyl, $Q^2$ represents hydrogen or alkyl, G represents hydroxyl (a) or represents one of the groups:

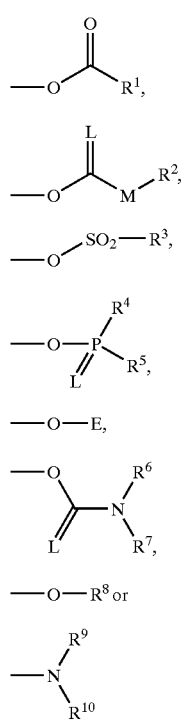

in which
- E represents a metal ion or an ammonium ion,
- L represents oxygen or sulphur,
- M represents oxygen or sulphur,
- $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl in which one or more methylene groups may be replaced by heteroatoms, or represents in each case optionally substituted phenyl, phenylalkyl, hetaryl, phenoxyalkyl or hetaryloxyalkyl,
- $R^2$ represents in each case optionally halogen-substituted alkyl, alkenyl, alkoxyalkyl, polyalkoxyalkyl or represents in each case optionally substituted cycloalkyl, phenyl or benzyl,
- $R^3$, $R^4$ and $R^5$ independently of one another each represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio and
- $R^6$ and $R^7$ independently of one another each represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent an optionally substituted ring which is optionally interrupted by oxygen or sulphur,
- $R^8$ represents in each case optionally halogen-substituted alkyl, alkoxyalkyl, alkenyl, alkenyloxyalkyl, alkinyl, alkinyloxyalkyl, alkylcarbonylalkyl, alkoxycarbonylalkyl or represent optionally substituted cycloalkyl or represent optionally substituted arylalkyl, arylcarbonylalkyl or phenoxyalkyl,
- $R^9$ and $R^{10}$ independently of one another each represent hydrogen, alkyl, alkenyl, alkoxyalkyl, alkylthioalkyl, represent cycloalkyl which is optionally interrupted by heteroatoms, represent in each case optionally substituted phenyl, phenylalkyl, phenoxyalkyl, hetaryl or hetarylalkyl, or
- $R^9$ and $R^{10}$ together with the nitrogen to which they are attached form a 3- to 9-membered ring which is optionally substituted and optionally interrupted by further heteroatoms, or
- $R^{10}$ represents the group CO—$R^{11}$, where
  - $R^{11}$ represents hydrogen, optionally halogen-substituted alkyl, alkenyl, alkoxy, optionally substituted cycloalkyl which may optionally be interrupted by heteroatoms, or represents optionally substituted aryl, arylalkyl, arylalkyloxy or phenoxy, possible substituents being halogen, nitro, cyano, alkyl, alkoxy, halogenoalkyl and halogenoalkoxy.

Depending inter alia on the nature of the substituents, the compounds of the formula (I) can be present as geometric and/or optical isomers or isomer mixtures of different composition which, if appropriate, can be separated in a customary manner. The present invention provides both the pure isomers and the isomer mixtures, their preparation and use and the compositions comprising them. However, hereinbelow, for the sake of simplicity, compounds of the formula (I) are always referred to, although this may mean both the pure compounds and, if appropriate, mixtures having different proportions of isomeric compounds.

Incorporating the meanings (1) to (4) of the group —$F^1$—$F^2$—, the following main structures (I-1) to (I-4) result:

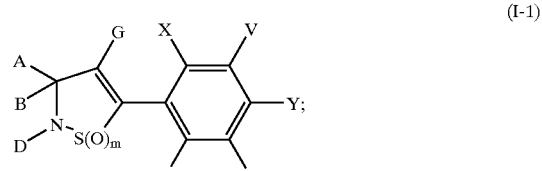
(I-1)

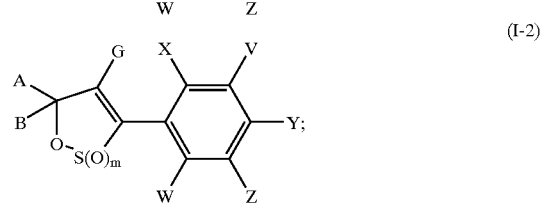
(I-2)

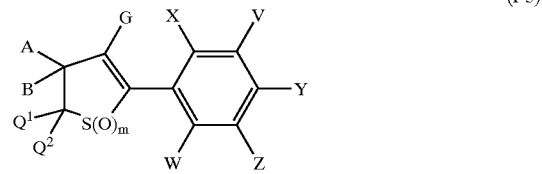
(I-3)

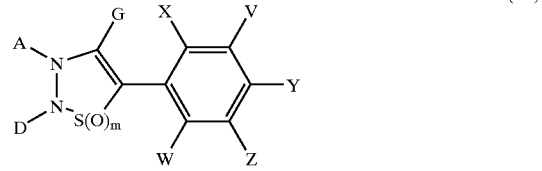
(I-4)

in which
- A, B, D, G, $Q^1$, $Q^2$, V, W, X, Y, Z and m are each as defined above.

Incorporating the different meanings (a), (b), (c), (d), (e), (f), (g), (h) and (i) of the group G, the following main structures (I-1-a) to (I-1-i) result if —F$^1$—F$^2$— represents the group (1):
(I-1-a):
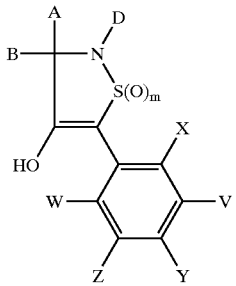
(I-1-b):
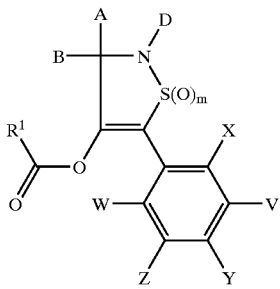
(I-1-c):
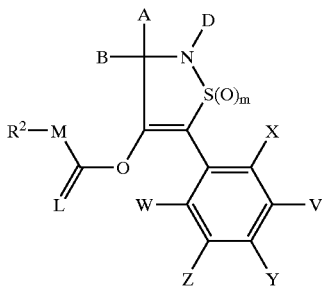
(I-1-d):
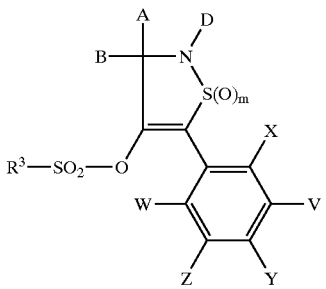
(I-1-e):
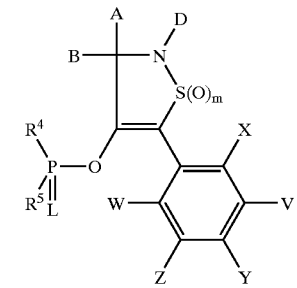
-continued
(I-1-f):
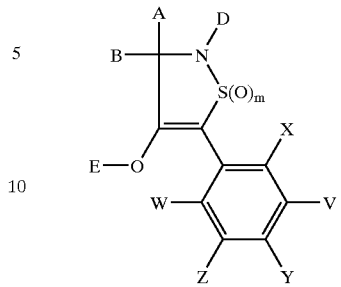
(I-1-g):
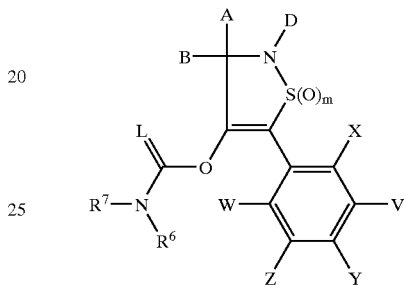
(I-1-h):
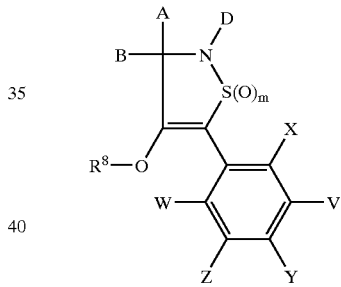
(I-1-i):
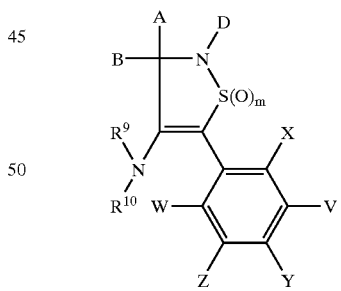
in which
A, B, D, E, L, M, V, W, X, Y, Z, $R^1$, $R^2$, $R^3$, $R^4$, $R^5$, $R^6$, $R^7$, $R^8$, $R^9$, $R^{10}$ and m are each as defined above.
Incorporating the different meanings (a), (b), (c), (d), (e), (f), (g), (h) and (i) of the group G, the following main structures (I-2-a) to (I-2-i) result if —F$^1$—F$^2$— represents the group (2):

(I-2-a):
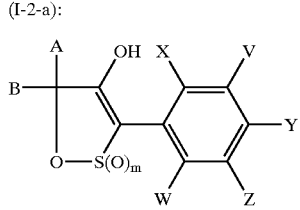
(I-2-b):
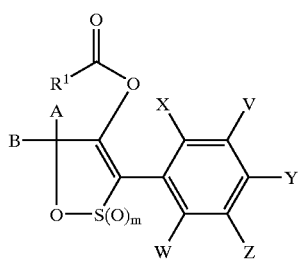
(I-2-c):
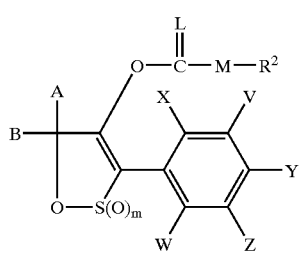
(I-2-d):
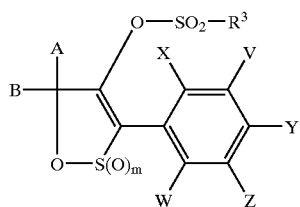
(I-2-e):
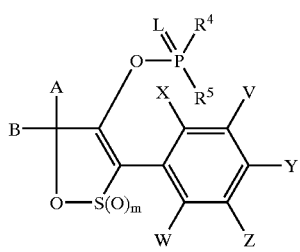
(I-2-f):
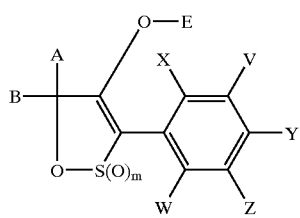
(I-2-g):
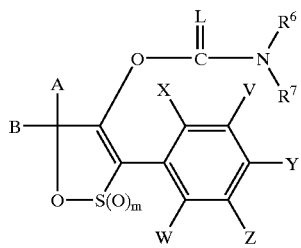
(I-2-h):
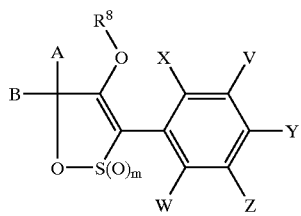
(I-2-i):
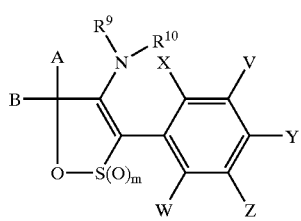
in which
A, B, E, L, M, V, W, X, Z, $R^1$, $R^2$, $R^3$, $R^4$, $R^5$, $R^6$, $R^7$, $R^8$, $R^9$, $R^{10}$ and m are each as defined above.
Incorporating the different meanings (a), (b), (c), (d), (e), (f), (g), (h) and (i) of the group G, the following main structures (I-3-a) to (I-3-i) result if —$F^1$—$F^2$— represents the group (3):
(I-3-a):
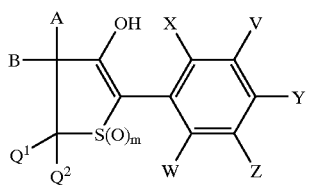
(I-3-b):
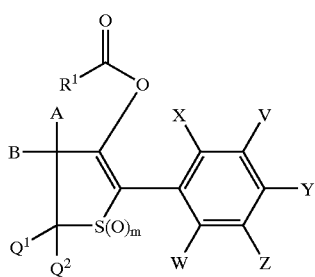

(I-3-c):
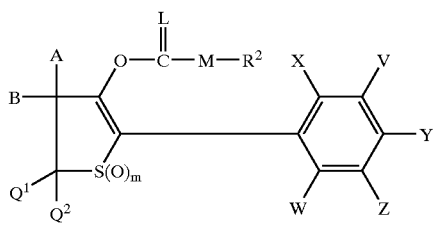
(I-3-d):
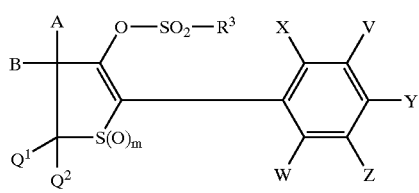
(I-3-e):
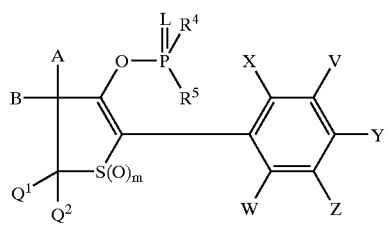
(I-3-f):
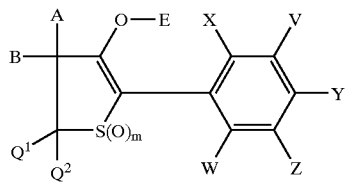
(I-3-g):
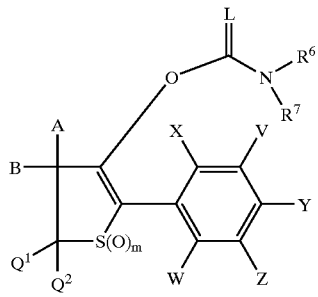
(I-3-h):
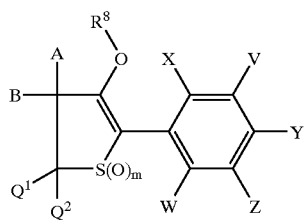
(I-3-i):
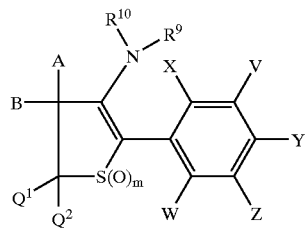
in which
A, B, $Q^1$, $Q^2$, E, L, M, V, W, X, Y, Z, $R^1$, $R^2$, $R^3$, $R^4$, $R^5$, $R^6$, $R^7$, $R^8$, $R^9$, $R^{10}$ and m are each as defined above.
Incorporating the different meanings (a), (b), (c), (d), (e), (f), (g) (h) and (i) of the group G, the following main structures (I-4-a) to (I-4-i) result if —$F^1$—$F^2$— represents the group (4):
(I-4-a):
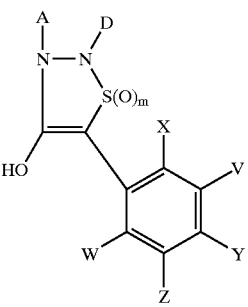
(I-4-b):
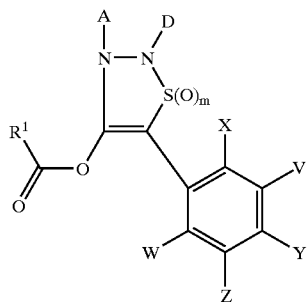
(I-4-c):
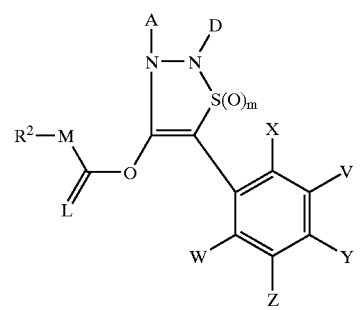

-continued (I-4-d):
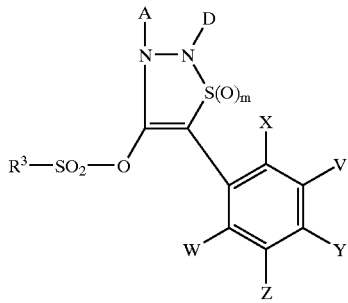

(I-4-e):
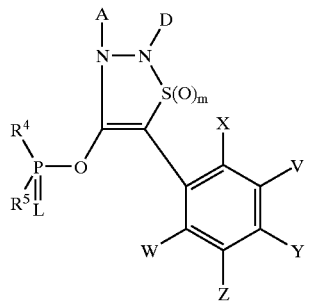

(I-4-f):
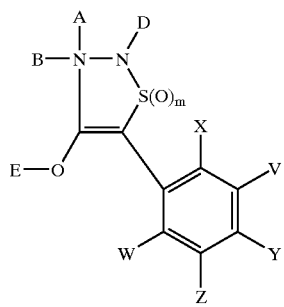

(I-4-g):
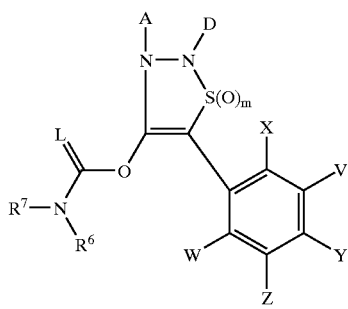

(I-4-h):
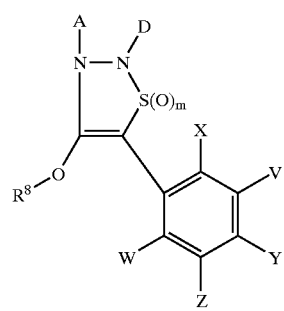

-continued (I-4-i):
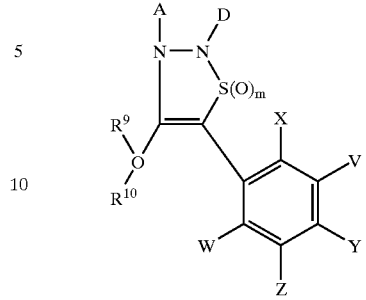

in which

A, D, E, L, M, V, W, X, Y, Z, $R^1$, $R^2$, $R^3$, $R^4$, $R^5$, $R^6$, $R^7$, $R^8$, $R^9$, $R^{10}$ and m are each as defined above.

Furthermore, it has been found that the novel compounds of the formula (I) are obtained by one of the processes described below:

(A) Substituted compounds of the formula (I-1-a):

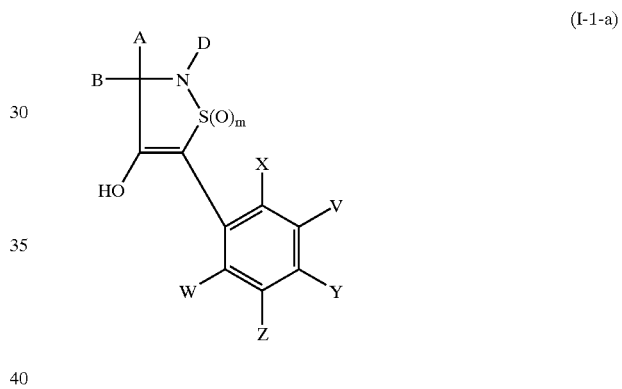

(I-1-a)

in which

A, B, D, V, W, X, Y, Z and m are each as defined above are obtained when amino acid esters of the formula (II):

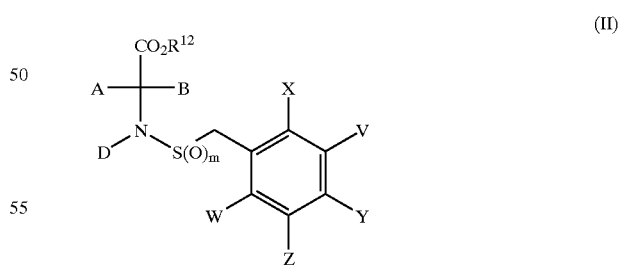

(II)

in which

A, B, D, V, W, X, Y, Z and m are each as defined above and $R^{12}$ represents alkyl (preferably $C_1$–$C_6$-alkyl)

are condensed intramolecularly in the presence of a diluent and in the presence of a base.

(B) Moreover, it has been found that substituted compounds of the formula (I-2-a):

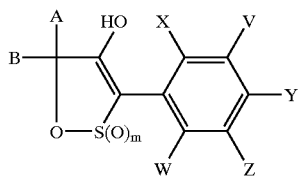
(I-2-a)

in which
A, B, V, W, X, Y, Z and m are each as defined above
are obtained when
carboxylic acid esters of the formula (III):

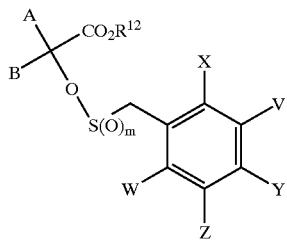
(III)

in which
A, B, V, W, X, Y, Z, $R^{12}$ and m are each as defined above
are condensed intramolecularly in the presence of a diluent and in the presence of a base.

Furthermore, it has been found
(C) that compounds of the formula (I-3-a):

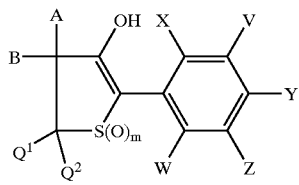
(I-3-a)

in which
A, B, $Q^1$, $Q^2$, V, W, X, Y, Z and m are each as defined above
are obtained when
carboxylic acid esters of the formula (IV):

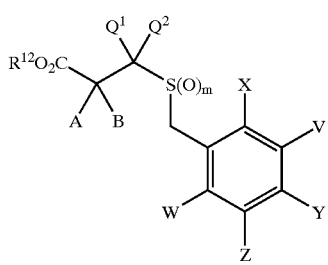
(IV)

in which
A, B, $Q^1$, $Q^2$, V, W, X, Y, Z and m are each as defined above and $R^{12}$ represents alkyl (in particular $C_1$–$C_8$-alkyl)
are cyclized intramolecularly, if appropriate in the presence of a diluent and in the presence of a base.

(D) Furthermore, substituted compounds of the formula (I-4-a):

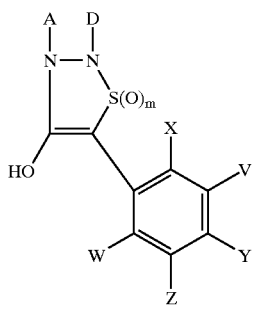
(I-4-a)

in which
A, D, V, W, X, Y, Z and m are each as defined above
are obtained when
hydrazides of the formula (V):

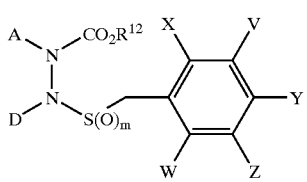
(V)

in which
A, D, V, W, X, Y, Z and m are each as defined above and
$R^{12}$ represents alkyl (in particular $C_1$–$C_6$-alkyl) or optionally substituted phenyl (in particular halogen- or nitro-substituted phenyl)
are cyclized, if appropriate in the presence of a diluent and in the presence of a base.

Moreover, it has been found
(E) that the compounds of the formulae (I-1-b) to (I-4-b) shown above in which A, B, D, $Q^1$, $Q^2$, $R^1$, V, W, X, Y, Z and m are each as defined above are obtained when compounds of the formulae (I-1-a) to (I-4-a) shown above in which A, B, D, $Q^1$, $Q^2$, V, W, X, Y, Z and m are each as defined above are in each case
(α) reacted with acid halides of the formula (VI):

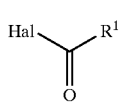
(VI)

in which
$R^1$ is as defined above and
Hal represents halogen (in particular chlorine or bromine)
or
(β) reacted with carboxylic anhydrides of the formula (VII):

$R^1$—CO—O—CO—$R^1$ (VII)

in which
$R^1$ is as defined above,
if appropriate in the presence of a diluent and if appropriate in the presence of an acid binder;

(F) that the compounds of the formulae (I-1-c) to (I-4-c) shown above in which A, B, D, $Q^1$, $Q^2$, $R^2$, M, V, W, X, Y, Z and m are each as defined above and L represents oxygen are obtained when compounds of the formulae (I-1-a) to (I-4-a) shown above in which A, B, D, $Q^1$, $Q^2$, V, W, X, Y, Z and m are each as defined above are in each case reacted with chloroformic esters or chloroformic thioesters of the formula (VIII):

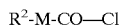

$R^2$-M-CO—Cl        (VIII)

in which $R^2$ and M are each as defined above, if appropriate in the presence of a diluent and if appropriate in the presence of an acid binder;

(G) that compounds of the formulae (I-1-c) to (I-4-c) shown above in which A, B, D, $Q^1$, $Q^2$, $R^2$, M, V, W, X, Y, Z and m are each as defined above and L represents sulphur are obtained when compounds of the formulae (I-1-a) to (I-4-a) shown above in which A, B, D, $Q^1$, $Q^2$, V, W, X, Y, Z and m are each as defined above are in each case reacted with chloromonothioformic esters or chlorodithioformic esters of the formula (IX):

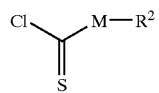

(IX)

in which

M and $R^2$ are each as defined above, if appropriate in the presence of a diluent and if appropriate in the presence of an acid binder, and (H) that compounds of the formulae (I-1-d) to (I-4-d) shown above in which A, B, D, $Q^1$, $Q^2$, $R^3$, V, W, X, Y, Z and m are each as defined above are obtained when compounds of the formulae (I-1-a) to (I-4-a) shown above in which A, B, D, $Q^1$, $Q^2$, V, W, X, Y, Z and m are each as defined above are in each case reacted with sulphonyl chlorides of the formula (X):

$R^3$—$SO_2$—Cl        (X)

in which $R^3$ is as defined above, if appropriate in the presence of a diluent and if appropriate in the presence of an acid binder, (I) that compounds of the formulae (I-1-e) to (I-4-e) shown above in which A, B, D, L, $Q^1$, $Q^2$, $R^4$, $R^5$, V, W, X, Y, Z and m are each as defined above are obtained when compounds of the formulae (I-1-a) to (I-4-a) shown above in which A, B, D, $Q^1$, $Q^2$, V, W, X, Y, Z and m are each as defined above are in each case reacted with phosphorus compounds of the formula (XI):

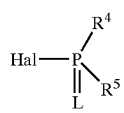

(XI)

in which

L, $R^4$ and $R^5$ are each as defined above and

Hal represents halogen (in particular chlorine or bromine), if appropriate in the presence of a diluent and if appropriate in the presence of an acid binder, (J) that compounds of the formulae (I-1-f) to (I-4-f) shown above in which A, B, D, E, $Q^1$, $Q^2$, V, W, X, Y, Z and m are each as defined above are obtained when compounds of the formulae (I-1-a) to (I-4-a) in which A, B, D, $Q^1$, $Q^2$, V, W, X, Y, Z and m are each as defined above are in each case reacted with metal compounds or amines of the formula (XII) or (XIII):

$Me(OR^{13})_t$        (XII)

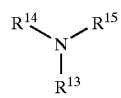

(XIII)

in which

Me represents a mono- or divalent metal (preferably an alkali metal or alkaline earth metal, such as lithium, sodium, potassium, magnesium or calcium), t represents the number 1 or 2 and $R^{13}$, $R^{14}$, $R^{15}$ independently of one another each represent hydrogen or alkyl (preferably $C_1$–$C_8$-alkyl), if appropriate in the presence of a diluent, (K) that compounds of the formulae (I-1-g) to (I-4-g) shown above in which A, B, D, L, $Q^1$, $Q^2$, $R^6$, $R^7$, V, W, X, Y, Z and m are each as defined above are obtained when compounds of the formulae (I-1-a) to (I-4-a) shown above in which A, B, D, $Q^1$, $Q^2$, V, W, X, Y, Z and m are each as defined above are in each case (α) reacted with isocyanates or isothiocyanates of the formula (XIV):

$R^6$—N=C=L        (XIV)

in which $R^6$ and L are each as defined above, if appropriate in the presence of a diluent and if appropriate in the presence of a catalyst, or (β) reacted with carbamoyl chlorides or thiocarbamoyl chlorides of the formula (XV):

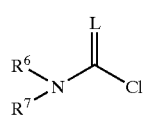

(XV)

in which

L, $R^6$ and $R^7$ are each as defined above, if appropriate in the presence of a diluent and if appropriate in the presence of an acid binder, (L) that compounds of the formulae (I-1-h) to (I-4-h) shown above in which A, B, D, $Q^1$, $Q^2$, $R^8$, V, W, X, Y, Z and m are each as defined above are obtained when compounds of the formulae (I-1-a) to (I-4-a) shown above in which A, B, D, $Q^1$, $Q^2$, V, W, X, Y, Z and m are each as defined above are reacted with compounds of the formula (XVI):

in which
R$^{10}$ is as defined above,
U represents chlorine, bromine, iodine and O—SO$_2$—R$^{16}$ and
R$^{16}$ represents optionally halogen-substituted alkyl (in particular trifluoromethyl) or optionally substituted phenyl (in particular methyl-, chlorine-, bromine- or nitro-substituted phenyl),
if appropriate in the presence of a diluent and if appropriate in the presence of an acid binder, (M) that compounds of the formulae (I-1-i) to (IA4-i) shown above in which A, B, D, Q$^1$, Q$^2$, R$^9$, R$^{10}$, V, W, X, Y, Z and m are each as defined above, where R$^{10}$ does not represent the group CO—R$^{11}$, are obtained (α) when compounds of the formulae (I-1-a) to (I-4-a) in which A, B, D, Q$^1$, Q$^2$, V, W, X, Y, Z and m are each as defined above are reacted with compounds of the formula (XVII):

in which
R$^9$ and R$^{10}$ are each as defined above and R$^{10}$ does not represent the group CO—R$^{11}$
in the presence of a solvent, if appropriate in the presence of an acidic catalyst, with distillative removal of an azeotrope or in the presence of a dehydrating agent (for example molecular sieve),
or β) when, in the case that R$^9$ and R$^{10}$ each represent hydrogen, nitriles of the formula (XVIII):

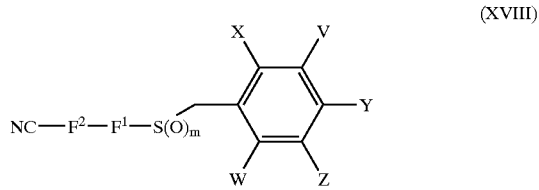

in which
V, W, X, Y, Z and m are each as defined above and F$^1$ and F$^2$ represent the groups

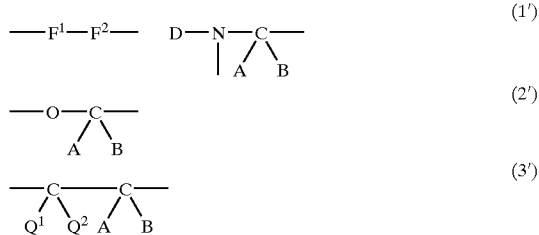

in which the radicals A, B, D, Q$^1$ and Q$^2$ are each as defined above
are cyclized intramolecularly in the presence of a solvent and in the presence of a base, (N) that compounds of the formulae (I-1-i) to (I-4-i) shown above in which A, B, D, Q$^1$, Q$^2$, R$^9$, V, W, X, Y, Z and m are each as defined above and R$^{10}$ represents the group CO—R$^{11}$ are obtained when compounds of the formulae (I-1-i$^1$) to (I-4-i$^1$):

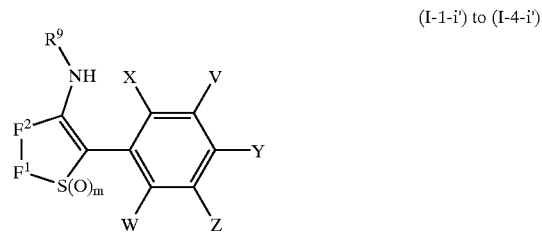

in which
F$^1$, F$^2$, R$^9$, V, W, X, Y, Z and m are each as defined above
α) are reacted with acid halides of the general formula (XIX)

in which
R$^{11}$ is as defined above, but does not represent hydrogen,
Hal represents halogen, in particular chlorine or bromine,
if appropriate in the presence of a diluent and if appropriate in the presence of an acid binder,
or β) are reacted with carboxylic anhydrides of the general formula (XX):

in which
R$^{11}$ are as defined above and, independently of one another, are identical or different, but do not represent hydrogen,
if appropriate in the presence of a diluent and if appropriate in the presence of an acid binder,
it also being possible to use mixtures of the reagents of the formulae (XVIII) and (XIX),
or γ) are reacted with orthoformic esters of the formula (XXI):

in which
R$^{11}$ represents hydrogen
and
Alk represents C$_1$–C$_4$-alkyl (in particular methyl or ethyl),
if appropriate in the presence of a diluent and if appropriate in the presence of a base.

(O) Moreover, it has been found that compounds of the formula (I-1-i)

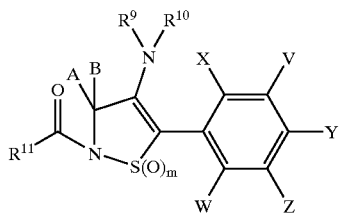
(I-1-i)

shown above
in which
A, B, $R^9$, $R^{10}$, $R^{11}$, V, W, X, Y, Z and m are each as defined above
are obtained
when compounds of the formula (I-1-i$^2$):

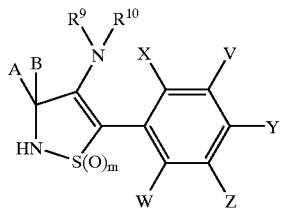
(I-1-i$^2$)

in which
A, B, $R^9$, $R^{10}$, V, W, X, Y, Z and m are each as defined above
are reacted with acid chlorides of the general formula (XIX):

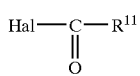
(XIX)

in which
$R^{11}$ is as defined above, but does not represent hydrogen,
Hal represents halogen, in particular chlorine and bromine,
if appropriate in the presence of a diluent and preferably in the presence of a base.

Furthermore, it has been found that the novel compounds of the formula (I) have very good pesticidal activity, preferably as insecticides and acaricides, and also as herbicides.

The formula (I) provides a general definition of the compounds according to the invention. Preferred substituents or ranges of the radicals listed in the formulae mentioned above and below are illustrated below:

V preferably represents hydrogen, halogen, $C_1-C_6$-alkyl, $C_1-C_6$-halogenoalkyl, $C_1-C_6$-alkoxy, $C_1-C_6$-halogenoalkoxy, phenyl, nitro or cyano, W preferably represents hydrogen, halogen, $C_1-C_6$-alkyl, $C_1-C_6$-halogenoalkyl, $C_1-C_6$-alkoxy, $C_1-C_6$-halogenoalkoxy, nitro or cyano, X preferably represents hydrogen, halogen, $C_1-C_6$-alkyl, $C_1-C_6$-halogenoalkyl, $C_1-C_6$-alkoxy, $C_2-C_6$-alkenyl, $C_2-C_6$-alkinyl, $C_1-C_6$-alkylthio, $C_1-C_6$-alkylsulphinyl, $C_1-C_6$-alkylsulphonyl, $C_1-C_6$-halogenoalkoxy, nitro, cyano or in each case optionally halogen-, $C_1-C_6$-alkyl-, $C_1-C_6$-alkoxy-, $C_1-C_4$-halogenoalkyl-, $C_1-C_4$-halogenoalkoxy-, nitro- or cyano-substituted phenyl, phenyl-$C_1-C_4$-alkyl, phenoxy, phenylthio, benzyloxy or benzylthio, Y and Z independently of one another each preferably represent hydrogen, halogen, $C_1-C_6$-alkyl, $C_1-C_6$-halogenoalkyl, $C_1-C_6$-alkoxy, $C_2-C_6$-alkenyl, $C_2-C_6$-alkinyl, $C_1-C_6$-alkylthio, $C_1-C_6$-alkylsulphinyl, $C_1-C_6$-alkylsulphonyl, $C_1-C_6$-halogenoalkoxy, nitro, cyano or in each case optionally halogen-, $C_1-C_6$-alkyl-, $C_1-C_6$-alkoxy-, $C_1-C_4$-halogenoalkyl-, $C_1-C_6$-halogenoalkoxy-, nitro- or cyano-substituted phenyl, phenyl-$C_1-C_4$-alkyl, phenoxy, phenylthio, benzyloxy or benzylthio, X and V together with the carbon atoms to which they are attached preferably represent an optionally halogen- or alkyl-substituted 5- or 6-membered ring which may optionally be interrupted by one or two heteroatoms, with the proviso that Y and Z do not form a ring, Y and Z together with the carbon atoms to which they are attached preferably represent an optionally halogen- or alkyl-substituted 5- or 6-membered ring which may optionally be interrupted by one or two heteroatoms, with the proviso that X and V do not form a ring, m preferably represents the numbers 1 and 2, with the proviso that at least one radical of the substituents V, W, X, Y or Z has to be different from hydrogen, $F^1$ and $F^2$ each preferably represent one of the groups:

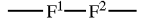
(1)

(2)

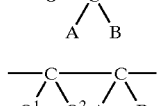
(3)

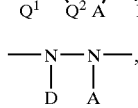
(4)

A preferably represents hydrogen or in each case optionally halogen-substituted $C_1-C_{12}$-alkyl, $C_3-C_8$-alkenyl, $C_1-C_{10}$-alkoxy-$C_1-C_8$-alkyl, di-, tri- or tetra-$C_1-C_8$-alkoxy-$C_1-C_8$-alkyl, $C_1-C_{10}$-alkylthio-$C_1-C_6$-alkyl, optionally halogen-, $C_1-C_6$-alkyl- or $C_1-C_6$-alkoxy-substituted $C_3-C_8$-cycloalkyl in which optionally one or two not directly adjacent ring members are replaced by oxygen and/or sulphur, or represents in each case optionally halogen-, $C_1-C_6$-alkyl-, $C_1-C_6$-halogenoalkyl-, $C_1-C_6$-alkoxy-, $C_1-C_6$-halogenoalkoxy-, cyano- or nitro-substituted $C_6$- or $C_{10}$-aryl (phenyl or naphthyl), hetaryl having 5 to 6 ring atoms (for example furanyl, pyridyl, imidazolyl, triazolyl, pyrazolyl, pyrimidyl, thiazolyl or thienyl) or $C_6$- or $C_{10}$-aryl-$C_1-C_6$-alkyl (phenyl-$C_1-C_6$-alkyl or naphthyl-$C_1-C_6$-alkyl), B preferably represents hydrogen, $C_1-C_{12}$-alkyl or $C_1-C_8$-alkoxy-$C_1-C_6$-alkyl, or A, B and the carbon atom to which they are attached preferably represent saturated $C_3-C_{10}$-cycloalkyl or unsaturated $C_5-C_{10}$-cycloalkyl in which optionally one ring member is replaced by oxygen or sulphur and which are optionally mono- or disubstituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or A, B and the carbon atom to which they are attached preferably represent $C_3$–$C_6$-cycloalkyl which is substituted by an alkylenediyl group which optionally contains one or two not directly adjacent oxygen and/or sulphur atoms, or by an alkylenedioxyl or by an alkylenedithioyl group which, together with the carbon atom to which it is attached, forms a further five- to eight-membered ring, or A, B and the carbon atom to which they are attached preferably represent $C_3$–$C_8$-cycloalkyl or $C_5$–$C_8$-cycloalkenyl in which two substituents together with the carbon atoms to which they are attached represent in each case optionally $C_1$–$C_6$-alkyl-, $C_1$–$C_6$-alkoxy- or halogen-substituted $C_2$–$C_6$-alkanediyl, $C_2$–$C_6$-alkenediyl or $C_4$–$C_6$-alkanedienediyl in which optionally one methylene group is replaced by oxygen or sulphur, D preferably represents hydrogen, in each case optionally halogen-substituted $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, di-, tri- or tetra-$C_1$–$C_8$-alkoxy-$C_2$–$C_8$-alkyl, $C_1$–$C_{10}$-alkylthio-$C_2$–$C_8$-alkyl, optionally halogen-, $C_1$–$C_4$-alkyl-, $C_1$–$C_4$-alkoxy- or $C_1$–$C_4$-halogenoalkyl-substituted $C_3$–$C_8$-cycloalkyl in which optionally one ring member is replaced by oxygen or sulphur, or represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$–$C_6$-alkyl or hetaryl-$C_1$–$C_6$-alkyl having 5 or 6 ring atoms (for example furanyl-, imidazolyl-, pyridyl-, thiazolyl-, pyrazolyl-, pyrimidyl-, pyrrolyl-, thienyl- or triazolyl-$C_1$–$C_6$-alkyl) or represents the group CO—$R^{11}$, or A and D together preferably represent in each optionally substituted $C_3$–$C_6$-alkanediyl or $C_3$–$C_6$-alkenediyl in which optionally one methylene group is replaced by a carbonyl group, oxygen or sulphur, possible substituents being, in each case:

halogen, hydroxyl, mercapto or in each case optionally halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy, where optionally two adjacent substituents together with the carbon atoms to which they are attached form a further saturated or unsaturated cycle having 5 or 6 ring atoms (in the case of the compound of the formula (I-1), A and D then represent together with the atoms to which they are attached, for example for the groups AD-1 to AD-10 mentioned further below) which may contain oxygen or sulphur, or which may optionally contain one of the following groups:

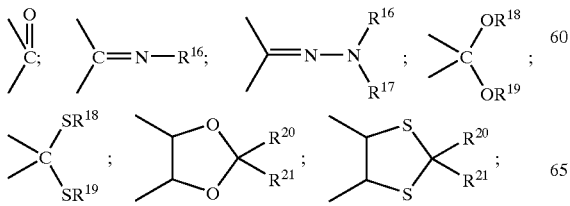

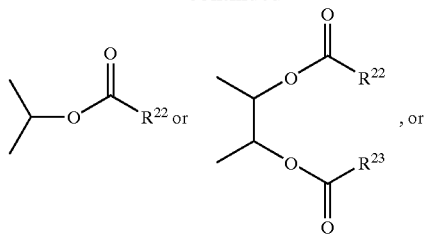

A and $Q^1$ together preferably represent $C_3$–$C_6$-alkanediyl or $C_4$–$C_6$-alkenediyl, each of which is optionally mono- or disubstituted by identical or different substituents from the group consisting of halogen and hydroxyl, by $C_1$–$C_{10}$-alkyl, $C_1$–$C_6$-alkoxy, $C_1$–$C_6$-alkylthio, $C_3$–$C_7$-cycloalkyl, each of which is optionally mono- to trisubstituted by identical or different substituents from the group consisting of halogen, or by benzyloxy or phenyl, each of which is optionally mono- to trisubstituted by identical or different substituents from the group consisting of halogen, $C_1$–$C_6$-alkyl and $C_1$–$C_6$-alkoxy, or represent optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted alkanedienediyl, with the proviso that B and $Q^2$ together with the carbon atoms to which they are attached represent a double bond and at least one of the substituents W or X does not represent hydrogen, $Q^1$ preferably represents hydrogen, $C_1$–$C_6$-alkyl, $C_1$–$C_6$-alkoxy-$C_1$–$C_2$-alkyl, $C_1$–$C_6$-alkylthio-$C_1$–$C_2$-alkyl, optionally $C_1$–$C_4$-alkyl- or $C_1$–$C_4$-alkoxy-substituted $C_3$–$C_8$-cycloalkyl in which optionally one methylene group is replaced by oxygen or sulphur, or represents optionally halogen-, $C_1$–$C_4$-alkyl-, $C_1$–$C_4$-alkoxy-, $C_1$–$C_2$-halogenoalkyl-, $C_1$–$C_2$-halogenoalkoxy-, cyano- or nitro-substituted phenyl, or $Q^2$ preferably represents hydrogen or $C_1$–$C_4$-alkyl, G preferably represents hydroxyl (a) or represents one of the groups:

(b)

(c)

(d)

(e)

(f)

(g)

-continued

—O—R⁸ or (h)

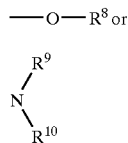
(i)

in which
E represents a metal ion or an ammonium ion,
L represents oxygen or sulphur and
M represents oxygen or sulphur, $R^1$ preferably represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl or optionally halogen-, $C_1$–$C_6$-alkyl- or $C_1$–$C_6$-alkoxy-substituted $C_3$–$C_8$-cycloalkyl in which optionally one or more (preferably one or two) not directly adjacent ring members are replaced by oxygen and/or sulphur,
represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl,
represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl,
represents optionally halogen- or $C_1$–$C_6$-alkyl-substituted 5- or 6-membered hetaryl (for example pyrazolyl, thiazolyl, pyridyl, pyrimidyl, furanyl or thienyl),
represents optionally halogen- or $C_1$–$C_6$-alkyl-substituted phenoxy-$C_1$–$C_6$-alkyl, or
represents optionally halogen-, amino- or $C_1$–$C_6$-alkyl-substituted 5- or 6-membered hetaryloxy-$C_1$–$C_6$-alkyl (for example pyridyloxy-$C_1$–$C_6$-alkyl, pyrimidyloxy-$C_1$–$C_6$-alkyl or thiazolyloxy-$C_1$–$C_6$-alkyl), $R^2$ preferably represents in each case optionally halogen-substituted $C_1$–$C_{20}$-alkyl, $C_2$–$C_{20}$-alkenyl, $C_1$–$C_8$-alkoxy-$C_2$–$C_8$-alkyl, poly-$C_1$–$C_8$-alkoxy-$C_2$–$C_8$-alkyl, represents optionally halogen-, $C_1$–$C_6$-alkyl- or $C_1$–$C_6$-alkoxy-substituted $C_3$–$C_8$-cycloalkyl, or
represents in each case optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl, $R^3$ preferably represents optionally halogen-substituted $C_1$–$C_8$-alkyl or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl, $R^4$ and $R^5$ independently of one another each preferably represent in each case optionally halogen-substituted $C_1$–$C_8$-alkyl, $C_1$–$C_8$-alkoxy, $C_1$–$C_8$-alkyl-amino, di-($C_1$–$C_8$-alkyl)amino, $C_1$–$C_8$-alkylthio, $C_2$–$C_8$-alkenylthio, $C_3$–$C_7$-cycloalkylthio or represent in each case optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio, $R^6$ and $R^7$ independently of one another each preferably represent hydrogen, represent in each case optionally halogen-substituted $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$-alkyl, represent optionally halogen-, $C_1$–$C_8$-halogenoalkyl-, $C_1$–$C_8$-alkyl- or $C_1$–$C_8$-alkoxy-substituted phenyl, optionally halogen-, $C_1$–$C_8$-alkyl-, $C_1$–$C_8$-halogenoalkyl- or $C_1$–$C_8$-alkoxy-substituted benzyl or together with the N atom to which they are attached represent an optionally $C_1$–$C_4$-alkyl-substituted $C_3$–$C_6$-alkylene radical in which optionally one carbon atom is replaced by oxygen or sulphur, $R^8$ preferably represents in each case optionally halogen-substituted $C_1$–$C_{10}$-alkyl, $C_3$–$C_8$-alkenyl, $C_3$–$C_8$-alkinyl, $C_1$–$C_8$-alkoxy-$C_1$–$C_4$-alkyl, $C_3$–$C_8$-alkenyloxy-$C_1$–$C_4$-alkyl, $C_3$–$C_8$-alkinyloxy-$C_1$–$C_4$-alkyl, $C_1$–$C_8$-alkylcarbonyl-$C_1$–$C_4$-alkyl, $C_1$–$C_8$-alkoxycarbonyl-$C_1$–$C_4$-alkyl, represents optionally fluorine-, $C_1$–$C_4$-alkyl- or $C_1$–$C_4$-alkoxy-substituted cycloalkyl or represents optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl-$C_1$–$C_4$-alkyl, phenylcarbonyl-$C_1$–$C_4$-alkyl or phenoxy-$C_1$–$C_4$-alkyl, $R^9$ preferably represents hydrogen, optionally halogen-substituted $C_1$–$C_{10}$-alkyl, $C_3$–$C_{10}$-alkenyl, $C_1$–$C_8$-alkoxy-$C_1$–$C_8$-alkyl, $C_1$–$C_8$-alkylthio-$C_1$–$C_8$-alkyl, cycloalkyl having 3 to 8 ring atoms which may be interrupted by an oxygen or sulphur atom, represents phenyl, phenyl-$C_1$–$C_6$-alkyl or phenoxy-$C_1$–$C_6$-alkyl or hetaryl-$C_1$–$C_6$-alkyl having in each case 5 or 6 ring atoms, where the ring contains 1 or 2 identical or different oxygen, nitrogen and sulphur atoms, each of which is optionally mono- to trisubstituted by identical or different substituents from the group consisting of halogen, $C_1$–$C_6$-alkyl, $C_1$–$C_6$-alkoxy, $C_1$–$C_4$-halogenoalkyl, $C_1$–$C_4$-halogenoalkoxy, cyano and nitro, or $R^{10}$ preferably represents hydrogen, $C_1$–$C_{10}$-alkyl, $C_3$–$C_{10}$-alkenyl or represents a group CO—$R^{11}$, or $R^9$ and $R^{10}$ together with the nitrogen atom to which they are attached preferably represent an optionally $C_1$–$C_4$-alkyl-substituted three- to seven-membered saturated ring in which optionally one methylene group which is not directly adjacent to the nitrogen atom may be replaced by an oxygen or sulphur atom, $R^{11}$ preferably represents hydrogen, in each case optionally halogen-substituted $C_1$–$C_{10}$-alkyl, $C_3$–$C_{10}$-alkenyl, $C_1$–$C_{10}$-alkoxy, optionally halogen-, $C_1$–$C_4$-alkyl-, $C_1$–$C_4$-alkoxy-substituted $C_3$–$C_8$-cycloalkyl or represents optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, phenyl-$C_1$–$C_6$-alkyl, benzyloxy or phenoxy, $R^{16}$ preferably represents hydrogen, represents in each case optionally halogen-substituted $C_1$–$C_8$-alkyl or $C_1$–$C_8$-alkoxy, represents optionally halogen-, $C_1$–$C_4$-alkyl- or $C_1$–$C_4$-alkoxy-substituted $C_3$–$C_8$-cycloalkyl in which optionally one methylene group is replaced by oxygen or sulphur, or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl or phenyl-$C_1$–$C_4$-alkoxy, $R^{17}$ preferably represents hydrogen or $C_1$–$C_8$-alkyl, or $R^{16}$ and $R^{17}$ together preferably represent $C_4$–$C_6$-alkanediyl, $R^{18}$ and $R^{19}$ are identical or different and each preferably represents $C_1$–$C_6$-alkyl, or $R^{18}$ and $R^{19}$ together preferably represent a $C_2$–$C_4$-alkanediyl radical which is optionally substituted by $C_1$–$C_6$-alkyl, $C_1$–$C_6$-halogenoalkyl or by optionally halogen-, $C_1$–$C_6$-alkyl-, $C_1$–$C_4$-halogenoalkyl-, $C_1$–$C_6$-alkoxy-, $C_1$–$C_4$-halogenoalkoxy-, nitro- or cyano-substituted phenyl, $R^{20}$ and $R^{21}$ independently of one another each preferably represent hydrogen, represent optionally halogen-substituted $C_1$–$C_8$-alkyl or represent optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, or $R^{20}$ and $R^{21}$ together with the carbon atom to which they are attached preferably represent a carbonyl group or represent optionally halogen-, $C_1$–$C_4$-alkyl- or $C_1$–$C_4$-alkoxy-substituted $C_5$–$C_7$-cycloalkyl in which optionally one methylene group is replaced by oxygen or sulphur, $R^{22}$ and $R^{23}$ independently of one another each preferably represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

In the radical definitions mentioned as being preferred, halogen, including as substituent, such as, for example, in halogenoalkyl, represents fluorine, chlorine, bromine and iodine, in particular fluorine and chlorine.

X particularly preferably represents hydrogen, fluorine, chlorine, bromine, $C_1$–$C_4$-alkyl, $C_1$–$C_4$-alkoxy, $C_1$–$C_4$-halogenoalkyl, $C_1$–$C_4$-halogenoalkoxy, nitro or cyano or represents optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy or benzyloxy, V particularly preferably represents hydrogen, fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, phenyl, nitro or cyano, W particularly preferably represents hydrogen, fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, nitro or cyano, Y and Z independently of one another each particularly preferably represent hydrogen, fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano, nitro or each represent optionally fluorine-, chlorine-, bromine-, $C_1$–$C_4$-alkyl-, $C_1$–$C_2$-halogenoalkyl-, $C_1$–$C_4$-alkoxy-, $C_1$–$C_2$-halogenoalkoxy-, cyano- or nitro-substituted phenyl, phenoxy or benzyloxy, X and V together with the carbon atoms to which they are attached particularly preferably represent an optionally fluorine-, chlorine- or $C_1$–$C_4$-alkyl-substituted 5- or 6-membered ring which may optionally be interrupted by two not directly adjacent oxygen atoms, with the proviso that Y and Z do not form a ring, Y and Z together with the carbon atoms to which they are attached particularly preferably represent an optionally fluorine-, chlorine- or $C_1$–$C_4$-alkyl-substituted 5- or 6-membered ring which may optionally be interrupted by one or two oxygen atoms, with the proviso that X and V do not form a ring, m particularly preferably represents the numbers 1 and 2, with the proviso that at least one radical of the substituents V, W, X, Y or Z has to different from hydrogen, $F^1$ and $F^2$ each particularly preferably represent one of the groups:

A particularly preferably represents hydrogen, in each case optionally fluorine- or chlorine-substituted $C_1$–$C_{10}$-alkyl, $C_1$–$C_8$-alkoxy-$C_1$–$C_6$-alkyl, optionally fluorine-, chlorine-, $C_1$–$C_4$-alkyl- or $C_1$–$C_4$-alkoxy-substituted $C_3$–$C_7$-cycloalkyl in which optionally one ring member is replaced by oxygen or sulphur, or represents phenyl or phenyl-$C_1$–$C_2$-alkyl, each of which is optionally mono- to disubstituted by fluorine, chlorine, bromine, $C_1$–$C_4$-alkyl, $C_1$–$C_2$-halogenoalkyl, $C_1$–$C_4$-alkoxy, $C_1$–$C_2$-halogenoalkoxy, cyano or nitro, B particularly preferably represents hydrogen or $C_1$–$C_6$-alkyl, or A, B and the carbon atom to which they are attached particularly preferably represent saturated or unsaturated $C_5$–$C_7$-cycloalkyl in which optionally one ring member is replaced by oxygen or sulphur and which is optionally monosubstituted by $C_1$–$C_6$-alkyl, $C_5$–$C_6$-cycloalkyl, $C_1$–$C_2$-halogenoalkyl, $C_1$–$C_6$-alkoxy, fluorine, chlorine or phenyl, or A, B and the carbon atom to which they are attached particularly preferably represent $C_5$–$C_6$-cycloalkyl which is substituted by an alkylenediyl group which optionally contains one or two not directly adjacent oxygen or sulphur atoms or by an alkylenedioxyl or by an alkylenedithiol group which together with the carbon atom to which it is attached forms a further 5- or 6-membered ring, or A, B and the carbon atom to which they are attached particularly preferably represent $C_3$–$C_6$-cycloalkyl or $C_5$–$C_6$-cycloalkenyl in which two substituents together with the carbon atoms to which they are attached represent $C_2$–$C_4$-alkanediyl, $C_2$–$C_4$-alkenediyl in which optionally one methylene group is replaced by oxygen or sulphur, or butadienediyl, each of which is optionally substituted by $C_1$–$C_5$-alkyl, $C_1$–$C_5$-alkoxy, fluorine, chlorine or bromine, D particularly preferably represents hydrogen, represents in each case optionally fluorine- or chlorine-substituted $C_1$–$C_8$-alkyl, $C_3$–$C_6$-alkenyl, $C_1$–$C_6$-alkoxy-$C_2$–$C_4$-alkyl or $C_1$–$C_6$-alkylthio-$C_2$–$C_4$-alkyl, represents optionally fluorine-, chlorine-, $C_1$–$C_4$-alkyl-, $C_1$–$C_4$-alkoxy- or $C_1$–$C_2$-halogenoalkyl-substituted $C_3$–$C_7$-cycloalkyl in which optionally one methylene group is replaced by oxygen or sulphur, or represents phenyl or phenyl-$C_1$–$C_2$-alkyl, each of which is optionally mono- to disubstituted by fluorine, chlorine, bromine, $C_1$–$C_4$-alkyl, $C_1$–$C_2$-halogenoalkyl, $C_1$–$C_4$-alkoxy, $C_1$–$C_2$-halogenoalkoxy, cyano or nitro, or represents the group CO—$R^{11}$, A and D together particularly preferably represent optionally substituted $C_3$–$C_5$-alkanediyl in which one methylene group may be replaced by a carbonyl group, oxygen or sulphur, possible substituents being hydroxyl, $C_1$–$C_6$-alkyl or $C_1$–$C_4$-alkoxy, or A and D (in the case of the compounds of formula (I-1)) together with the atoms to which they are attached particularly preferably represent one of the groups AD-1 to AD-10:

AD-1
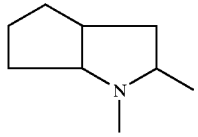

AD-2
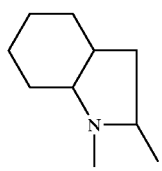

AD-3
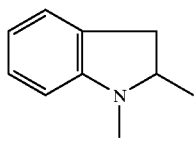

AD-4
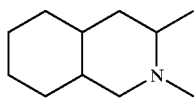

AD-5
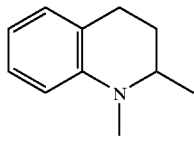

AD-6
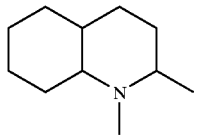

AD-7
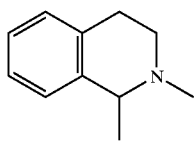

AD-8
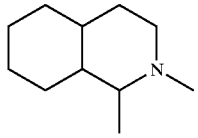

AD-9
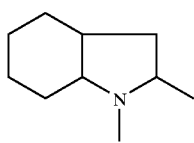

AD-10
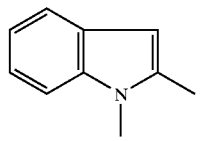

or

A and $Q^1$ together particularly preferably represent $C_3$–$C_4$-alkanediyl or $C_3$–$C_4$-alkenediyl, each of which is optionally mono- or disubstituted by identical or different substituents from the group consisting of hydroxyl, fluorine, chlorine, by $C_1$–$C_8$-alkyl or $C_1$–$C_4$-alkoxy, each of which is optionally mono- to trisubstituted by fluorine, or represents alkanedienediyl which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, with the proviso that B and $Q^2$ together with the carbon atoms to which they are attached represent a double bond and at least one of the substituents W or X does not represent hydrogen, $Q^1$ particularly preferably represents hydrogen, $C_1$–$C_4$-alkyl, $C_1$–$C_4$-alkoxy-$C_1$–$C_2$-alkyl, $C_1$–$C_4$-alkylthio-$C_1$–$C_2$-alkyl or optionally methyl- or methoxy-substituted $C_3$–$C_6$-cycloalkyl in which optionally one methylene group is replaced by oxygen or sulphur, or $Q^2$ particularly preferably represents hydrogen or $C_1$–$C_4$-alkyl, G particularly preferably represents hydroxyl (a) or represents one of the groups (b)
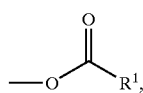

(c)
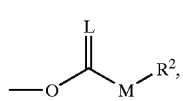

(d)
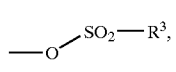

(e)
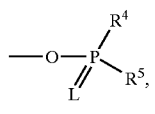

(f)
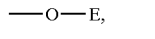

(g)
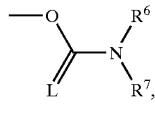

(h)
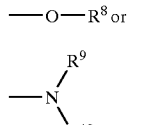

or (i)
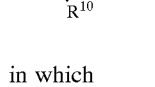

in which
E represents a metal ion or an ammonium ion,
L represents oxygen or sulphur and
M represents oxygen or sulphur, $R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_4$-alkyl, each of which is optionally mono- to trisubstituted by fluorine or chlorine, or represents optionally fluorine-, chlorine-, $C_1$–$C_5$-alkyl- or $C_1$–$C_5$-alkoxy-substituted $C_3$–$C_6$-cycloalkyl in which optionally one or two not directly adjacent ring members are replaced by oxygen and/or sulphur, represents phenyl which is optionally mono- to disubstituted by fluorine, chlorine, bromine, cyano, nitro, $C_1$–$C_4$-alkyl, $C_1$–$C_4$-alkoxy, $C_1$–$C_2$-halogenoalkyl, $C_1$–$C_2$-halogenoalkoxy, $C_1$–$C_2$-alkylthio or $C_1$–$C_2$-alkylsulphonyl, represents phenyl-$C_1$–$C_4$-alkyl which is optionally mono- to disubstituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, represents pyrazolyl, thiazolyl, pyridyl, pyrimidyl, furanyl or thienyl, each of which is optionally mono- to disubstituted by fluorine, chlorine, bromine or $C_1$–$C_4$-alkyl, $R^2$ particularly preferably represents $C_1$–$C_{16}$-alkyl, $C_2$–$C_{16}$-alkenyl or $C_1$–$C_6$-alkoxy-$C_2$–$C_6$-alkyl, each of which is optionally mono- to trisubstituted by fluorine, represents phenyl or benzyl, each of which is optionally mono- to disubstituted by fluorine, chlorine, bromine, cyano, nitro, $C_1$–$C_4$-alkyl, $C_1$–$C_3$-alkoxy, $C_1$–$C_2$-halogenoalkyl or $C_1$–$C_2$-halogenoalkoxy, $R^3$ particularly preferably represents $C_1$–$C_6$-alkyl which is optionally mono- to trisubstituted by fluorine, or represents phenyl which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, $R^4$ and $R^5$ independently of one another each particularly preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio, $C_3$–$C_6$-cycloalkylthio or represent phenyl, phenoxy or phenylthio, each of which is optionally mono- to disubstituted by fluorine, chlorine, bromine, nitro, cyano, $C_1$–$C_3$-alkoxy, $C_1$–$C_3$-halogenoalkoxy, $C_1$–$C_3$-alkyl or $C_1$–$C_3$-halogenoalkyl, $R^6$ particularly preferably represents $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, represents phenyl which is optionally mono- to disubstituted by fluorine, chlorine, bromine, $C_1$–$C_3$-halogenoalkyl, $C_1$–$C_4$-alkyl or $C_1$–$C_4$-alkoxy, represents benzyl which is optionally mono- to disubstituted by fluorine, chlorine, bromine, $C_1$–$C_4$-alkyl, $C_1$–$C_3$-halogenoalkyl or $C_1$–$C_4$-alkoxy, $R^7$ particularly preferably represents hydrogen, $C_1$–$C_6$-alkyl or $C_3$–$C_6$-alkenyl, $R^6$ and $R^7$ together with the nitrogen atom to which they are attached particularly preferably represent a 5- or 6-membered ring in which optionally one methylene group which is not directly adjacent to the nitrogen atom may be replaced by an oxygen or sulphur atom and which is optionally mono- to disubstituted by methyl or ethyl, $R^8$ particularly preferably represents $C_1$–$C_6$-alkyl, $C_3$–$C_6$-alkenyl, $C_3$–$C_6$-alkinyl, $C_1$–$C_6$-alkoxy-$C_1$–$C_2$-alkyl, $C_3$–$C_6$-alkenyloxy-$C_1$–$C_2$-alkyl, $C_3$–$C_8$-alkinyloxy-$C_1$–$C_2$-alkyl, $C_1$–$C_6$-alkylcarbonyl-$C_1$–$C_2$-alkyl, $C_1$–$C_6$-alkoxycarbonyl-$C_1$–$C_2$-alkyl, each of which is optionally mono- to trisubstituted by fluorine or chlorine, or represents phenyl-$C_1$–$C_2$-alkyl, phenylcarbonyl-$C_1$–$C_4$-alkyl or phenoxy-$C_1$–$C_2$-alkyl, each of which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, $R^9$ particularly preferably represents hydrogen, represents $C_1$–$C_6$-alkyl, $C_3$–$C_6$-alkenyl or $C_3$–$C_6$-cycloalkyl, each of which is optionally mono- to trisubstituted by fluorine or chlorine, represents phenyl-$C_1$–$C_2$-alkyl or pyridyl-$C_1$–$C_2$-alkyl, each of which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, $R^{10}$ particularly preferably represents hydrogen, $C_1$–$C_6$-alkyl, $C_3$–$C_6$-alkenyl or represents a group CO—$R^{11}$ or $R^9$ and $R^{10}$ together with the nitrogen atom to which they are attached particularly preferably represent a 5- or 6-membered saturated ring in which optionally one methylene group which is not directly adjacent to the nitrogen atom may be replaced by an oxygen or sulphur atom and which is optionally mono- to disubstituted by methyl or ethyl, $R^{11}$ particularly preferably represents hydrogen, represents $C_1$–$C_6$-alkyl, $C_3$–$C_6$-alkenyl, $C_1$–$C_6$-alkoxy, each of which is optionally mono- to trisubstituted by fluorine or chlorine, represents $C_3$–$C_6$-cycloalkyl which is optionally mono- to disubstituted by fluorine, chorine, methyl, ethyl, methoxy or ethoxy, or represents phenyl which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

In the radical definitions mentioned as being particularly preferred, halogen, including as substituent, such as, for example, in halogenoalkyl, represents fluorine, chlorine, bromine and iodine, in particular fluorine, chlorine and bromine, particularly preferably fluorine or chlorine.

V very particularly preferably represents hydrogen, fluorine, chlorine, bromine, nitro, methyl, phenyl, methoxy or trifluoromethyl, W very particularly preferably represents hydrogen, fluorine, chlorine, bromine, methyl, ethyl, trifluoromethyl, methoxy, X very particularly preferably represents hydrogen, bromine, fluorine, chlorine, methyl, ethyl, n-propyl, iso-propyl, methoxy, ethoxy, n-propoxy, iso-propoxy, trifluoromethyl, difluoromethoxy, trifluoromethoxy, nitro or cyano, or represents phenyl, phenoxy or benzyloxy, each of which is optionally mono- to disubstituted by fluorine, chlorine, bromine, methyl, tert-butyl, trifluoromethyl, methoxy, trifluoromethoxy, nitro or cyano, Y very particularly preferably represents hydrogen, fluorine, chlorine, bromine, methyl, ethyl, i-propyl, tert-butyl, trifluoromethyl, difluoromethyl, methoxy, ethoxy, isopropoxy, trifluoromethoxy, difluoromethoxy, cyano, nitro or represents phenyl which is optionally mono- to disubstituted by fluorine, chlorine, bromine, methyl, trifluoromethyl, methoxy, trifluoromethoxy, cyano or nitro, Z very particularly preferably represents hydrogen, fluorine, chlorine, bromine, methyl, trifluoromethyl, methoxy, trifluoromethoxy, cyano, nitro or represents phenyl which is optionally mono- to disubstituted by fluorine, chlorine, bromine, methyl, trifluoromethyl, methoxy, trifluoromethoxy, cyano or nitro, X and V together with the carbon atoms to which they are attached very particularly preferably represent an optionally fluorine- or methyl-substituted 5- or 6-membered ring which is interrupted by two not directly adjacent oxygen atoms, with the proviso that Y and Z do not form a ring, Y and Z together with the carbon atoms to which they are attached very particularly preferably represent an optionally fluorine- or methyl-substituted 5- or 6-membered ring which may be interrupted by one or two not directly adjacent oxygen atoms, with the proviso that X and V do not form a ring, m very particularly preferably represents the number 2, with the proviso that at least one radical of the substituents V, W, X, Y or Z has to be different from hydrogen, $F^1$ and $F^2$ each very particularly preferably represent one of the groups

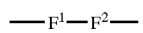

(1)

(2)

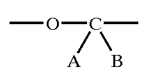

(3)

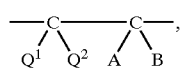

A very particularly preferably represents hydrogen, optionally fluorine-substituted $C_1$–$C_6$-alkyl, optionally fluorine-, methyl- or methoxy-substituted $C_3$–$C_6$-cycloalkyl or represents phenyl or benzyl, each of which is optionally mono- to disubstituted by fluorine, chlorine, bromine, methyl, iso-propyl, tert-butyl, methoxy, trifluoromethyl, trifluoromethoxy, cyano or nitro, B very particularly preferably represents hydrogen or $C_1$–$C_4$-alkyl, or A, B and the carbon atom to which they are attached very particularly preferably represent saturated $C_5$–$C_6$-cycloalkyl in which optionally one ring member is replaced by oxygen or sulphur and which is optionally monosubstituted by methyl, ethyl, n-propyl, isopropyl, butyl, iso-butyl, sec-butyl, tert-butyl, trifluoromethyl, methoxy, ethoxy, n-propoxy, iso-propoxy, n-butoxy, iso-butoxy, fluorine or chlorine, or A, B and the carbon atom to which they are attached very particularly preferably represent $C_5$–$C_6$-cycloalkyl in which two substituents together with the carbon atoms to which they are attached represent $C_2$–$C_4$-alkanediyl or $C_2$–$C_4$-alkenediyl in which in each case optionally one methylene group is replaced by oxygen or sulphur, or represent butadienediyl, D very particularly preferably represents hydrogen, represents in each case optionally fluorine- or chlorine-substituted $C_1$–$C_6$-alkyl, $C_3$–$C_4$-alkenyl, $C_1$–$C_4$-alkoxy-$C_2$–$C_3$-alkyl, $C_1$–$C_4$-alkylthio-$C_2$-alkyl or $C_3$–$C_6$-cycloalkyl in which optionally one methylene group is replaced by oxygen or sulphur, or represents phenyl or benzyl, each of which is optionally mono- to disubstituted by fluorine, chlorine, bromine, methyl, ethyl, n-propyl, iso-propyl, tert-butyl, methoxy, ethoxy, trifluoromethyl, trifluoromethoxy, cyano or nitro (in compounds of the formula (I-1), D preferably represents hydrogen), or represents the group CO—$R^{1f}$, or A and D together very particularly preferably represent optionally substituted $C_3$–$C_4$-alkanediyl in which optionally one carbon atom is replaced by sulphur and which is optionally substituted by methyl, or A and D (in the case of the compounds of the formula (I-1)) together with the atoms to which they are attached represent one of the groups AD-1 to AD-10:

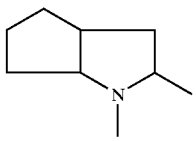

AD-1

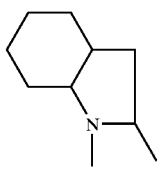

AD-2

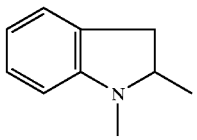

AD-3

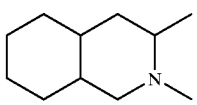

AD-4

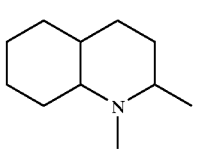

AD-6

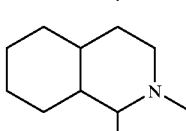

AD-8

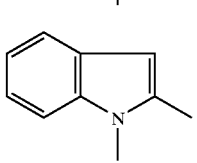

AD-10 or

A and $Q^1$ together very particularly preferably represent $C_3$–$C_4$-alkanediyl or butenediyl, each of which is optionally mono- or disubstituted by fluorine, chlorine, hydroxyl, methyl or methoxy, or represent alkanedienediyl which is optionally mono- to disubstituted by fluorine, chlorine, bromine, methyl, methoxy, trifluoromethoxy, cyano or nitro, with the proviso that B and $Q^2$ together with the carbon atoms to which they are attached represent a double bond and at least one of the substituents W or X does not represent hydrogen, $Q^1$ very particularly preferably represents hydrogen, methyl, cyclopropyl, cyclopentyl or cyclohexyl, $Q^2$ very particularly preferably represents hydrogen and methyl, G very particularly preferably represents hydroxyl (a) or represents one of the groups:

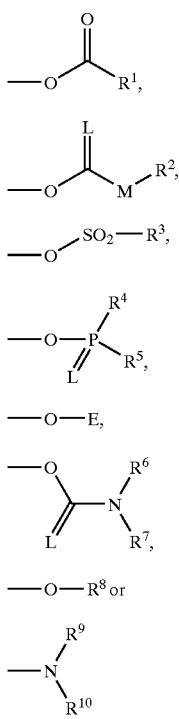

in particular (a), (b), (c), (g), (h) or (i)
in which
E represents a metal ion or an ammonium ion,
L represents oxygen or sulphur and
M represents oxygen or sulphur,
$R^1$ very particularly preferably represents $C_1$–$C_{14}$-alkyl, $C_2$–$C_{14}$-alkenyl, $C_1$–$C_4$-alkoxy-$C_1$–$C_4$-alkyl, $C_1$–$C_4$-alkylthio-$C_1$–$C_2$-alkyl, each of which is optionally mono- to trisubstituted by fluorine or chlorine, or represents $C_3$–$C_6$-cycloalkyl in which optionally one or two not directly adjacent ring members are replaced by oxygen and which is optionally mono- to disubstituted by fluorine, chlorine, methyl, ethyl, i-propyl, i-butyl, tert-butyl, methoxy, ethoxy or iso-propoxy,
represents phenyl which is optionally mono- to disubstituted by fluorine, chlorine, bromine, cyano, nitro, methyl, ethyl, i-propyl, methoxy, ethoxy, trifluoromethyl or trifluoromethoxy,
represents furanyl, thienyl or pyridyl, each of which is optionally mono- to disubstituted by fluorine, chlorine, bromine, methyl or ethyl,
$R^2$ very particularly preferably represents $C_1$–$C_{10}$-alkyl, $C_2$–$C_{10}$-alkenyl or $C_1$–$C_4$-alkoxy-$C_2$–$C_4$-alkyl, each of which is optionally mono- to trisubstituted by fluorine, or represents phenyl or benzyl, each of which is optionally mono- to disubstituted by fluorine, chlorine, cyano, nitro, methyl, ethyl, i-propyl, methoxy, ethoxy, trifluoromethyl or trifluoromethoxy,
$R^3$ very particularly preferably represents methyl, ethyl, n-propyl, isopropyl, each of which is optionally mono- to trisubstituted by fluorine, or represents phenyl which is optionally monosubstituted by fluorine, chlorine, bromine, methyl, tert-butyl, methoxy, trifluoromethyl, cyano or nitro,
$R^4$ and $R^5$ independently of one another each very particularly preferably represent $C_1$–$C_4$-alkyl, $C_1$–$C_4$-alkoxy, $C_1$–$C_4$-alkylamino, di-($C_1$–$C_4$-alkyl)amino, $C_1$–$C_4$-alkylthio or represent phenyl, phenoxy or phenylthio, each of which is optionally mono- to disubstituted by fluorine, chlorine, bromine, methyl, nitro, cyano, methoxy, trifluoromethoxy or trifluoromethyl,
$R^6$ very particularly preferably represents $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl, represents phenyl which is optionally mono- to disubstituted by fluorine, chlorine, bromine, trifluoromethyl, methyl or methoxy, represents benzyl which is optionally mono- to disubstituted by fluorine, chlorine, bromine, methyl, trifluoromethyl or methoxy,
$R^7$ very particularly preferably represents hydrogen, $C_1$–$C_4$-alkyl or $C_3$–$C_4$-alkenyl,
$R^6$ and $R^7$ together with the nitrogen atom to which they are attached very particularly preferably represent a 5- or 6-membered ring in which optionally one methylene group which is not directly adjacent to the nitrogen atom may be replaced by an oxygen or sulphur atom and which is optionally mono- to disubstituted by methyl,
$R^8$ very particularly preferably represents $C_1$–$C_4$-alkyl, $C_3$–$C_4$-alkenyl, $C_1$–$C_4$-alkoxy-methyl, $C_3$–$C_4$-alkenyloxy-methyl, $C_3$–$C_4$-alkinyloxy-methyl, $C_1$–$C_4$-alkylcarbonyl-methyl, $C_1$–$C_4$-alkoxycarbonyl-methyl, each of which is optionally mono- to trisubstituted by fluorine or chlorine, or represents benzyl, phenylcarbonyl-methyl or phenoxy-methyl, each of which is optionally mono- to disubstituted by fluorine, chlorine, bromine, methyl, methoxy, trifluoromethyl, trifluoromethoxy, cyano or nitro,
$R^9$ very particularly preferably represents hydrogen, represents $C_1$–$C_4$-alkyl, allyl, cyclopropyl, cyclopentyl, cyclohexyl, each of which is optionally mono- to trisubstituted by fluorine or chlorine, represents benzyl which is optionally mono- to disubstituted by fluorine, chlorine, bromine, methyl, ethyl, iso-propyl, tert-butyl, methoxy, iso-propoxy, trifluoromethyl, trifluoromethoxy, cyano or nitro,
$R^{10}$ very particularly preferably represents hydrogen, $C_1$–$C_4$-alkyl, allyl or represents a group CO—$R^{11}$, or
$R^9$ and $R^{10}$ together with the nitrogen atom to which they are attached very particularly preferably represent a 5- to 6-membered saturated ring in which optionally one methylene group which is not directly adjacent to the nitrogen atom may be replaced by an oxygen or sulphur atom and which is optionally mono- to disubstituted by methyl,
$R^{11}$ very particularly preferably represents hydrogen, represents $C_1$–$C_4$-alkyl, $C_3$–$C_4$-alkenyl, $C_1$–$C_4$-alkoxy, each of which is optionally mono- to trisubstituted by fluorine or chlorine, represents cyclopropyl, cyclopentyl or cyclohexyl, each of which is optionally monosubstituted by fluorine, chlorine, methyl or methoxy, or represents phenyl which is optionally mono- to disubstituted by fluorine, chlorine, bromine, methyl, methoxy, trifluoromethyl, trifluoromethoxy, cyano or nitro.

Particular emphasis is given to compounds of the formula (I) in which
V represents hydrogen, fluorine, chlorine, bromine, methyl, trifluoromethyl, nitro or phenyl,
W represents hydrogen, fluorine, chlorine, bromine, methyl, ethyl, X represents hydrogen, fluorine, chlorine, bromine, methyl, ethyl, n-propyl, iso-propyl, ethoxy, n-propoxy, iso-propoxy, methoxy, trifluoromethyl, nitro or cyano, Y represents hydrogen, fluorine, chlorine, bromine, methyl, ethyl, iso-propyl, tert-butyl, methoxy, ethoxy, iso-propoxy, difluoromethyl, trifluoromethyl, trifluoromethoxy, difluoromethoxy or phenyl, Z represents hydrogen, fluorine, chlorine, bromine, methyl, trifluoromethyl, Y and Z together with the carbon atoms to which they are attached form a 5-membered ring which may be interrupted by one or two not directly adjacent oxygen atoms, with the proviso that X and V do not form a ring, m represents 2, with the proviso that at least one radical of the substituents V, W, X, Y or Z has to be different from hydrogen, $F^1$ and $F^2$ each represent one of the groups:

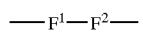

 (1)

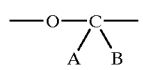 (2)

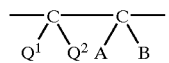 (3)

in which

A represents hydrogen, $C_1$–$C_4$-alkyl, represents phenyl or benzyl, each of which is optionally mono- to disubstituted by chlorine or fluorine, B represents hydrogen or $C_1$–$C_4$-alkyl, A and B and the carbon atom to which they are attached represent saturated cyclohexyl in which optionally one ring member is replaced by oxygen and which is optionally monosubstituted by methyl, ethyl, n-propyl, isopropyl, butyl, iso-butyl, sec-butyl, tert-butyl, trifluoromethyl, methoxy, ethoxy, n-propoxy, iso-propoxy, n-butoxy, iso-butoxy, fluorine or chlorine, D represents hydrogen, $C_1$–$C_4$-alkyl, represents phenyl or benzyl, each of which is optionally mono- or disubstituted by chlorine, fluorine, bromine, or represents a group CO—$R^{11}$, A and $Q^1$ together represent $C_3$–$C_4$-alkanediyl or butenediyl, each of which is optionally mono- or disubstituted by methyl, fluorine or chlorine, or represent alkanedienediyl which is optionally mono- or disubstituted by methyl or chlorine, with the proviso that B and $Q^2$ together with the carbon atoms to which they are attached represent a double bond and at least one of the substituents W or X does not represent hydrogen, G represents hydroxyl (a) or represents:

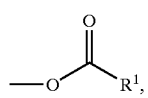 (b)

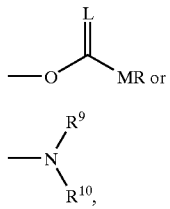

$R^1$ represents $C_1$–$C_8$-alkyl, $R^2$ represents $C_1$–$C_8$-alkyl,

L and M each represent oxygen, $R^9$ represents hydrogen, $R^{10}$ represents hydrogen or represents a group CO—$R^{11}$, $R^{11}$ represents $C_1$–$C_4$-alkyl.

Particular preference is given to compounds of the formula (I-1) in which D represents hydrogen, in which the substituent G represents the radicals (a), (b), (g), (h) or (i) and in which A, B, V, W, X, Y, Z, $R^1$, $R^2$, $R^6$, $R^7$, $R^8$, $R^9$, $R^{10}$ and m have the meanings listed in the very particularly preferred ranges.

Particular preference is given to compounds of the formula (I-2) in which D represents hydrogen, in which the substituent G represents the radicals (a), (b), (g), (h) or (i) and in which A, B, V, W, X, Y, Z, $R^1$, $R^2$, $R^6$, $R^7$, $R^8$, $R^9$, $R^{10}$ and m have the meanings listed in the very particularly preferred ranges.

Particular preference is given to compounds of the formula (I-3) in which D represents hydrogen, in which the substituents A and $Q^1$ each represent an optionally substituted alkanedienediyl radical, possible substituents being the radicals mentioned in the particularly preferred range, in which the substituent G represents the radicals (a), (b), (g), (h) or (i) and in which B, $Q^2$, V, W, X, Y, Z, $R^1$, $R^2$, $R^6$, $R^7$, $R^8$, $R^9$, $R^{10}$ and m have the meanings listed in the very particularly preferred ranges.

The abovementioned general or preferred radical definitions can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferably).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Particular preference is given to compounds of the formula (I) in which G represents hydrogen.

Saturated or unsaturated hydrocarbon radicals, such as alkyl or alkenyl, can in each case be straight-chain or branched as far as this is possible, including in combination with heteroatoms, such as, for example, in alkoxy.

Unless stated otherwise, optionally substituted radicals can be mono- or polysubstituted, where in the case of polysubstitution the substituents can be identical or different.

Using, according to process (A), ethyl 2{[(4-chlorobenzyl)sulphonyl]amino}-2-methylpropanoate as starting material, the course of the process according to the invention can be represented by the following reaction scheme:

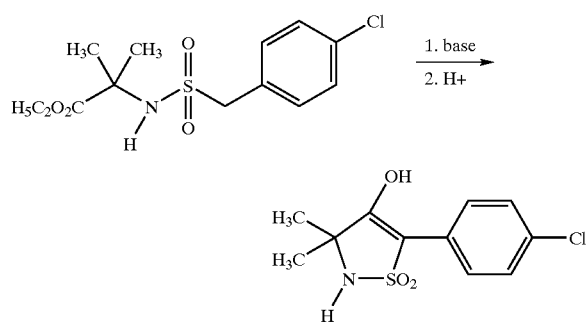

Using, according to process (B), ethyl 2-{[(2,6-dichlorobenzyl)sulphonyl]oxy}-2-methylpropanoate, the course of the process according to the invention can be represented by the following reaction scheme:

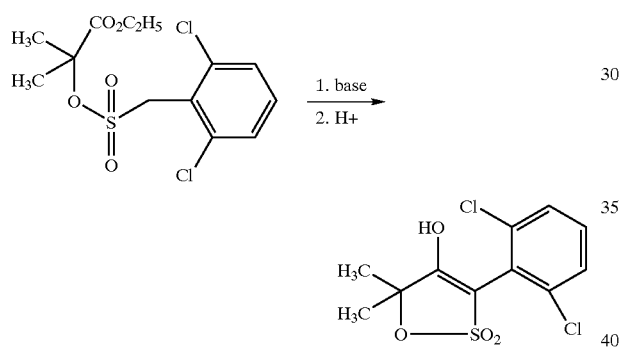

Using, according to process (C), ethyl 2-[(2,4-dichlorobenzyl)sulphonyl]benzoate, the course of the process according to the invention can be represented by the following reaction scheme:

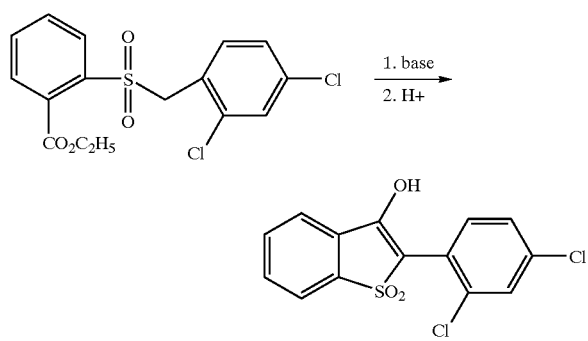

Using, according to process (D), for example, ethyl 2-[(4-nitrobenzyl)sulphonyl]tetrahydro-1(2H)-pyridazinecarboxylate as starting material, the course of the process according to the invention can be represented by the following reaction scheme:

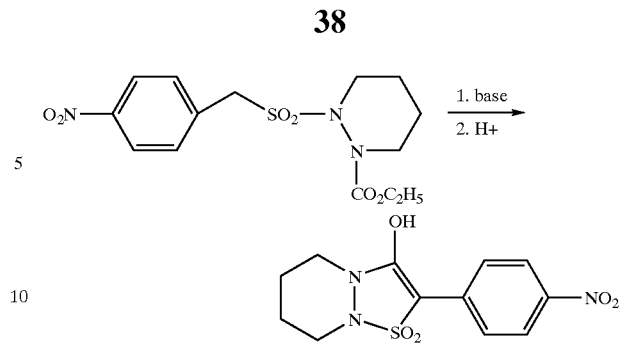

Using, according to process (E, variant α), 5-(2-chlorophenyl)-4-hydroxy-3,3-dimethyl-2,3-dihydro-1H-1-isothiazole-1,1-dione and pivaloyl chloride as starting materials, the course of the process according to the invention can be represented by the following reaction scheme:

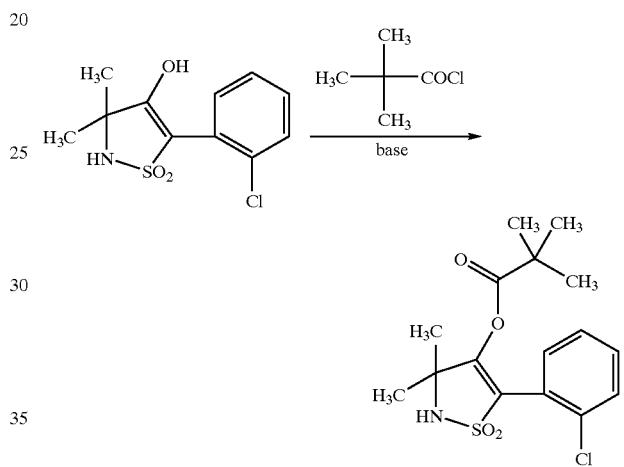

Using, according to process (E, variant β), 4-hydroxy-5,5-dimethyl-3-[3-(trifluoromethyl)phenyl]-1,2[lambda]$^6$-oxathiole-2,2(5H)-dione and acetic anhydride as starting materials, the course of the process according to the invention can be represented by the following reaction scheme:

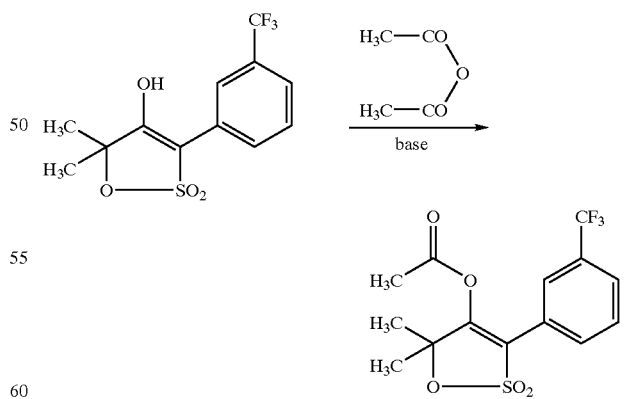

Using, according to process (F), 3-hydroxy-2-(4-nitrophenyl)-1H-1-benzothiophene-1,1-dione and ethoxyethyl chloroformate as starting materials, the course of the process according to the invention can be represented by the following reaction scheme:

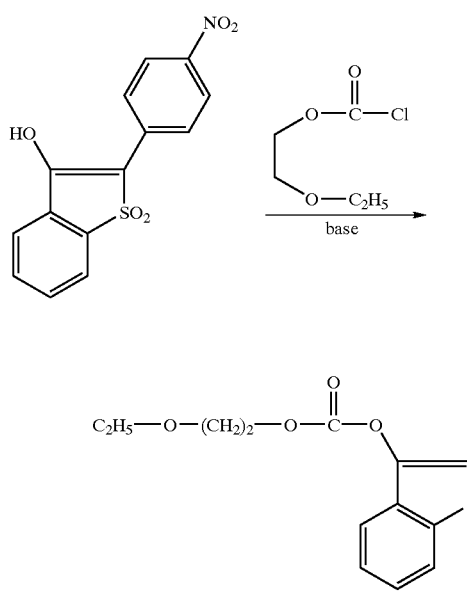

Using, according to process (G), 5-(3-chlorophenyl)-4-hydroxy-3,3-dimethyl-2,3-dihydro-1H-1-isothiazole-1,1-dione and methyl chloromonothioformate as starting materials, the course of the reaction can be represented as follows:

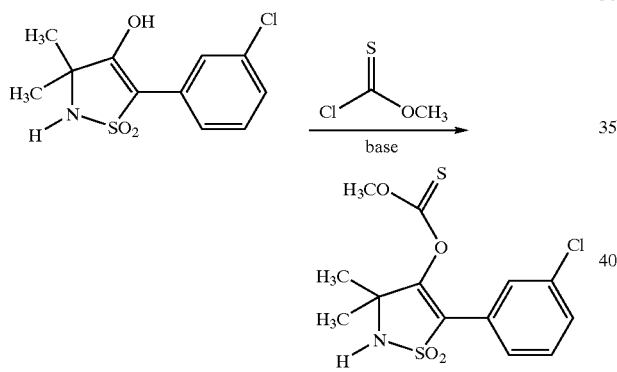

Using, according to process (H), 3-(3-chloro-4-trifluoromethylphenyl)-4-hydroxy-2-thia-1-azaspiro[4.5]dec-3,4-ene-2,2-dione and methanesulphonyl chloride as starting materials, the course of the reaction can be represented by the following reaction scheme:

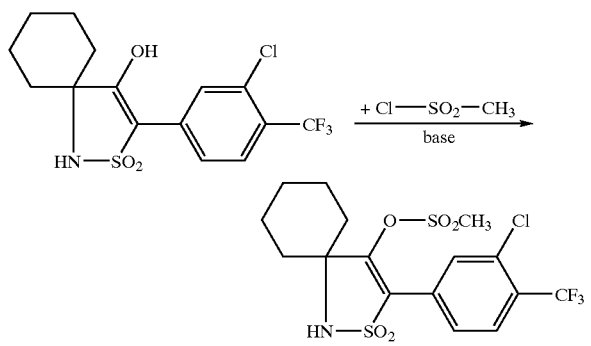

Using, according to process (I), 3-(3,4-dichlorophenyl)-4-hydroxy-5,5-dimethyl-1,2-oxathiole-2,2(5H)-dione and 2,2,2-trifluoroethyl methanethiophosphonyl chloride as starting materials, the course of the reaction can be represented by the following reaction scheme:

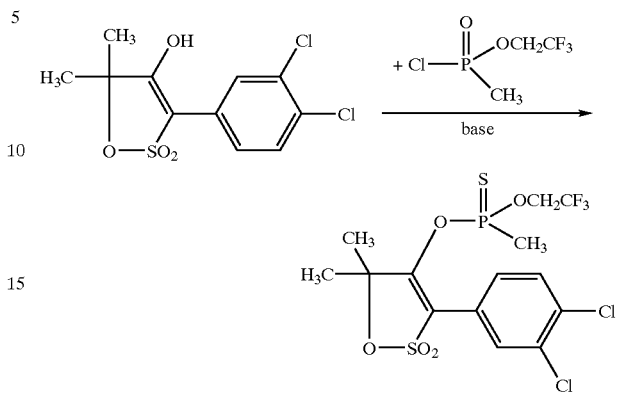

Using, according to process (J), 4-hydroxy-3,3-dimethyl-5-[2-(trifluoromethyl)-phenyl]-2,3-dihydro-1H-1-isothiazole-1,1-dione and NaOH as components, the course of the process according to the invention can be represented by the following reaction scheme:

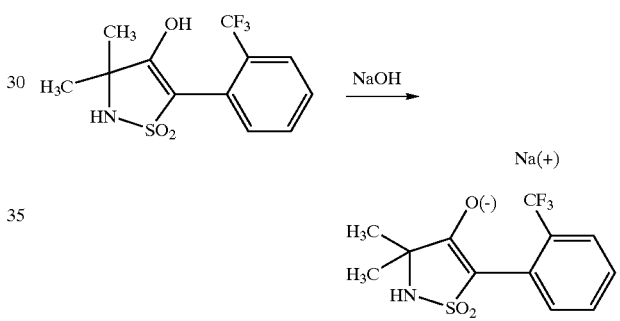

Using, according to process (K, variant α), 3-(4-chlorophenyl)-4-hydroxy-1-oxa-2-thiaspiro[4.4]non-3,4-ene-2,2-dione and ethyl isocyanate as starting materials, the course of the reaction can be represented by the following reaction scheme:

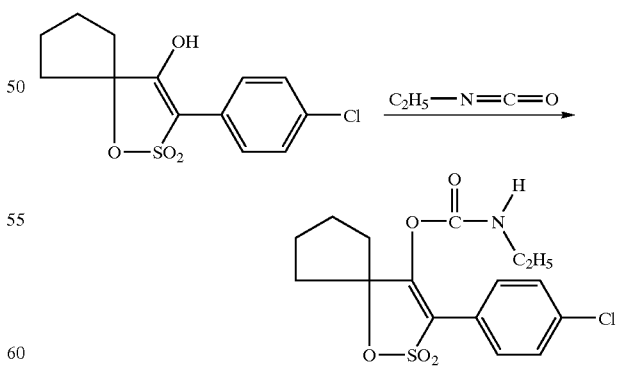

Using, according to process (K, variant β), 5-(2-chlorophenyl)-4-hydroxy-3-methyl-2,3-dihydro-1H-1-isothiazole-1,1-dione and dimethylcarbamoyl chloride as starting materials, the course of the reaction can be represented by the following scheme:

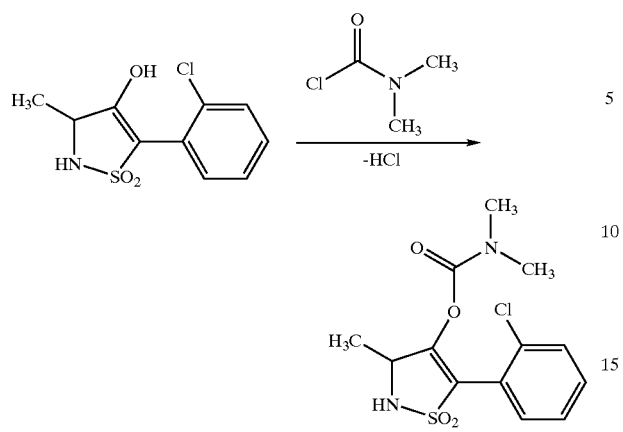

Using, according to process (L), 3-(2-fluorophenyl)-4-hydroxy-1-oxa-2-thia-spiro[4.5]dec-3,4-ene-2,2-dione and dimethyl sulphate as starting materials, the course of the reaction can be represented by the following reaction scheme:

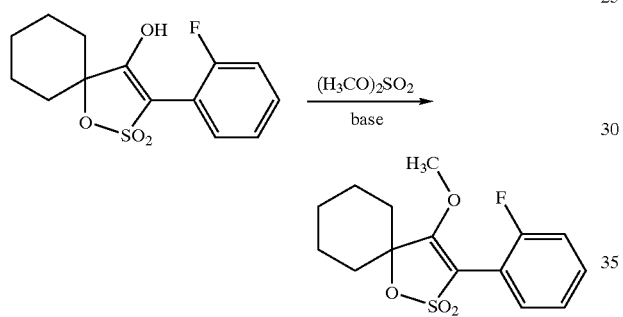

Using, according to process (M, variant α), 5-(4-chlorophenyl)-4-hydroxy-2-isopropyl-2,3-dihydro-1H-1-isothiazole-1,1-dione, methylamine and acetic acid as starting materials, the course of the reaction of the process according to the invention can be represented by the following reaction scheme:

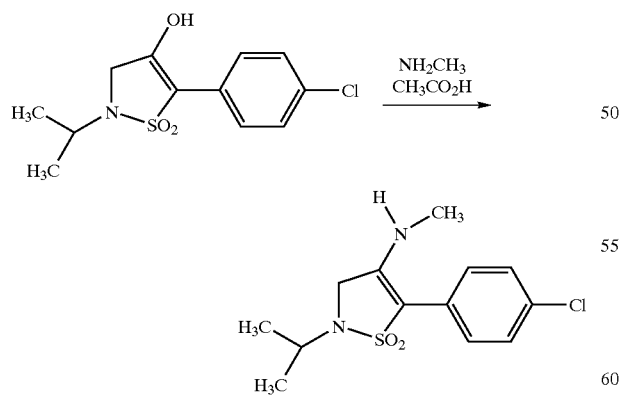

Using, according to process (M, variant β), N-(1-cyano-1-methylethyl)-(2,4-dichlorophenyl)methanesulphonamide and potassium tert-butoxide as starting materials, the course of the reaction of the process according to the invention can be represented by the following reaction scheme:

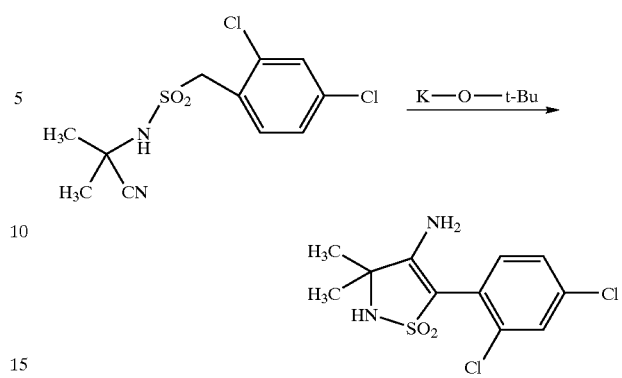

Using, according to process (N, variant α), 4-amino-5-[3-chloro-4-(trifluoromethyl)phenyl]-3,3-dimethyl-2,3-dihydro-1H-1-isothiazole-1,1-dione and propionyl chloride as starting materials, the course of the reaction of the process according to the invention can be represented by the following reaction scheme:

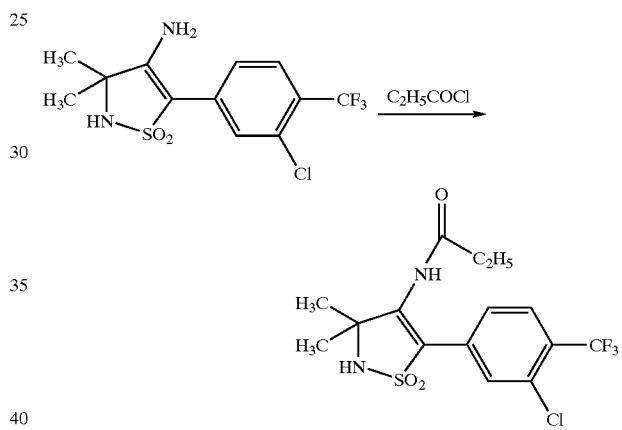

Using, according to process (N, variant β), 4-amino-3,3-dimethyl-5-[3-(trifluoromethyl)phenyl]-2,3-dihydro-1H-1-isothiazole-1,1-dione and acetic anhydride as starting materials, the course of the reaction of the process according to the invention can be represented by the following reaction scheme:

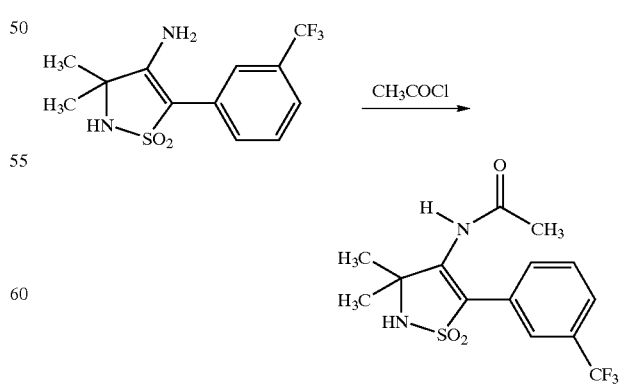

Using, according to process (N, variant γ), 4-amino-2-benzyl-5-(4-fluorophenyl)-3,3-dimethyl-2,3-dihydro-1H-1- isothiazole-1,1-dione and methyl orthoformate as starting materials, the course of the reaction of the process according to the invention can be described by the following reaction scheme:

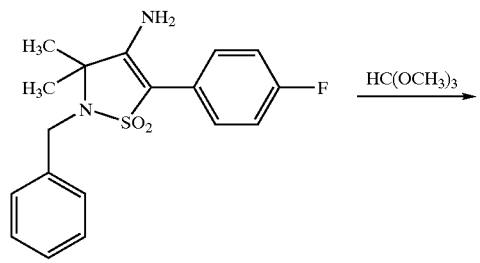

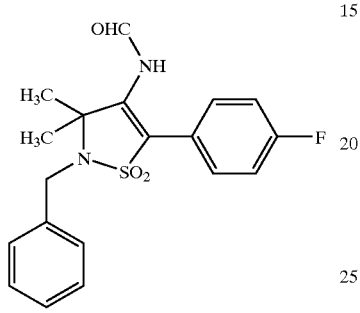

Using, according to process (O), 4-amino-3,3-dimethyl-5-[3-(trifluoromethyl)phenyl]-2,3-dihydro-1H-1-isothiazole-1,1-dione und acetyl chloride as starting materials and sodium hydride as base, the course of the reaction of the process according to the invention can be represented by the following reaction scheme:

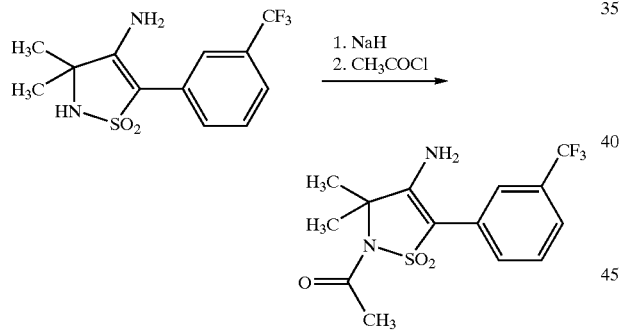

The compounds of the formula (II):

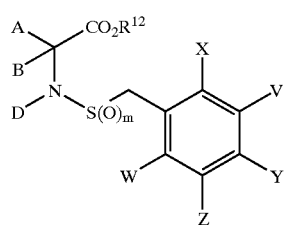

(II)

in which

A, B, D, V, W, X, Y, Z, $R^{12}$ and m are each as defined above and which are required as starting materials in the process (A) according to the invention are novel.

The amino acid esters of the formula (II) are obtained, for example, when amino acid derivatives of the formula (XXII):

(XXII)

in which

A, B, $R^{12}$ and D are each as defined above are reacted with substituted benzyl-$S(O)_m$ halides of the formula (XXIII):

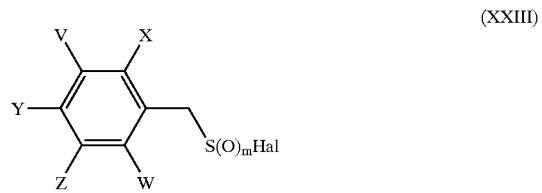

(XXIII)

in which

V, W, X, Y, Z and m are each as defined above and

Hal represents chlorine or bromine, in particular chlorine (H.-D. Stachel, G. Drasch, Arch. Pharm. 318, 304 (1985)), or when amino acids of the formula (XXIV):

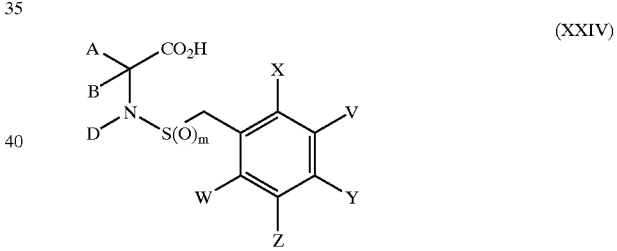

(XXIV)

in which

A, B, D, V, W, X, Y, Z and m are each as defined above are esterified (Chem. Ind. (London) 1568 (1968)).

The compounds of the formula (XXIV):

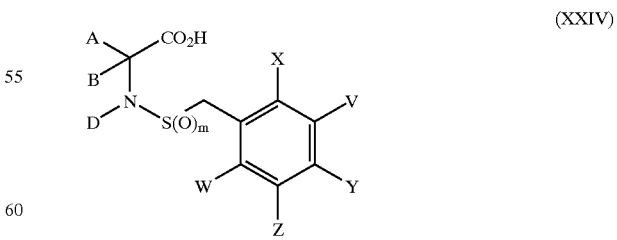

(XXIV)

in which

A, B, D, V, W, X, Y, Z and m are each as defined above are novel.

The compounds of the formula (XXIV) are obtained when amino acids of the formula (XXV):

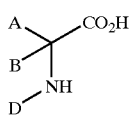
(XXV)

in which
A, B and D are each as defined above
are acylated with substituted benzyl-S(O)$_m$ halides of the formula (XXIII):

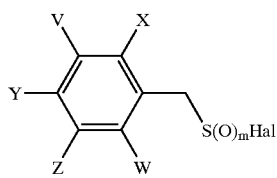
(XXIII)

in which
V, W, X, Y, Z and m are each as defined above and
Hal represents chlorine or bromine, in particular chlorine, for example according to Schotten-Baumann (Organikum, VEB Deutscher Verlag der Wissenschaften, Berlin 1977, p. 505).

Some of the compounds of the formula (XXIII) are novel. They can be prepared by processes known in principle.

The compounds of the formula (XXIII) in which V, W, X, Y and Z are as defined above and m represents the number 2 are obtained, for example, by converting substituted benzyl halides of the formula (XXXIII):

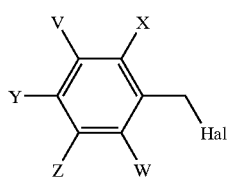
(XXXIII)

in which
V, W, X, Y and Z are each as defined above and
Hal represents chlorine or bromine
with thiourea into the isothiuronium salts of the formula (XXVI-A):

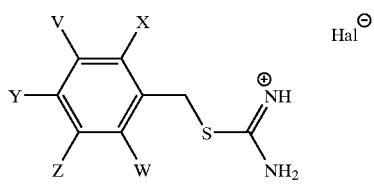
(XXVI-A)

in which
V, W, X, Y and Z are each as defined above and
Hal represents chlorine or bromine
and cleaving them oxidatively using chlorine (B. Johnson, J. M. Sprague, J. Am. Chem. Soc. 58, 1348 (1936)) or by converting benzyl halides of the formula (XXXIII) with sodium sulphite into the sodium salts of the corresponding benzylsulphonic acids of the formula (XXVI-B):

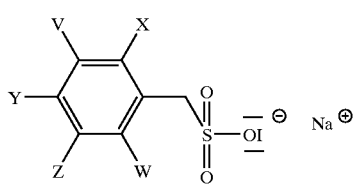
(XXVI-B)

in which
V, W, X, Y and Z are each as defined above
and reacting these with phosphorus pentachloride (W. V. Farrar, J. Chem. Soc. 1960, 3063; Ruggli, Helv. Chim. Acta 14 (1931), 541).

Some of the compounds of the formulae (XXIII) and (XXVI) are known, and/or they can be prepared by known processes (see, for example, Compagnon, Miocque Ann. Chim. (Paris) [14] 5, pp. 11–22, 23–27 (1970)).

The substituted cyclic aminocarboxylic acids of the formula (XXII) in which A and B form a ring are, in general, obtainable by the Bucherer-Bergs synthesis or by the Strecker synthesis, and they are in each case obtained in different isomeric forms. Thus, under the conditions of the Bucherer-Bergs synthesis, what is obtained are predominantly those isomers (hereinbelow for the sake of simplicity referred to as β) in which the radicals R and the carboxyl group are in an equatorial position, whereas the conditions of the Strecker synthesis yield predominantly those isomers (hereinbelow for the sake of simplicity referred to as α) where the amino group and the radicals R are in an equatorial position.

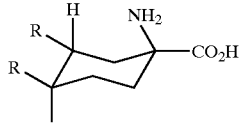
(β isomer)

Bucherer-Bergs synthesis

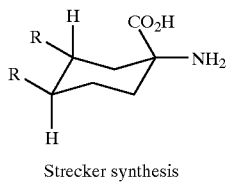
(α isomer)

Strecker synthesis (L. Munday, J. Chem. Soc. 4372 (1961); J. T. Eward, C. Jitrangeri, Can. J. Chem. 53, 3339 (1975).

Furthermore, the starting materials of the formula (II):

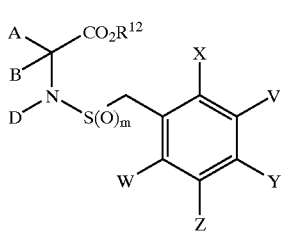
(II)

in which

A, B, D, V, W, X, Y, Z, $R^{12}$ and m are each as defined above and which are used for the process (A) above can be prepared by converting aminonitriles of the formula (XXVII):

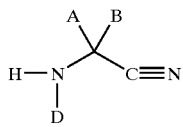
(XXVII)

in which

A, B and D are each as defined above with substituted benzyl-S(O)$_m$ halides of the formula (XXIII):

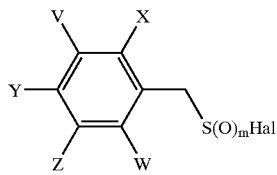
(XXIII)

in which

V, W, X, Y, Z, m and Hal are each as defined above into compounds of the formula (XXVIII):

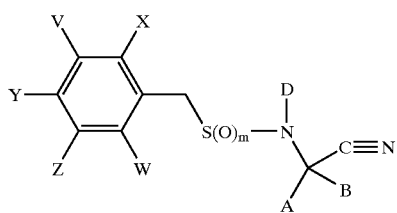
(XXVIII)

in which

A, B, D, V, W, X, Y, Z and m are each as defined above, and then subjecting these to an acidic alcoholysis.

The compounds of the formula (XXVIII) are likewise novel.

The compounds of the formula (III):

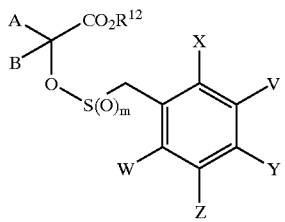
(III)

in which

A, B, V, W, X, Y, Z, $R^{12}$ and m are each as defined above and which are required as starting materials for the process (B) according to the invention are novel.

They can be prepared by methods known in principle. Thus, the compounds of the formula (III) are obtained, for example, when 2-hydroxycarboxylic esters of the formula (XXIX):

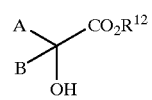
(XXIX)

in which

A, B and $R^{12}$ are each as defined above are reacted with substituted benzyl-S(O)$_m$ halides of the formula (XXIII):

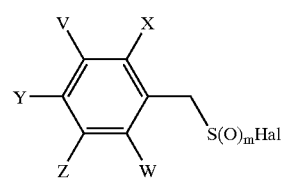
(XXIII)

in which

V, W, X, Y, Z, m and Hal are each as defined above (H.-D. Stachel, G. Drasch, Arch. Pharm. 318, 304 (1985)).

The compounds of the formula (IV):

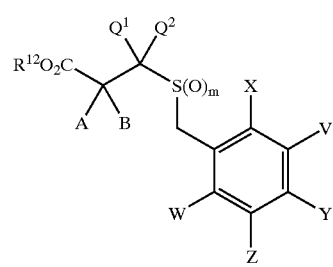
(IV)

in which

A, B, $Q^1$, $Q^2$, V, W, X, Y, Z, m and $R^{12}$ are each as defined above and which are required as starting materials for the process (C) above are novel.

They can be prepared by methods known in principle.

The 5-aryl-S(O)$_m$-carboxylic esters of the formula (IV) are obtained, for example, when 5-aryl-S(O)$_m$-carboxylic acids of the formula (XXX):

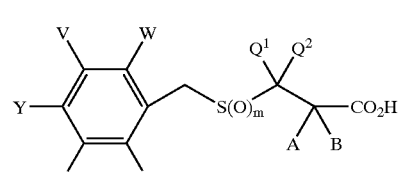
(XXX)

in which

V, W, X, Y, Z, A, B, $Q^1$, $Q^2$ and m are each as defined above are esterified (cf. J. G. Rombardino, E. H. Wiseman, 13, 206 (1970); A. Abdel-Wahab et al., Phosphorus, Sulfur and Silicon 59, 149 (1991))

(see also the Preparation Examples).

Furthermore, compounds of the formula (IV):

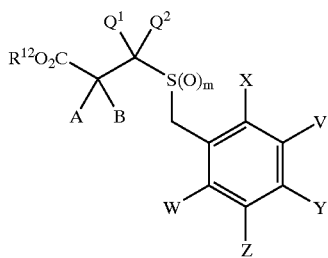

(IV)

in which

A, B, $Q^1$, $Q^2$, V, W, X, Y, Z and $R^{12}$ are each as defined above and m represents the numbers 1 and 2 are obtained when benzyl thioethers of the formula (XXXI):

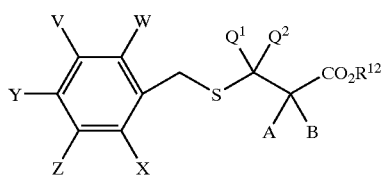

(XXXI)

in which

A, B, $Q^1$, $Q^2$, V, W, X, Y, Z and $R^{12}$ are each as defined above are oxidized using oxidizing agents such as, for example, peracids, hydrogen peroxide, peroxides or chlorine (see Preparation Examples).

Some of the compounds of the formula (XXXI) are novel, and they can be prepared by processes known per se.

Thus, for example, compounds of the formula (XXXI):

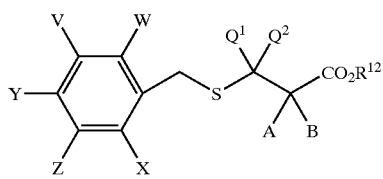

(XXXI)

in which

A, B, $Q^1$, $Q^2$, V, W, X, Y, Z and $R^{12}$ are each as defined above are obtained when mercapto compounds of the formula (XXXII):

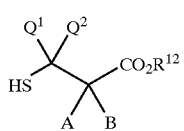

(XXXII)

in which

A, B, $Q^1$, $Q^2$ and $R^{12}$ are each as defined above are reacted with benzyl halides of the formula (XXXIII):

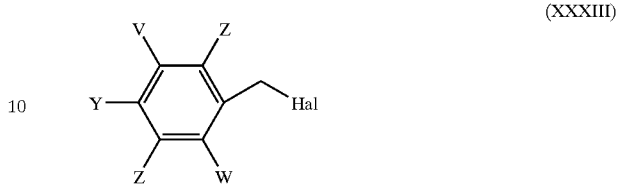

(XXXIII)

in which

V, W, X, Y and Z are each as defined above and

Hal represents chlorine or bromine in the presence of an acid binder and in the presence of a solvent (see Preparation Examples, variant 1).

Compounds of the formula (XXXI):

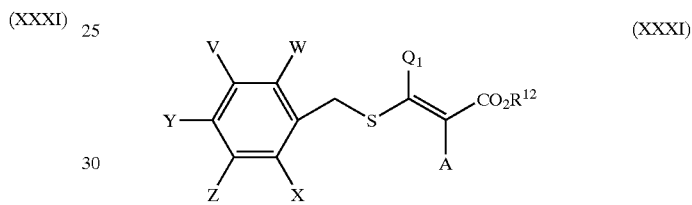

(XXXI)

in which

A, $Q^1$, V, W, X, Y, Z and $R^{12}$ are each as defined above are obtained when compounds of the formula (a):

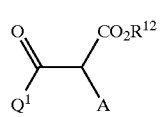

(a)

in which

A, $Q^1$ and $R^{12}$ are each as defined above are reacted with compounds of the formula (b):

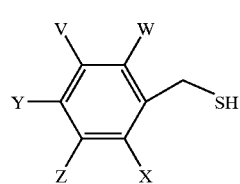

(b)

in which

V, W, X, Y and Z are each as defined above in the presence of an acid and a solvent (see Preparation Examples, variant 2).

The compounds of the formula (V):

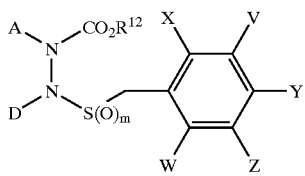
(V)

in which

A, D, V, W, X, Y, Z, m and $R^{12}$ are each as defined above and which are required as starting materials for the process (D) according to the invention are novel.

The hydroxides of the formula (V) are obtained, for example, when carbamates of the formula (XXXIV):

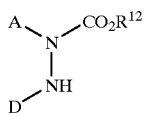
(XXXIV)

in which

A and D are each as defined above are reacted with substituted benzyl-$S(O)_m$ halides of the formula (XXIII):

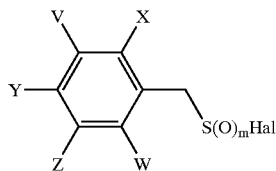
(XXIII)

in which

V, W, X, Y, Z, m and Hal are each as defined above.

The compounds of the formula (XVIII):

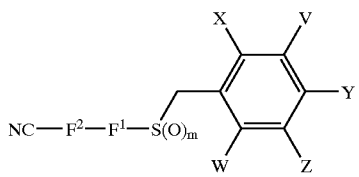
(XVIII)

in which

V, W, X, Y, Z and m are each as defined above and $F^1$ and $F^2$ represent the groups

—$F^1$—$F^2$—

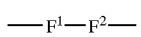
(1')

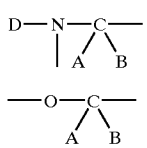
(2')

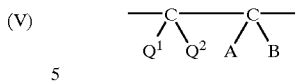
(3')

in which the radicals A, B, D, $Q^1$ and $Q^2$ are each as defined above, which compounds are required as starting materials for the process M (β) according to the invention, are novel.

The nitriles of the formula (XVIII) are obtained when, for the group (1'), for example, aminonitriles of the formula (XXVII):

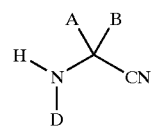
(XXVII)

in which

A, B and D are each as defined above are reacted with substituted benzyl-$S(O)_m$ halides of the formula (XXIII):

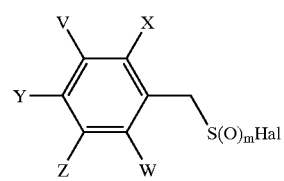
(XXIII)

in which

V, W, X, Y, Z, m and Hal are each as defined above (S. T. Ingate, Tetrahedron 53, 17795 (1997)).

Analogously, nitriles of the formula (XVIII) for the group (2') are obtained when, for example, cyanohydrines of the formula (XXXV):

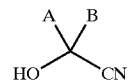
(XXXV)

in which

A and B are each as defined above are reacted with substituted benzyl-$S(O)_m$ halides of the formula (XXIII) in which V, W, X, Y, Z, m and Hal are each as defined above (S. T. Ingate, Tetrahedron 53, 17795 (1997)).

Furthermore, compounds of the formula (XVIII) for the group (3'):

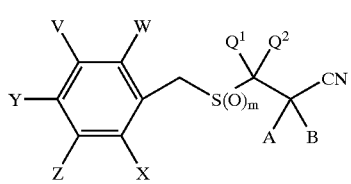
(XVIII-3')

in which

A, B, $Q^1$, $Q^2$, V, W, X, Y and Z are each as defined above and m represents the numbers 1 and 2 are obtained when benzyl thioethers of the formula (XXXVI):

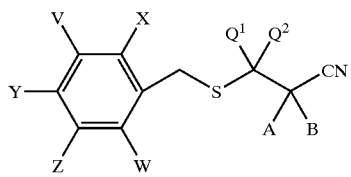
(XXXVI)

in which

A, B, $Q^1$, $Q^2$, V, W, X, Y and Z are each as defined above are oxidized using oxidizing agents such as, for example, peracids, hydrogen peroxide, peroxides or chlorine (see Preparation Examples, J. R. Beck, J. Heterocyclic Chem. 15, 513 (1978)).

Some of the compounds of the formula (XXXVI) are novel, and they can be prepared by known processes.

Thus, for example, compounds of the formula (XXXVI):

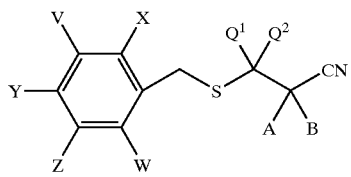
(XXXVI)

in which

A, B, $Q^1$, $Q^2$, V, W, X, Y and Z are each as defined above are obtained when mercaptocyano compounds of the formula (XXXVII):

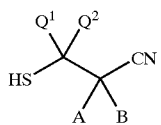
(XXXVII)

in which

A, B, $Q^1$, $Q^2$ and $R^{12}$ are each as defined above are reacted with benzyl halides of the formula (XXXIII):

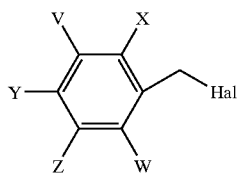
(XXXIII)

in which

V, W, X, Y and Z are each as defined above and

Hal represents chlorine or bromine in the presence of an acid binder and in the presence of a solvent, or according to the process described by J. R. Beck, J. Heterocyclic Chem. 15, 513 (1978), or according to the Preparation Examples.

The acid halides of the formulae (VI) and (XIX), carboxylic anhydrides of the formulae (VII) and (XX), chloroformic esters or chloroformic thioesters of the formula (VIII), chloromonothioformic esters or chlorodithioformic esters of the formula (IX), sulphonyl chlorides of the formula (X), phosphorus compounds of the formula (XI) and metal hydroxides, metal alkoxides or amines of the formulae (XII) and (XIII) and isocyanates of the formula (XIV) and carbamoyl chlorides of the formula (XV), alkylating agents of the formula (XVI) and amines of the general formula (XVII) which are furthermore required as starting materials for carrying out the processes (E), (F), (G), (H), (I), (J), (K), (L), (M), (N) and (O) according to the invention are generally known compounds of organic or inorganic chemistry.

The process (A) is characterized in that compounds of the formula (II) in which A, B, D, V, W, X, Y, Z, m and $R^{12}$ are each as defined above are subjected to an intramolecular condensation in the presence of a base.

Diluents which are suitable for use in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methyl-pyrrolidine, and also alcohols, such as methanol, ethanol, propanol, iso-propanol, butanol, iso-butanol and tert-butanol.

Bases (deprotonating agents) which are suitable for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl ($C_8$–$C_{10}$)ammonium chloride) or TDA 1 (=tris-(methoxyethoxyethyl)-amine). It is furthermore possible to use alkali metals, such as sodium or potassium. Moreover, use can be made of alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide. It is furthermore possible to use, for example, tertiary amines, such as triethylamine, pyridine, diazabicyclooctane (DABCO), diazabicycloundecene (DBU), diazabicyclononene (DBN) and Hünig base.

When carrying out the process (A) according to the invention, the reaction temperatures can be varied within a relatively wide range. In general, the process is carried out at temperatures between 0° C. and 250° C., preferably between 20° C. and 150° C.

The process (A) according to the invention is generally carried out under atmospheric pressure.

When carrying out the process (A) according to the invention, the reaction components of the formula (II) and the deprotonating bases are generally employed in twice the equimolar amount. However, it is also possible to use a relatively large excess (up to 3 mol) of one or the other component.

The process (B) is characterized in that compounds of the formula (III) in which A, B, V, W, X, Y, Z, m and $R^{12}$ are each as defined above are subjected to an intramolecular condensation in the presence of a diluent and in the presence of a base.

Diluents suitable for use in the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. It is furthermore possible to use alcohols, such as methanol, ethanol, propanol, iso-propanol, butanol, iso-butanol and tert-butanol.

Bases (deprotonating agents) suitable for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl $(C_8-C_{10})$ammonium chloride) or TDA 1 (=tris-(methoxyethoxy-ethyl)-amine). Furthermore, it is possible to use alkali metals, such as sodium or potassium. Moreover, is it possible to use alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide. It is furthermore possible to use, for example, tertiary amines, such as triethylamine, pyridine, DABCO, DBU, DBN and Hünig base.

When carrying out the process (B) according to the invention, the reaction temperatures can be varied within a relatively wide range. In general, the process is carried out at temperatures between 0° C. and 250° C., preferably between 20° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one or the other component.

The process (C) is characterized in that compounds of the formula (IV) in which A, B, $Q^1$, $Q^2$, V, W, X, Y, Z, m and $R^{12}$ are each as defined above are subjected to an intramolecular condensation in the presence of a base.

Diluents suitable for use in the process (C) according to the invention are all organic solvents which are inert to the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methyl-pyrrolidone. It is furthermore possible to use alcohols, such as methanol, ethanol, propanol, iso-propanol, butanol, isobutanol, tert-butanol.

Suitable bases (deprotonating agents) for carrying out the process (C) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (methyltrialkyl $(C_8-C_{10})$ammonium chloride) or TDA 1 (tris-(methoxyethoxyethyl)-amine). It is furthermore possible to use alkali metals, such as sodium or potassium. Moreover, it is possible to use alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide. It is furthermore possible to use tert-amines, such as, for example, triethylamine, pyridine, DABCO, DBU, DBN and Hünig base.

When carrying out the process (C) according to the invention, the reaction temperatures can be varied within a relatively wide range. In general, the process is carried out at temperatures between −75° C. and 250° C., preferably between 0° C. and 150° C.

The process (C) according to the invention is generally carried out under atmospheric pressure.

When carrying out the process (C) according to the invention, the reaction components of the formula (IV) and the deprotonating bases are generally employed in approximately equimolar amounts. However, it is also possible to use a relatively large excess (up to 3 mol) of one or the other component.

The process (D) is characterized in that compounds of the formula (V) in which A, D, V, W, X, Y, Z, m and $R^{12}$ are each as defined above are subject to an intramolecular condensation in the presence of bases.

Diluents suitable for use in the process (D) according to the invention are all organic solvents which are inert to the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methyl-pyrrolidone. It is furthermore possible to use alcohols, such as methanol, ethanol, propanol, iso-propanol, butanol, isobutanol, tert-butanol.

Bases (deprotonating agents) suitable for carrying out the process (D) according to the invention are all customary proton acceptors.

Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (methyltrialkyl($C_8$–$C_{10}$)ammonium chloride) or TDA 1 (tris-(methoxyethoxyethyl)-amine). It is furthermore possible to use alkali metals, such as sodium or potassium. Moreover, it is possible to use alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide. It is furthermore possible to use, for example, tert-amines, such as triethylamine, pyridine, DABCO, DBU, DBN and Hünig base.

When carrying out the process (D) according to the invention, the reaction temperatures can be varied within a relatively wide range. In general, the process is carried out at temperatures between 0° C. and 250° C., preferably between 50° C. and 150° C.

The process (D) according to the invention is generally carried out under atmospheric pressure.

When carrying out the process (D) according to the invention, the reaction components of the formula (V) and the deprotonating bases are generally employed in approximately equimolar amounts. However, it is also possible to use a relatively large excess (up to 3 mol) of one or the other component.

The process (E-α) is characterized in that compounds of the formulae (I-1-a) to (I-4-a) are in each case reacted with carbonyl halides of the formula (VI), if appropriate in the presence of a diluent and if appropriate in the presence of an acid binder.

Diluents suitable for use in the process (E-α) according to the invention are all solvents which are inert to the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acid halide permitting, the reaction can also be carried out in the presence of water.

Suitable acid binders for the reaction by the process (E-α) according to the invention are all customary acid acceptors. Preference is given to using tertiary amines, such as triethylamine, pyridine, N,N-dimethylaminopyridine (DMAP), diazabicyclooctane (DABCO), diazabicycloundecene (DBU), diazabicyclononene (DBN), Hünig base and N,N-dimethyl-aniline, furthermore alkali earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

When carrying out the process (E-α) according to the invention, the reaction temperatures can be varied within a relatively wide range. In general, the process is carried out at temperatures between −20° C. and +150° C., preferably between 0° C. and 100° C.

When carrying out the process (E-α) according to the invention, the starting materials of the formulae (I-1-a) to (I-4-a) and the carbonyl halide of the formula (VI) are generally each employed in approximately equivalent amounts. However, it is also possible to use a relatively large excess (up to 5 mol) of the carbonyl halide. Work-up is carried out by customary methods.

The process (E-β) is characterized in that compounds of the formulae (I-1-a) to (I-4-a) are reacted with carboxylic anhydrides of the formula (VII), if appropriate in the presence of a diluent and if appropriate in the presence of an acid binder.

Diluents which can be used in the process (E-β) are preferably those diluents which are also preferred when using acid halides. Otherwise, it is also possible for carboxylic anhydride employed in excess to act simultaneously as diluent.

Preferred acid binders which are added, if appropriate, in the process (E-β) are those acid binders which are also preferred when using acid halides.

When carrying out the process (E-β) according to the invention, the reaction temperatures can be varied within a relatively wide range. In general, the process is carried out at temperatures between −20° C. and +150° C., preferably between 0° C. and 100° C.

When carrying out the process (E-β) according to the invention, the starting materials of the formulae (I-1-a) to (I-4-a) and the carboxylic anhydride of the formula (VII) are generally each employed in approximately equivalent amounts. However, it is also possible to use a relatively large excess (up to 5 mol) of carboxylic anhydride. Work-up is carried out by customary methods.

In general, the diluent and excess carboxylic anhydride and the carboxylic acid that is formed are removed by distillation or by washing with an organic solvent or with water.

The process (F) is characterized in that compounds of the formulae (I-1-a) to (I-4-a) are in each case reacted with chloroformic esters or chloroformic thiolesters of the formula (VIII), if appropriate in the presence of a diluent and if appropriate in the presence of an acid binder.

Suitable acid binders for the reaction according to the process (F) according to the invention are all customary acid acceptors. Preference is given to using tertiary amines, such as triethylamine, pyridine, DABCO, DBU, DBN, Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Diluents suitable for use in the process (F) according to the invention are all solvents which are inert to the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, and additionally carboxylic esters, such as ethyl acetate, and also strongly polar solvents, such as dimethyl sulphoxide and sulpholane.

When carrying out the process (F) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (F) according to the invention is generally carried out under atmospheric pressure.

When carrying out the process (F) according to the invention, the starting materials of the formulae (I-1-a) to (I-4-a) and the appropriate chloroformic ester or chloroformic thioester of the formula (VI) are generally each employed in approximately equivalent amounts. However, it is also possible to use a relatively large excess (up to 2 mol) of one or the other component. Work-up is carried out by customary methods. In general, precipitated salts are removed and the reaction mixture that remains is concentrated by stripping off the diluent.

The process (G) according to the invention is characterized in that compounds of the formulae (I-1-a) to (I-4-a) are in each case reacted with compounds of the formula (IX) in the presence of a diluent and, if appropriate, in the presence of an acid binder.

In the preparation process (G), about 1 mol of chloromonothioformic ester or chlorodithioformic ester of the formula (IX) is employed per mole of the starting material of the formulae (I-1-a) to (I-4-a), at from 0 to 120° C., preferably from 20 to 60° C.

Suitable diluents which are added, if appropriate, are all inert polar organic solvents, such as ethers, esters, amides, sulphones, sulphoxides, and also halogenated alkanes.

Preference is given to using dimethylsulphoxide, ethyl acetate, tetrahydrofuran, dimethylformamide or methylene chloride.

If, in a preferred embodiment, the enolate salt of the compounds (I-1-a) to (I-4-a) is prepared by addition of strong deprotonating agents, such as, for example, sodium hydride or potassium tertiary-butoxide, the addition of further acid binders can be dispensed with.

If acid binders are used, these are customary inorganic or organic bases, sodium hydroxide, sodium carbonate, potassium carbonate, pyridine and triethylamine being mentioned by way of example.

The reaction can be carried out under atmospheric pressure or under elevated pressure and is preferably carried out under atmospheric pressure. Work-up is carried out by customary methods.

The process (H) according to the invention is characterized in that compounds of the formulae (I-1-a) to (I-4-a) are in each case reacted with sulphonyl chlorides of the formula (X), if appropriate in the presence of a diluent and if appropriate in the presence of an acid binder.

In the preparation process (H), about 1 mol of sulphonyl chloride of the formula (X) is employed per mole of the starting material of the formula (I-1-a) to (I-8-a), at from −20 to 150° C., preferably from 20 to 70° C.

Suitable diluents which are added, if appropriate, are all inert polar organic solvents, such as ethers, amides, nitrites, sulphones, sulphoxides or halogenated hydrocarbons, such as methylene chloride.

Preference is given to using dimethyl sulphoxide, tetrahydrofuran, dimethyl-formamide, methylene chloride.

If, in a preferred embodiment, the enolate salt of the compounds (I-1-a) to (I-4-a) is prepared by addition of strong deprotonating agents (such as, for example, sodium hydride or potassium tertiary-butoxide), the addition of further acid binders can be dispensed with.

If acid binders are used, these are customary inorganic or organic bases, sodium hydroxide, sodium carbonate, potassium carbonate, pyridine and triethylamine being mentioned by way of example.

The reaction can be carried out under atmospheric pressure or under elevated pressure and is preferably carried out under atmospheric pressure. Work-up is carried out by customary methods.

The process (I) according to the invention is characterized in that compounds of the formulae (I-1-a) to (I-4-a) are in each case reacted with phosphorus compounds of the formula (XI), if appropriate in the presence of a diluent and if appropriate in the presence of an acid binder.

In the preparation process (I), to obtain compounds of the formulae (I-1-e) to (I-4-e), from 1 to 2, preferably from 1 to 1.3, mol of the phosphorus compound of the formula (XI) are employed per mole of the compounds (I-1-a) to (I-4-a), at temperatures between −40° C. and 150° C., preferably between −10 and 110° C.

Suitable diluents which are added, if appropriate, are all inert polar organic solvents, such as ethers, esters, amides, nitrites, alcohols, sulphides, sulphones, sulphoxides, etc.

Preference is given to using acetonitrile, dimethyl sulphoxide, ethyl acetate, tetrahydrofuran, dimethylformamide, methylene chloride.

Acid binders, which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out under atmospheric pressure or under elevated pressure and is preferably carried out under atmospheric pressure. Work-up is carried out by customary methods of organic chemistry. Purification of the end products obtained is preferably carried out by crystallization, chromatographic purification or so-called "incipient distillation", i.e. removal of the volatile components under reduced pressure.

The process (J) is characterized in that compounds of the formulae (I-1-a) to (I-4-a) are reacted with metal hydroxides or metal alkoxides of the formula (XII) or amines of the formula (XIII), if appropriate in the presence of a diluent.

Preferred diluents for use in the process (J) according to the invention are ethers, such as tetrahydrofuran, dioxane, diethyl ether, or else alcohols, such as methanol, ethanol, isopropanol, and also water.

The process (J) according to the invention is generally carried out under atmospheric pressure.

The reaction temperatures are generally between −20° C. and 100° C., preferably between 0° C. and 50° C.

The process (K) according to the invention is characterized in that compounds of the formulae (I-1-a) to (I-4-a) are in each case reacted with (K-α) compounds of the formula (XIV), if appropriate in the presence of a diluent and if appropriate in the presence of a catalyst, or (K-β) with compounds of the formula (XV), if appropriate in the presence of a diluent and if appropriate in the presence of an acid binder.

In the preparation process (K-α), about 1 mol of isocyanate of the formula (XIV) is employed per mole of the starting of the formulae (I-1-a) to (I-4-a), at from 0 to 100° C., preferably from 20 to 50° C.

Suitable diluents which are added, if appropriate, are all inert organic solvents, such as ethers, amides, nitrites, sulphones, sulphoxides.

If appropriate, catalysts may be added to accelerate the reaction. Particularly advantageous catalysts are organotin compounds, such as, for example, dibutyltin dilaurate. The process is preferably carried out under atmospheric pressure.

In the preparation process (K-β), about 1 mol of carbamoyl chloride or thiocarbamoyl chloride of the formula (XV) is employed per mole of the starting material of the formulae (I-1-a) to (I-4-a), at from −20 to 150° C., preferably from 0 to 70° C.

Suitable diluents which are added, if appropriate, are all inert polar organic solvents, such as ethers, esters, amides, sulphones, sulphoxides or halogenated hydrocarbons.

Preference is given to using dimethyl sulphoxide, tetrahydrofuran, ethyl acetate, dimethylformamide or methylene chloride.

If, in a preferred embodiment, the enolate salt of the compound (I-1-a) to (I-4-a) is prepared by addition of strong deprotonating agents (such as, for example, sodium hydride or potassium tertiary-butoxide), the addition of further acid binders can be dispensed with.

If acid binders are used, these are customary inorganic or organic bases, sodium hydroxide, sodium carbonate, potassium carbonate, triethylamine or pyridine being mentioned by way of example.

The reaction can be carried out under atmospheric pressure or under elevated pressure and is preferably carried out under atmospheric pressure. Work-up is carried out by customary methods.

The process (L) according to the invention is characterized in that compounds of the formulae (I-1-a) to (I-4-a) are in each case reacted with alkylating agents of the formula (XVI), if appropriate in the presence of a diluent and if appropriate in the presence of an acid binder.

Suitable diluents for carrying out the process (L) according to the invention for preparing the compounds according to the invention are inert organic solvents. Preference is given to using aliphatic, alicyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzen, ethers, such as diethyl ether, diisopropyl ether, dioxane, tetrahydrofuran or ethylene glycol diethyl ether or ethylene glycol dimethyl ether, ketones, such as acetone butanone, methyl isopropyl ketone or methyl isobutyl ketone, esters, such as ethyl acetate, acids, such as acetic acid, nitriles, such as acetonitrile or propionitrile, amides, such as dimethylformamide, dimethylacetamide, N-methylpyrrolidone or hexamethylphosphoric triamide. If compounds of the formula (XVI) in liquid form are employed as reactants, it is also possible to use them, in an appropriate excess, simultaneously as diluents.

Suitable acid binders are all inorganic or organic bases which are customarily used. Preference is given to using alkali metal hydrides, hydroxides, amides, carbonates or bicarbonates, such as, for example, sodium hydride, sodium amide, sodium hydroxide, potassium carbonate or sodium bicarbonate, or else tertiary amines, such as, for example, triethylamine, N,N-dimethylaniline, pyridine, 4-(N,N-dimethylmino)-pyridine, diazabicyclooctane (DABCO), diazabicyclononene (DBU) or Hünig base.

When carrying out the process, the reaction temperatures can be varied within a relatively wide range. In general, the process is carried out at between −20° C. and +200° C., preferably between 0° C. and +1500° C.

For carrying out the process (L) according to the invention for preparing the compounds according to the invention, generally in each case from 1 to 20 mol, preferably in each case from 1 to 5 mol, of alkylating agent of the formula (XVI) and, if appropriate, from 1 to 5 mol, preferably from 1 to 2 mol, of acid binder are employed per mole of the compounds of the formulae (I-1-a) to (I-4-a). The practice of the reaction and the work-up and isolation of the reaction products are carried out by customary methods (cf. also the Preparation Examples).

The process (M-α) is characterized in that compounds of the formulae (I-1-a) to (I-4-a) are in each case reacted with amines of the formula (XVII), if appropriate in the presence of a diluent and if appropriate in the presence of an acid catalyst and a dehydrating agent.

Preferred diluents for carrying out the process (M-α) according to the invention are inert organic solvents. These include, in particular, aliphatic, alicyclic or aromatic, optionally halogenated hydrocarbons, such as, for example, benzine, ligroin, benzene, toluene, xylene, chlorobenzene, petroleum ether, pentane, hexane, heptane, cyclohexane, dichloromethane, chloroform, carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or esters, such as ethyl acetate. The amines of the formula (XVII), in liquid form and in an appropriate excess, can also be used as solvents.

When carrying out the process (M-α) according to the invention, the reaction temperatures can be varied within a relatively wide range, in general, the process is carried out at temperatures between 0° C. and 250° C. preferably at temperatures between 20° C. and 200° C.

The process (M-α) according to the invention is usually carried out under atmospheric pressure. The process (M-α) according to the invention can be earned out under elevated pressure.

For carrying out the process (M-α) according to the invention, in general from 1 to 20 mol, preferably from 1 to 5 mol, of amine of the formula (XVII) and, if appropriate, from 1 to 3 mol of dehydrating agent are employed per mole of the compounds of die formulae (I-1-a) to (I-4-a). The practice of the reaction and the work-up and isolation of the reaction products are carried out analogously to generally known processes.

Suitable acids for the process (M-α) are organic acids, such as, for example, acetic acid, trifluoroacetic acid or p-toluenesulphonic acid.

Suitable dehydrating agents for the process (M-α) are customary drying agents, such as, for example, sodium sulphate, magnesium sulphate or calcium chloride, and also molecular sieves. Moreover, the water of reaction that is formed can be removed as an azeotrope by distillation.

The process (M-β) according to the invention for preparing the compounds of the formulae (I-1-i) to (I-4-i) is characterized in that compounds of the formula (XVIII) are subjected to intramolecular condensation in the presence of bases.

Diluents suitable for use in the process according to the invention for preparing the compounds of the formulae (I-1-i) to (I-4-i) are all customary inert organic solvents. Preference is given to using hydrocarbons, such as toluene and xylene, furthermore ethers, such as dibuzyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methyl-pyrrolidone.

Deprotonating agents which can be used for carrying out the process (M-β) according to the invention for preparing the compounds of the formulae (I-1-i) to (I-4-i) are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium chloride or tetrabutylammonium hydrogen sulphate, Adogen 464[1] or TDA 1[2]. It is furthermore possible to use alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide.

[1] Adogen 464=methyltrialkyl($C_8$–$C_{10}$)ammonium chloride
[2] TDA 1=tris-(methoxyethoxyethyl)-amine When carrying Out the process (M-β) according to the invention for preparing the compounds of the formulae (I-1-i) to (I-4-i), the reaction temperatures can be varied within a relatively wide range. In general, the process is carried out at temperatures between −20° C. and 250° C. preferably between 0° C. and 150° C.

The process according to the invention is generally carried out under atmospheric pressure.

When carrying our the process (M-β) according to the invention for preparing the compounds of the formulae (I-1-i) to (I-4-i), the reaction components of the formula (XVIII) and the deprotonating bases are generally employed in approximately equimolar amounts. However, it is also possible to employ a relatively large excess (up to 5 mol) of one or the other component.

The process (N-α) is characterized in that compounds of the formulae (1-1-i$^1$) to (I-4-i$^1$) are reacted with acid halides of the formula (XIX). Diluents suitable for use in the process (N-α) according to the invention when using the acid halides are all solvents which are inert to these compounds. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, nitriles, such as acetonitrile, and additionally solvents, such as dimethyl sulphoxide and sulpholane.

If acid binders are used in the reaction of the process (N-α) according to the invention, these can be all customary acid acceptors. Preference is given to using tertiary amines, such as triethylamine, pyridine, 4-N,N-dimethylaminopyridine (DMAP), diazabicyclooctane (DABCO), diazabicycloundecene (DBU), diazabicyclononene (DBN), Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, but also metal hydrides, such as sodium hydride.

In the process (N-α) according to the invention, even when using acid halides, the reaction temperatures can be varied within a relatively wide range. In general, the process is carried out at temperatures between −20° C. and +250° C., preferably between 0° C. and 150° C.

When carrying out the process (N-α) according to the invention, the starting materials of the formulae (I-1-i$^1$) to (I-4-i$^1$) and the acid halide of the formula (XIX) are generally employed in approximately equivalent amounts. However, it is also possible to employ a relatively large excess (up to 5 mol) of the acid chloride. Work-up is carried out by customary methods.

The process (N-β) is characterized in that compounds of the formulae (I-1-i$^1$) to (I-4-i$^1$)) are reacted with carboxylic anhydrides of the formula (XX).

If, in the process (N-β) according to the invention, carboxylic anhydrides are used as reaction components of the formula (XX), the diluents used are preferably those diluents which are also preferably used when employing acid halides. Otherwise, it is also possible for excess carboxylic anhydride to act simultaneously as diluent. Preferred acid binders are the bases which are also preferably used when employing acid chlorides.

In the process (N-β) according to the invention, even when using carboxylic anhydrides, the reaction temperatures can be varied within a relatively wide range. In general, the processes are carried out at temperatures between −20° C. and +250° C., preferably between 0° C. and 150° C.

When carrying out the process according to the invention, the starting materials of the formulae (I-1-i$^1$) to (I-4-i$^1$) and the carboxylic anhydride of the formula (XX) are generally employed in approximately equivalent amounts. However, it is also possible to employ a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

Furthermore, in the process (N), it is also possible to use mixtures of acid chlorides of the formula (XIX) and carboxylic anhydrides of the formula (XX).

The process (N-γ) is characterized in that compounds of the formulae (I-1-a$^1$) to (I-4-a$^1$) are in each case reacted with orthoformic esters of the formula (XXI), in inert solvents. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, furthermore ethers, such as diethyl ether, tetrahydrofuran and dioxane, and also strongly polar solvents, such as dimethyl sulphoxide and sulpholane.

In the process (N-γ) according to the invention, the reaction temperatures can be vaned within a relatively wide range. In general, the process is earned out at temperatures between −20° C. and +250° C., preferably between 0° C. and 150° C.

When carrying out the process (N-γ) according to the invention, the starting materials of the formulae (I-1-i$^1$) to (I-4-i$^1$) and the orthoformic, ester of the formula (XXI) are generally each employed in approximately equivalent amounts. However, it is also possible to use the orthoformic ester in a relatively large excess (up to 5 mol) or even as solvent. Work-up is carried out by customary methods.

The process (O) is characterized in that compounds of the formulae (I-1-i$^2$) to (I-4-i$^2$) are in each case reacted with carbonyl halides of the formula (XIX), if appropriate in the presence of a diluent and if appropriate in the presence of an acid binder.

Diluents suitable for use in the process (O) according to the invention are all solvents which are inert to the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acid halide permitting, the reaction can also be carried out in the presence of water.

Suitable acid binders for the reaction by the process (O) according to the invention are all customary acid acceptors. Preference is given to using tertiary amines, such as triethylamine, pyridine, N,N-dimethylaminopyridine (DMAP), diazabicyclooctane (DABCO), diazabicycloundecene (DBU), diazabicyclononene (DBN), Hünig base anti N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also, alkali metal hydroxides, such as sodium hydroxide and potassium hydroxide, but also metal hydrides, such as sodium hydride.

In the process (O) according to the invention, the reaction temperatures can be varied within a relatively wide range. In general, the process is carried out at temperatures between −20° C. and +150° C., preferably between 0° C. and 100° C.

When carrying out the process (O) according to the invention, the starting materials of the formulae (I-1-i$^2$) to (I-4-i$^2$) and the carbonyl halide of the formula (XIX) are generally each employed in approximately equivalent amounts. However, it is also possible to employ a relatively large excess (up to 5 mol) of the carbonyl halide. Work-up is carried out by customary methods.

The active compounds are suitable for controlling animal pests, in particular insects, arachnids and nematodes, which are encountered in agriculture, in forests, in the protection of stored products and of materials, and in the hygiene sector, and have good plant tolerance and favourable toxicity to warm-blooded animals. They may be preferably employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Osrhoptera, for example, *Onychiurus armatus.*

From the order of the Orthoptera, for example, *Acheta domestucus, Gryllotalpa* spp.*, Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthirapters, for example, *Pediculus humanus corporis, Haematipinus* spp.*, Linognathus* spp.*, Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp.*, Dysdercus intermedius, Piesma quadrata, Cimex lectularuis, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp.*, Macrosiphum avenae, Myzus* spp.*, Phorodon humuli, Rhopalosiphum padi, Empoasca* spp.*, Euscelis bilobatus, Nephotettix cincticeps, Lecanium corni, Saissetia oleae, Laodelphax striatellus, Nilaparvata lugens, Aonidiella aurantii, Aspidotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp.*, Bucculatrix thurberiella, Phyllocnistis citrella, Agrotis* spp.*, Euxoa* spp.*, Feltia* spp.*, Earias insulana, Heliothis* spp.*, Mamestra brassicae, Panolis flammea, Spodoptera* spp.*, Trichoplusia ni, Carpocapsa pomonella, Pieris* spp.*, Chilo* spp.*, Pyrausta nubilalis, Ephestia kuehniella, Galleria mellonella, Tineola bisselliella, Tinea pellionella, Hofinarmophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp.*, Psylliodes chrysocephala, Epilachna varivestis, Atomaria* spp.*, Oryzaephilus surinamensis, Anthonomus* spp.*, Sitophilus* spp.*, Otiorrhynchus sulcatus, Cosmopolites sordidus, Ceuthorrhynchus assimilis, Hypera postica, Dermestes* spp.*, Trogoderma* spp.*, Anthrenus* spp.*, Attagenus* spp.*, Lyctus* spp.*, Meligethes aeneus, Ptinus* spp.*, Niptus hololeucus, Gibbium psylloides, Tribolium* spp.*, Tenebrio molitor, Agriotes* spp.*, Conoderus* spp.*, Melolontha melolontha, Amphimallon solstitialis, Costelytra zealandica* and *Lissorhoptrus oryzophilus.*

From the order of the Hymenoptera, for example, *Diprion* spp.*, Hoplocampa* spp.*, Lasius* spp.*, Monomorium pharaonis* and *Vespa* spp.

From the order of the Diptera, for example, *Aedes* spp.*, Anopheles* spp.*, Culex* spp.*, Drosophila melanogaster, Musca* spp.*, Fannia* spp.*, Calliphora erythrocephala, Lucilia* spp.*, Chrysomyia* spp.*, Cuterebra* spp.*, Gastrophilus* spp.*, Hyppobosca* spp.*, Stomoxys* spp.*, Oestrus* spp.*, Hypoderma* spp.*, Tabanus* spp.*, Tannia* spp.*, Bibio hortulanus, Oscinella frit, Phorbia* spp.*, Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the order of the Arachnida, for example, *Scorpio maurus, Latrodectus mactans, Acarus siro, Argas* spp.*, Omithodoros* spp.*, Dermanyssus gallinae, Eriophyes ribis, Phyllocoptruta oleivora, Boophilus* spp.*, Rhipicephalus* spp.*, Amblyomma* spp.*, Hyalomma* spp.*, Ixodes* spp.*, Psoroptes* spp.*, Chorioptes* spp.*, Sarcoptes* spp.*, Tarsonemus* spp.*, Bryobia praetiosa, Panonychus* spp.*, Tetranychus* spp.*, Hemitarsonemus* spp., and *Brevipalpus* spp.

The phytoparasitic nematodes include, for example, *Pratylenchus* spp.*, Radopholus similis, Ditylenchus dipsaci, Tylenchulus semipenetrans, Heterodera* spp.*, Globodera* spp.*, Meloidogyne* spp.*, Aphelenchoides* spp.*, Longidorus* spp.*, Xiphinema* spp.*, Trichodorus* spp. and *Bursaphelenchus* spp.

If appropriate, the compounds according to the invention can, at certain concentrations and application rates, also be employed as herbicides and microbicides, for example as fungicides, antimycotics and bactericides. If appropriate, they can also be used as intermediates or precursors in the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is liquid solvents, and/or solid carriers, optionally with the use of surfactants, that is emulsifiers and/or dispersants, and/or foam-formers.

If the extender used is water, it is also possible to employ, for example, organic solvents as auxiliary solvents. Essentially, suitable liquid solvents are: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

As solid carriers there are suitable:
for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers, such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants, such as inorganic pigments, for example iron oxide, titanium oxide and Prussian Blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95% by weight of active compound, preferably between 0.5 and 90%.

The active compounds according to the invention can be present in commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:
Fungicides:
aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, fiurametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-((6-methoxy)-3-pyridinyl)-cyclopropanecarboxamide, N-[2,2,2-trichloro-1-[(chloroacetyl)-amino]-ethyl]-benzamide, N-[3-chloro-4,5-bis-(2-propinyloxy)-phenyl]-N'-methoxy-methanimidamide, N-formyl-N-hydroxy-DL-alanine-sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate,
spiro[2H]-1-benzopyrane-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cyclopren, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pynrdathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348, 2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N''-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides or fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compound combinations of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the active compounds according to the invention also have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenopterons, such as

*Sirex juvencus, Urocerus gigas, Urocerus gigas taignus, Urocerus augur.*

Termites, such as

*Kaloternes flavicollis, Cryptotermes brevis, Heterotermes indicola, Reticulitermes flavipes, Reticulitermes santonensis, Reticulitermes lucifulgus, Mastotermes darwiniensis, Zootermopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising this are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and, if appropriate, dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, with the proviso that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Suitable additional mixing components are, preferably, the insecticides and fungicides mentioned in WO 94/29 268. The compounds mentioned in this document are an explicit constituent of the present application.

Especially preferred mixing components which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The active compound combinations according to the invention can also be used for protecting against colonization of articles, especially ships' hulls, screens, nets, constructions, quays and signalling equipment, which come into contact with seawater or brackish water.

Colonization by sessile Oligochaetae, such as Serpulidae, and by shellfish and species of the group Ledamorpha (goose barnacles), such as various *Lepas* and *Scalpellum* species, or by species of the group Balanomorpha (acorn barnacles), such as *Balanus* or *Pollicipes* species, increases the frictional resistance of ships and leads as a result, through increased energy consumption and frequent spells in dry dock, to a marked increase in the operating costs.

In addition to colonization by algae, for example *Ectocarpus* sp. and *Ceramium* sp., particular importance is attached to infestation by sessile Entomostraca groups, which are comprised under the name Cirripedia (cirriped crustacea).

Surprisingly, it has now been found that the active compound combinations according to the invention, when used alone or in combination with other active compounds, have a good antifouling (anti-colonization) effect.

By using compounds according to the invention, either alone or combination with other active compounds, it is possible to dispense with the use of heavy metals, such as, for example, in bis(trialkyltin)sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, the zinc and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides, or substantially to reduce the concentration of these compounds.

If appropriate, the ready-to-use antifouling paints may comprise yet further active compounds, preferably algicides, fungicides, herbicides, molluscicides or other antifouling active compounds.

Preferred co-components for the antifouling compositions according to the invention are:

algicides, such as
2-tert-butylamino-4-cyclopropylamino-6-methylthio-1,3, 5-triazine, dichlorophen, diuron, endothal, fentin acetate, isoproturon, methabenzthiazuron, oxyfluorfen, quinoclamine and terbutryn;

fungicides, such as
cyclohexylbenzo[b]thiophenecarboxamide S,S-dioxide, dichlofluanid, fluorfolpet, 3-iodo-2-propinyl butylcarbamate, tolylfluanid and azoles, such as
azaconazole, cyproconazole, epoxyconazole, hexaconazole, metconazole, propi-conazole and tebuconazole;

molluscicides, such as
fentin acetate, metaldehyde, methiocarb, niclosamid, thiodicarb and trimethacarb;

or customary active antifouling active compounds, such as 4,5-dichloro-2-octyl-4-isothiazolin-3-one, diiodomethyl paratryl sulphone, 2-(N,N-dimethylthiocarbamoylthio)-5-nitrothiazyl, potassium, copper, sodium and zinc salts of 2-pyridinethiole 1-oxide, pyridine triphenylborane, tetrabutyldistannoxane, 2,3,-5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention in a concentration of from 0.001 to 50% by weight, in particular from 0.01 to 20% by weight.

The antifouling compositions according to the invention furthermore comprise the customary components as described, for example, in Ungerer, Chem. Ind. 1985, 37, 730–732 and Williams, Antifouling Marine Coatings, Noyes, Park Ridge, 1973.

In addition to the algicidal, fungicidal, molluscicidal and insecticidal active compounds according to the invention, antifouling coating compositions comprise, in particular, binders.

Examples of acknowledged binders are polyvinyl chloride in a solvent system, chlorinated rubber in a solvent system, acrylic resins in a solvent system especially in an aqueous system, vinyl chloride/vinyl acetate copolymer systems in the form of aqueous dispersions or in the form of organic solvent systems, butadiene/styrene/acrylonitrile rubbers, drying oils, such as linseed oil, resin esters or modified hard resins in combination with tar or bitumen, asphalt and also epoxy compounds, small amounts of chlorinated rubber, chlorinated polypropylene and vinyl resins.

The coating compositions also optionally include inorganic pigments, organic pigments or dyestuffs, which are preferably insoluble in salt water. The coating compositions may also comprise materials such as rosin, for a controlled release of the active compounds. The coats may also include plasticizers, modifying agents which influence the rheological properties, and other conventional constituents. The compounds according to the invention or the abovementioned mixtures can also be incorporated into self-polishing antifouling systems.

The active compounds are also suitable for controlling animal pests, in particular insects, arachnids and mites, which are encountered in closed rooms, such as, for example, flats, factory halls, offices, vehicle cabins and the like. They can be used alone or in combination with other active compounds and auxiliaries in household insecticidal products for controlling these pests. They are active against sensitive and resistant species and against all stages of development. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

In the field of the household insecticides, they are used alone or in combination with other suitable active compounds, such as phosphoric acid esters, carbamates, pyrethroids, growth regulators or active compounds from other known classes of insecticide.

They are used in the form of aerosols, unpressurized sprays, for example pump and atomizer sprays, nebulizers, foggers, foams, gels, vaporizer products with vaporizer tablets made of cellulose or plastic, liquid vaporizers, gel and membrane vaporizers, propeller-operated vaporizers, energyless or passive vaporizer systems, moth papers, moth sachets and moth gels, as granules or dusts, in baits for scattering or bait stations.

The active compounds according to the invention can be used as defoliants, desiccants, haulm killers and, especially, as weed killers. Weeds in the broadest sense is understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and squares with and without tree plantings. Similarly, the active compounds according to the invention can be employed for controllling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad spectrum of activity when applied on the soil and to aboveground parts of plants. To a certain extent, they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam-formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, BAS-662H, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafen-strole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuiron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceac.

Some pathogens causing fungal and bacterial diseases which come under the generic names listed above are mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Altemaria* species, such as, for example, *Altemaria brassicae*; and

*Pseudocercosporella* species, such as, for example, *Pseudocercospprella herpotrichoides.*

The fact that the active compounds are well tolerated by plants at the concentrations required for controlling plant diseases permits the treatment of above-ground parts of plants, of propagation stock and seeds, and of the soil.

The active compounds according to the invention may also be employed to increase the yield of crops. Moreover, they have reduced toxicity and are tolerated well by plants.

If appropriate, the active compounds according to the invention can, at certain concentrations and application rates, also be employed as herbicides, for influencing plant growth and for controlling animal pests. If appropriate, they can also be used as intermediates and precursors for the synthesis of other active compounds.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds or compositions according to the invention preferably act against fungi, in particular moulds, wood-discolouring and wood-destroying fungi (Basidiomycetes), and against slime organisms and algae.

Microorganisms of the following genera may be mentioned as examples:

*Alternaria*, such as *Alternaria tenuis*,

*Aspergillus*, such as *Aspergillus niger*,

*Chaetomium*, such as *Chaetomium globosum*,

*Coniophora*, such as *Coniophora puetana*,

*Lentinus*, such as *Lentinus tigrinus*,

*Penicillium*, such as *Penicillium glaucum*,

*Polyporus*, such as *Polyporus versicolor*,

*Aureobasidium*, such as *Aureobasidium pullulans*,

*Sclerophoma*, such as *Sclerophoma pityophila*,

*Trichoderma*, such as *Trichoderma viride*,

*Escherichia*, such as *Escherichia coli*,

*Pseudomonas*, such as *Pseudomonas aeruginosa*, and

*Staphylococcus*, such as *Staphylococcus aureus*.

Depending on their particular physical and/or chemical properties, the active compounds can be converted to the customary formulations, such as solutions, emulsions, suspensions, powders, foams, pastes, granules, aerosols and micro-encapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl) ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro [4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)oxy]-2,5-thophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alphacypermethrin, alphamethrin, amitraz, averrmectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermnethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses,
halofenozide, HCH, heptenophos, hexaflumuron, hexythiazox, hydroprene,
imidacloprid, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron,
ometoate, oxamyl, oxydemethon M,
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos,
ribavirin,
salithion, sebufos, silafluofen, spinosad, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,
YI 5302,
zeta-cypermethrin, zolaprofos,
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate,
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides or fertilizers and growth regulators.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*), *Epidermophyton* species, such as *Epidermophyton floccosum*, *Aspergillus* species such as *Aspergillus niger* and *Aspergillus fumigatus*, *Trichophyton* species such as *Trichophyton mentagrophytes*, *Microsporon* species such as *Microsporon canis* and *audouinii*. The list of these fungi does by no means limit the mycotic spectrum covered, but is only for illustration.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compound are generally between 0.1 and 10,000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

The preparation and the use of the substances according to the invention is illustrated by the examples below.

PREPARATION EXAMPLES

Example I-1-a-1

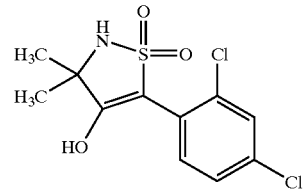

Process A

At from 20° C. to 40° C., 0.5 g of the compound according to Example II-1, dissolved in 1 ml of anhydrous dimethylformamide (DMF), is added dropwise to 0.4 g of potassium tert-butoxide in 1 ml of anhydrous DMF, the mixture is stirred at 40° C. and the reaction is monitored by thin-layer chromatography. After the reaction has ended, 10 ml of ice-water are added to the reaction mixture, which is, at from 0° C. to 10° C., acidified to pH 2 using conc. hydrochloric acid and then filtered off with suction. The residue is washed with ice-water and purified by silica gel chromatography using methylene chloride/ethyl acetate 3:1 as mobile phase.

Yield: 0.3 g ($\triangleq$ 64% of theory), m.p. 168° C.

The following compounds of the formula (I-1-a) were prepared analogously to Example I-1-a-1 and/or according to the general statements about the preparation of compounds of the formula (I-1-a).

TABLE 1

(I-1-a)

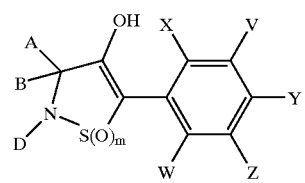

| Ex.-No. | V | W | X | Y | Z | B | A | D | m | m.p. ° C. | isomer |
|---|---|---|---|---|---|---|---|---|---|---|---|
| I-1-a-2 | H | Cl | Cl | H | H | CH₃ | CH₃ | H | 2 | 112–114 | — |
| I-1-a-3 | F | H | F | F | F | CH₃ | CH₃ | H | 2 | 112 | — |
| I-1-a-4 | H | H | Cl | Cl | H | —(CH₂)₂—CHOCH₃—(CH₂)₂— | | H | 2 | 199 | β |
| I-1-a-5 | H | H | Cl | Cl | H | —(CH₂)₂—CHCH₃—(CH₂)₂— | | H | 2 | 208 | β |
| I-1-a-6 | H | Cl | Cl | H | H | —(CH₂)₂—CHOCH₃—(CH₂)₂— | | H | 2 | 230 | β |
| I-1-a-7 | H | Cl | Cl | H | H | —(CH₂)₂—CHOCH₃—(CH₂)₂— | | H | 2 | 130 | β |
| I-1-a-8 | Cl | H | H | CF₃ | H | —(CH₂)₂—CHOCH₃—(CH₂)₂— | | H | 2 | 149 | β |
| I-1-a-9 | H | H | Cl | Cl | H | —(CH₂)₂—CHOC₂H₅—(CH₂)₂— | | H | 2 | 173 | β |
| I-1-a-10 | H | Cl | Cl | H | H | —(CH₂)₂—CHCH₃—(CH₂)₂— | | CH₃ | 2 | 250 | β |
| I-1-a-11 | H | H | H | Cl | H | H | 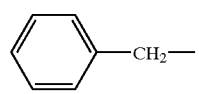 | H | 2 | 182 | — |

TABLE 1-continued

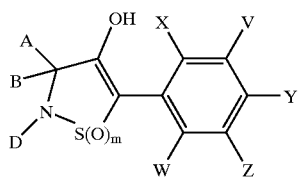

(I-1-a)

| Ex.-No. | V | W | X | Y | Z | B | A | D | m | m.p. °C. | isomer |
|---|---|---|---|---|---|---|---|---|---|---|---|
| I-1-a-12 | H | H | $NO_2$ | H | H | H | ![phenyl]—$CH_2$— | H | 2 | MS/ESI M 345 (100%) | — |
| I-1-a-13 | H | H | H | Cl | H | H | Cl—![phenyl]—$CH_2$— | H | 2 | 169–170 | — |
| I-1-a-14 | H | H | $NO_2$ | H | H | H | Cl—![phenyl]—$CH_2$— | H | 2 | MS-ESI M 379 (100%) | — |
| I-1-a-15 | H | H | Cl | Cl | H | —$(CH_2)_2$—O—$(CH_2)_2$— | | H | 2 | 220 | — |
| I-1-a-16 | H | H | Cl | Cl | H | —$CH_2$—O—$(CH_2)_3$— | | H | 2 | 189 | — |

Example I-1-b-1

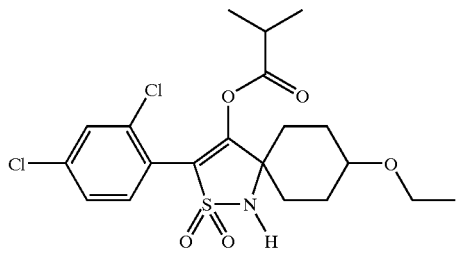

0.23 g (0.59 mmol) of the compound according to Example I-1-a-9 is initially charged in 2 ml of absolute methylene chloride, 0.06 g (0.59 mmol) of triethylamine is added and 0.065 g (0.59 mmol) of isobutyryl chloride in 1 ml of absolute methylene chloride is added dropwise. The mixture is stirred under reflux overnight and washed with water, the aqueous phase is extracted with methylene chloride and the combined methylene chloride phases are dried over $MgSO_4$ and concentrated, and the crystalline residue is stirred with cleaner's naphtha. The solid is filtered off with suction and dried in air.

Yield: 0.135 g (49.5% of theory), m.p.: 112° C.

The following compounds of the formulae (I-1-b) and (I-1-c) were prepared analogously to Example I-1-b-1:

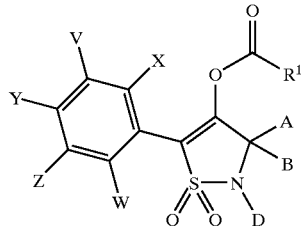

(I-1-b)

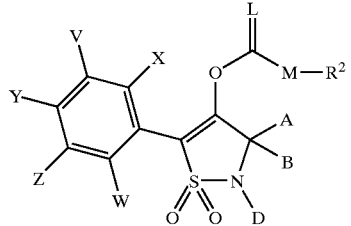

(I-1-c)

TABLE 1'

| Ex. No. | V | W | X | Y | Z | $R^1$ | $R^2$ | D | L | M | A | B | m.p. °C. |
|---|---|---|---|---|---|---|---|---|---|---|---|---|---|
| I-1-b-1 | H | H | Cl | Cl | H | CH—$(CH_3)_2$ | — | H | — | — | —$(CH_2)_2$—CH—$(CH_2)_2$— <br> \|<br>$OC_2H_5$ | | 112° C. |
| I-1-b-2 | H | H | Cl | Cl | H | CH—$(CH_3)_2$ | — | H | — | — | —$CH_2$—O—$(CH_2)_3$— | | 120° C. |
| I-1-b-3 | H | H | Cl | Cl | H | CH—$(CH_3)_2$ | — | H | — | — | —$(CH_2)_2$—O—$(CH_2)_2$— | | 145° C. |

TABLE 1'-continued

| Ex. No. | V | W | X | Y | Z | R¹ | R² | D | L | M | A | B | m.p. °C. |
|---|---|---|---|---|---|---|---|---|---|---|---|---|---|
| I-1-c-1 | H | H | Cl | Cl | H | — | CH$_2$—CH—(CH$_3$)$_2$ | H | O | O | —(CH$_2$)$_2$—CH—(CH$_2$)$_2$<br>\|<br>OC$_2$H$_5$ | | 124° C. |
| I-1-c-2 | H | H | Cl | Cl | H | — | CH$_2$—CH—(CH$_3$)$_2$ | H | O | O | —CH$_2$—O—(CH$_2$)$_3$— | | 121° C. |
| I-1-c-3 | H | H | Cl | Cl | H | — | C$_2$H$_5$ | H | O | O | —(CH$_2$)$_2$—O—(CH$_2$)$_2$— | | 162° C. |
| I-1-c-4 | H | H | Cl | Cl | H | — | CH$_2$—CH—(CH$_3$)$_2$ | H | O | O | —(CH$_2$)$_2$—O—(CH$_2$)$_2$— | | 154° C. |

Example I-1-i-1

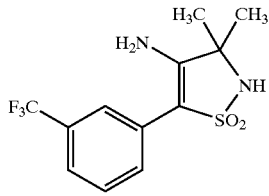

Process M-β

At 40° C., 5.5 g of the compound according to Example XVIII-1, suspended in 5 ml of anhydrous DMF, are added dropwise to 5 g of potassium tert-butoxide in 30 ml of anhydrous DMF, and the mixture is stirred at 60° C. for 2 hours. The solvent is distilled off under reduced pressure and the residue is taken up in water, stirred into 200 ml of 20% strength hydrochloric acid, filtered off with suction and dried. The residue is purified by silica gel chromatography using methylene chloride/ethyl acetate 5:3 as mobile phase.

Yield: 2.3 g ($\triangleq$ 42% of theory), m.p. 175° C.

Example I-1-i-2

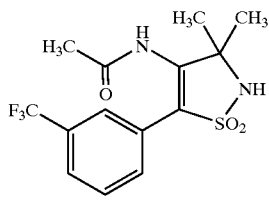

Process N-α

0.51 g of the compound (I-1-i-1), 0.15 g of acetyl chloride and 0.2 g of acetic anhydride in 20 ml of anhydrous toluene are heated at 60° C., and the progress of the reaction is monitored by thin-layer chromatography. The solvent is distilled off under reduced pressure and the residue is purified by silica gel chromatography using methylene chloride/ethyl acetate 5:3 as mobile phase.

Yield: 0.35 g ($\triangleq$ 61% of theory), m.p. 196° C.

Example I-1-i-3

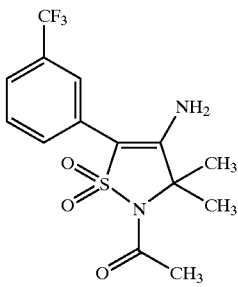

Process O

At 0° C., 0.35 g of the compound (I-1-i-1) in 30 ml of anhydrous tetrahydrofuran (THF) is added dropwise to 0.04 g of sodium hydride (60%) in 10 ml of anhydrous THF. At 20° C., 0.1 g of acetyl chloride is then added dropwise, and the mixture is then stirred at 20° C., the progress of the reaction being monitored by thin-layer chromatography. The mixture is carefully admixed with water and extracted with methylene chloride, and the extract is dried and concentrated. The residue is purified by silica gel chromatography using methylene chloride/ethyl acetate 3:1 as mobile phase.

Yield: 0.35 g ($\triangleq$ 99% of theory), m.p. 142° C.

Example I-1-i4

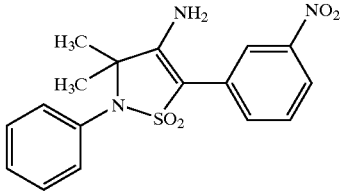

1.4 g of the compound (XVIII-1'-9) are initially charged in 100 ml of acetonitrile. After addition of 0.93 g of benzyl bromide and 1.02 g of potassium carbonate, the mixture is heated under reflux for 22 hours. The precipitate is filtered off with suction, the filtrate is concentrated and the residue is stirred with ether/acetone, filtered off with suction and dried.

Yield: 1.1 g ($\triangleq$ 59% of theory), m.p. 190° C.

The following compounds of the formula (I-1-i) were prepared analogously to Examples (I-1-i-1) to (I-1-i-4) and/or in accordance with the general statements on the preparation of compounds of the formula (I-1-i):

TABLE 2

(I-1-i)

| Ex. No. | V | W | X | Y | Z | B | A | D | m | R⁹ | R¹⁰ | m.p. ° C. |
|---|---|---|---|---|---|---|---|---|---|---|---|---|
| I-1-i-5 | $CF_3$ | H | H | Cl | H | $CH_3$ | $CH_3$ | H | 2 | H | H | 173 |
| I-1-i-6 | H | Cl | Cl | $CF_3$ | H | $CH_3$ | $CH_3$ | H | 2 | H | H | |
| I-1-i-7 | H | H | Cl | Cl | H | $CH_3$ | $CH_3$ | H | 2 | H | H | 228 |
| I-1-i-8 | H | H | Cl | Cl | H | $CH_3$ | $CH_3$ | H | 2 | H | $CO-CH_3$ | 230 |
| I-1-i-9 | H | H | Cl | Cl | H | $CH_3$ | $CH_3$ | $CH_3CO-$ | 2 | H | H | >250 |
| I-1-i-10 | H | H | H | $OCF_3$ | H | $CH_3$ | $CH_3$ | benzyl | 2 | H | H | 182 |
| I-1-i-11 | H | H | H | $OCF_3$ | H | $CH_3$ | $CH_3$ | 4-Cl-benzyl | 2 | H | H | 195 |
| I-1-i-12 | $NO_2$ | H | H | H | H | $CH_3$ | $CH_3$ | 4-Cl-benzyl | 2 | H | H | 180 |
| I-1-i-13 | H | H | H | F | H | $CH_3$ | $CH_3$ | benzyl | 2 | H | H | 162 |

Example II-1

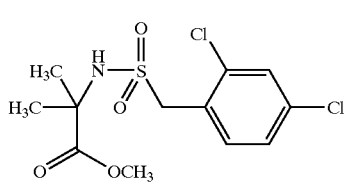

3.04 g of methyl aminoisobutyrate hydrochloride are initially charged in 50 ml of anhydrous tetrahydrofuran (THF). After addition of 5.6 ml of triethylamine, 2.6 g of 2,4-dichlorobenzylsulphonyl chloride, dissolved in 10 ml of anhydrous THF, are added dropwise, and the mixture is stirred at room temperature for 1 h. The reaction mixture is poured into 200 ml of 1 N hydrochloric acid and extracted with methylene chloride, the extract is dried and the solvent is distilled off. The residue is purified by silica gel chromatography using ethyl acetate/n-hexane 2:1 as mobile phase.

Yield 0.68 g (24% of theory), m.p.: 84° C.

Example II-2

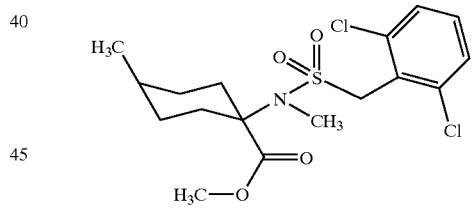

At room temperature, 0.04 g (0.94 mmol) of sodium hydride (60%) is initially charged in 2 ml of absolute dimethylformamide, and 0.37 g (0.94 mmol) of methyl 1-[[[(2,6-dichlorophenyl)methyl]sulphonyl]-amino]-4-methylcyclohexanecarboxylate, dissolved in 1 ml of absolute dimethylformamide, is added. The mixture is stirred at room temperature for 10 minutes, 0.2 g (1.41 mmol) of methyl iodide is then added dropwise, and the mixture is stirred at room temperature overnight. The mixture is poured into ice-water and made slightly acidic using concentrated hydrochloric acid, and the solid is filtered off with suction and dried in the air.

Yield: 0.325 g (84.8% of theory).

Melting point: 100° C.

The following compounds of the formula (II) were prepared analogously to Examples II-1 and II-2 and/or in accordance with the general statements on the preparation of compounds of the formula (II):

benzylsulfonyl chloride, dissolved in 10 ml of anhydrous THF, are then added dropwise at 0° C. The mixture is stirred

TABLE 3

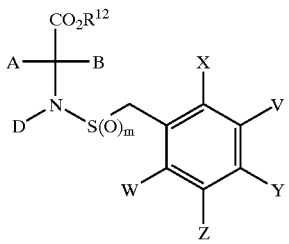

(II)

| Ex. No. | V | W | X | Y | Z | B | A | D | m | R¹² | m.p. °C. | isomer |
|---|---|---|---|---|---|---|---|---|---|---|---|---|
| II-3 | H | Cl | Cl | H | H | CH₃ | CH₃ | H | 2 | CH₃ | 115 | — |
| II-4 | H | H | F | H | H | CH₃ | CH₃ | H | 2 | CH₃ | 67 | — |
| II-5 | H | H | CF₃ | H | H | CH₃ | CH₃ | H | 2 | CH₃ | | — |
| II-6 | H | H | H | F | H | CH₃ | CH₃ | H | 2 | CH₃ | 53 | — |
| II-7 | F | H | H | H | H | CH₃ | CH₃ | H | 2 | CH₃ | 56 | — |
| II-8 | CF₃ | H | H | Cl | H | CH₃ | CH₃ | H | 2 | CH₃ | 85 | — |
| II-9 | F | F | F | F | H | CH₃ | CH₃ | H | 2 | CH₃ | 91 | — |
| II-10 | H | H | Cl | Cl | H | —(CH₂)₂—CHOCH₃—(CH₂)₂— | | H | 2 | CH₃ | 102 | β |
| II-11 | H | H | Cl | Cl | H | —(CH₂)₂—CHCH₃—(CH₂)₂— | | H | 2 | CH₃ | 103 | β |
| II-12 | H | Cl | Cl | H | H | —(CH₂)₂—CHOCH₃—(CH₂)₂— | | H | 2 | CH₃ | 103 | β |
| II-13 | H | H | Cl | Cl | H | —(CH₂)₂—CHOC₂H₅—(CH₂)₂— | | H | 2 | CH₃ | 133 | β |
| II-14 | H | H | Cl | Cl | H | —(CH₂)₂—CHCH₃—(CH₂)₂— | | H | 2 | CH₃ | 195 | β |
| II-15 | Cl | H | H | CF₃ | H | —(CH₂)₂—CHOCH₃—(CH₂)₂— | | H | 2 | CH₃ | oil | β |
| II-16 | H | H | Cl | Cl | H | —(CH₂)₂—CHOC₂H₅—(CH₂)₂— | | H | 2 | CH₃ | 129 | β |
| II-17 | H | H | NO₂ | H | H | H | 4-Cl-C₆H₄-CH₂— | H | 2 | CH₃ | MS-FAB M⁺ 411 (100%) | — |
| II-18 | H | H | H | Cl | H | H | C₆H₅-CH₂— | H | 2 | CH₃ | 106 | — |
| II-19 | H | H | NO₂ | H | H | H | C₆H₅-CH₂— | H | 2 | CH₃ | 91 | — |
| II-20 | H | H | H | Cl | H | H | 4-Cl-C₆H₄-CH₂— | H | 2 | CH₃ | 144–146 | — |
| II-21 | H | H | Cl | Cl | H | —(CH₂)₂—O—(CH₂)₂— | | H | 2 | CH₃ | 130 | — |
| II-22 | H | H | Cl | Cl | H | —CH₂—O(CH₂)₃— | | H | 2 | CH₃ | 93 | — |
| II-23 | H | H | Br | Br | F | —(CH₂)₂—O—(CH)₃— | | H | 2 | CH₃ | 129° C. | — |
| II-24 | H | H | Br | Br | F | —(CH₂)₂—CHOCH₃—(CH₂)₂— | | H | 2 | CH₃ | 105° C. | — |
| II-25 | Cl | H | H | H | Cl | —(CH₂)₂—CHOCH₃—(CH₂)₂— | | H | 2 | CH₃ | 65° C. | — |
| II-26 | Cl | H | H | H | Cl | —(CH₂)—O—(CH₂)₃— | | H | 2 | CH₃ | 148° C. | — |
| II-27 | Cl | H | H | H | Cl | —(CH₂)₂—O—(CH₂)₂— | | H | 2 | CH₃ | 210° C. | — |
| II-28 | H | H | Br | Br | F | —(CH₂)₂—O—(CH₂)₂— | | H | 2 | CH₃ | 150° C. | — |

Example XVIII-1'-1

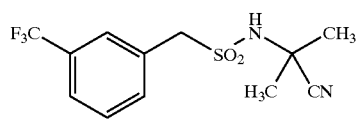

1.7 g of 2-amino-isobutyronitrile are initially charged in 40 ml of anhydrous tetrahydrofuran (THF). 2.8 ml of triethylamine are added, and 5 g of 3-trifluoromethyl-benzylsulfonyl chloride, dissolved in 10 ml of anhydrous THF, are then added dropwise at 0° C. The mixture is stirred at 20° C. for 1 hour, then stirred into 200 ml of 1 N hydrochloric acid and extracted, the extract is dried and the solvent is evaporated under reduced pressure. The residue is purified by silica gel chromatography using hexane/ethyl acetate 7:3 as mobile phase.

Yield: 6.1 g (=99% of theory), m.p.: 107° C.

The following compounds are prepared analogously to Example (XVIII-1'-1) and/or in accordance with the general statements on the preparation of compounds of the formula (XVIII-1'):

TABLE 4

(XVIII-1')

| Ex. No. | V | W | X | Y | Z | B | A | D | m | m.p. °C. |
|---|---|---|---|---|---|---|---|---|---|---|
| XVIII-1'-2 | H | H | Cl | Cl | H | $CH_3$ | $CH_3$ | H | 2 | 138 |
| XVIII-1'-3 | H | Cl | Cl | $CF_3$ | H | $CH_3$ | $CH_3$ | H | 2 | 128 |
| XVIII-1'-4 | H | H | $CF_3$ | H | H | $CH_3$ | $CH_3$ | H | 2 | |
| XVIII-1'-5 | $CF_3$ | H | H | Cl | H | $CH_3$ | $CH_3$ | H | 2 | |
| XVIII-1'-6 | H | H | Cl | Cl | H | —$(CH_2)_5$— | | H | 2 | |
| XVIII-1'-7 | H | Cl | Cl | H | H | —$(CH_2)_5$— | | H | 2 | 188 |
| XVIII-1'-8 | H | H | H | $OCF_3$ | H | $CH_3$ | $CH_3$ | H | 2 | 126 |
| XVIII-1'-9 | $NO_2$ | H | H | H | H | $CH_3$ | $CH_3$ | H | 2 | 135 |
| XVIII-1'-10 | H | H | H | F | H | $CH_3$ | $CH_3$ | H | 2 | oil |

Example I-2-a-1

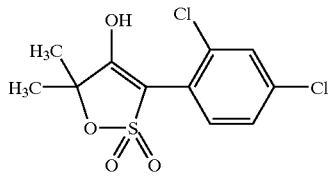

Process B 0.73 g (18.2 mmol) of sodium hydride (60%) are initially charged in 4 ml of absolute dimethylformamide, the mixture is cooled to 0° C. and 3.1 g (9.1 mmol) of methyl 2-{[(2,4-dichlorobenzyl)sulphonyl]oxy}-2-methylpropanoate according to Example (III-1) in 5 ml of absolute dimethylformamide are added dropwise. The mixture is stirred at room temperature overnight and then poured onto ice, acidified using concentrated hydrochloric acid and extracted repeatedly with methylene chloride. The extract is dried over magnesium sulphate and concentrated, giving the compound I-2-a-1 as a yellow oil.

Yield: 2 g (71% of theory).

$^1$H-NMR (400 MHz, $CDCl_3$): δ=1.65, s, 6H (2×$CH_3$); 7.49, dd, 1H; 7.55, dd, 1H, 7.81, d, 1H; 12.6, bs, 1H.

The following compounds of the formula (I-2-a) were prepared analogously to Example I-2-a-1 and/or in accordance with the general statements on the preparation of compounds of the formula (I-2-a):

TABLE 5

(I-2-a)

| Ex. No. | V | W | X | Y | Z | A | B | m | m.p. °C. |
|---|---|---|---|---|---|---|---|---|---|
| I-2-a-2 | H | H | H | $CF_3$ | H | $CH_3$ | $CH_3$ | 2 | 90 |
| I-2-a-3 | $NO_2$ | H | H | H | H | $CH_3$ | $CH_3$ | 2 | 83 |
| I-2-a-4 | H | H | F | $CF_3$ | H | $CH_3$ | $CH_3$ | 2 | 70 |
| I-2-a-5 | F | F | F | F | H | $CH_3$ | $CH_3$ | 2 | oil |
| I-2-a-6 | $CF_3$ | H | H | Cl | H | $CH_3$ | $CH_3$ | 2 | oil |
| I-2-a-7 | H | Cl | Cl | H | H | $CH_3$ | $CH_3$ | 2 | 200 |
| I-2-a-8 | H | H | Cl | Cl | H | —$(CH_2)_2$—CHOCH$_3$—$(CH_2)_2$— | | 2 | oil |
| I-2-a-9 | H | H | Cl | Cl | H | —$(CH_2)_2$—CHCH$_3$—$(CH_2)_2$— | | 2 | oil |
| I-2-a-10 | H | H | Cl | Cl | H | —$(CH_2)_2$—CHOC$_2$H$_5$—$(CH_2)_2$— | | 2 | oil |
| 1-2-a-11 | H | Cl | Cl | H | H | —$(CH_2)_2$—CHCH$_3$—$(CH_2)_2$— | | 2 | oil |
| I-2-a-12 | H | Cl | Cl | H | H | —$(CH_2)_2$—CHOCH$_3$—$(CH_2)_2$— | | 2 | 248 |

Example I-2-i-1

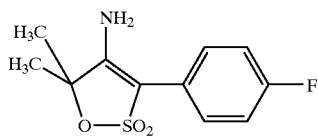

4 g of the compound XVIII-2'-1 are initially charged in 25 ml of acetonitrile. After addition of 0.24 g of diazabicycloundecene (DBU), the mixture warms to 32° C. Stirring at room temperature is continued for a further 7 h, and the mixture is then concentrated. The residue is suspended in toluene/diisopropyl ether, filtered off with suction and dried.

Yield: 3.6 g ($\triangleq$ 90% of theory), m.p. 201° C.

The following compounds of the formula (I-2-i) were prepared analogously to Example I-2-i-1 and/or in accordance with the general statements on the preparation of compounds of the formula (I-2-i):

TABLE 6

(I-2-i)

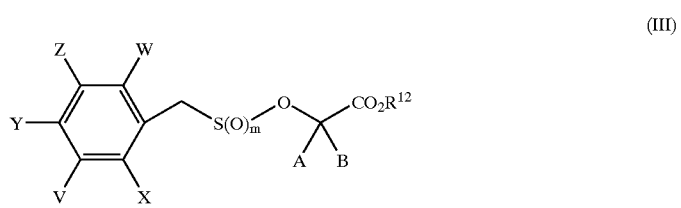

| Ex. No. | V | W | X | Y | Z | A | B | $R^9$ | $R^{10}$ | m.p. ° C. |
|---|---|---|---|---|---|---|---|---|---|---|
| I-2-i-2 | $CF_3$ | H | H | H | H | $CH_3$ | $CH_3$ | H | H | 181 |
| I-2-i-3 | H | H | H | $OCF_3$ | H | $CH_3$ | $CH_3$ | H | H | 126 |
| I-2-i-4 | $NO_2$ | H | H | H | H | $CH_3$ | $CH_3$ | H | H | 186 | where m = 2

Example III-1

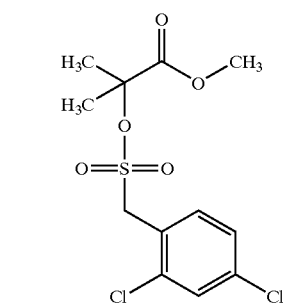

At 0° C., 1.24 g (10.5 mmol) of methyl 2-hydroxyisobutyrate are initially charged in 11 ml of pyridine, and 3 g (11.5 mmol) of 2,4-dichlorobenzylsulphonyl chloride are added a little at a time. The mixture is allowed to stand in a fridge at 5° C. for 5 days and then poured onto 50 g of ice, 10.5 g of concentrated sulfuric acid are added, the mixture is extracted with methyl tert-butyl ether, and the extract is dried over magnesium sulphate and concentrated, giving the compound III-1 as an oil.

Yield: 3.22 g (81.6% of theory).

$^1$H-NMR (400 MHz, $CDCl_3$): δ=1.7, s, 6H (2×$CH_3$); 3.75, s, 3H ($OCH_3$); 4.67, s, 2H ($CH_2$); 7.28, dd, 1H; 7.5, m, 2H.

The following compounds of the formula (III) were prepared analogously to Example III-1 and/or in accordance with the general statements on the preparation of the compounds of the formula (III):

TABLE 7

(III)

| Ex. No. | V | W | X | Y | Z | A | B | m | $R^{12}$ | m.p. ° C. |
|---|---|---|---|---|---|---|---|---|---|---|
| III-2 | H | H | H | $CF_3$ | H | $CH_3$ | $CH_3$ | 2 | $CH_3$ | oil |
| III-3 | $NO_2$ | H | H | H | H | $CH_3$ | $CH_3$ | 2 | $CH_3$ | oil |
| III-4 | H | H | F | $CF_3$ | H | $CH_3$ | $CH_3$ | 2 | $CH_3$ | oil |
| III-5 | F | F | F | F | H | $CH_3$ | $CH_3$ | 2 | $CH_3$ | oil |
| III-6 | $CF_3$ | H | H | Cl | H | $CH_3$ | $CH_3$ | 2 | $CH_3$ | oil |
| III-7 | H | Cl | Cl | H | H | $CH_3$ | $CH_3$ | 2 | $CH_3$ | 97.5 |
| III-8 | H | H | Cl | Cl | H | —$(CH_2)_2$—$CHOCH_3$—$(CH_2)_2$ | | 2 | $C_2H_5$ | oil |
| III-9 | H | H | Cl | Cl | H | —$(CH_2)_2$—$CHCH_3$—$(CH_2)_2$ | | 2 | $C_2H_5$ | oil |
| III-10 | H | H | Cl | Cl | H | —$(CH_2)_2$—$CHOC_2H_5$—$(CH_2)_2$ | | 2 | $C_2H_5$ | oil |
| III-11 | H | Cl | Cl | H | H | —$(CH_2)_2$—$CHCH_3$—$(CH_2)_2$ | | 2 | $C_2H_5$ | oil |
| III-12 | H | Cl | Cl | H | H | —$(CH_2)_2$—$CHOCH_3$—$(CH_2)_2$ | | 2 | $C_2H_5$ | 99 |

Example XVIII-2'-1

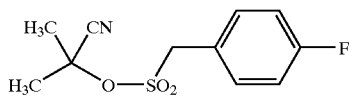

4.48 g of 2-hydroxyisobutyronitrile are initially charged in 120 ml of methylene chloride and admixed with 7.2 g of triethylamine, 10 g of 4-fluorobenzylsulphonyl chloride are added dropwise at 0° C. and the mixture is stirred at room temperature for 6 h. The reaction solution is taken up in water and the organic phase is separated off, dried and concentrated. The residue is purified by silica gel chromatography using toluene/ether 10:1 as mobile phase.

Yield: 5.1 g ($\triangleq$ 37% of theory), m.p. 68° C.

The following compounds of the formula (XVIII-2') were prepared analogously to Example XVIII-2'-1 and/or in accordance with the general statements on the preparation of compounds of the formula (XVIII-2'):

TABLE 8

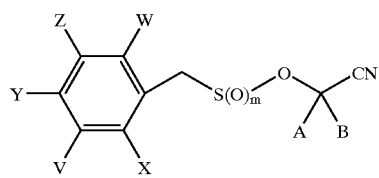

(XVIII-2')

| Ex. No. | V | W | X | Y | Z | A | B | m.p. ° C. |
|---|---|---|---|---|---|---|---|---|
| XVIII-2'-2 | $CF_3$ | H | H | H | H | $CH_3$ | $CH_3$ | 63 |
| XVIII-2'-3 | H | H | H | $OCF_3$ | H | $CH_3$ | $CH_3$ | 68 |
| XVIII-2'-4 | $NO_2$ | H | H | H | H | $CH_3$ | $CH_3$ | 85 | where m = 2

Example I-3-a-1

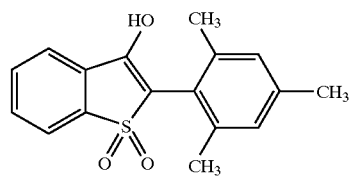

Process C 0.81 g (20.2 mmol) of sodium hydride (60%) is initially charged in 5 ml of absolute dimethylformamide, and 3.2 g (9.63 mmol) of methyl 2-[[(2,4,6-trimethylphenyl)-methyl]sulphonyl]-benzoate in 5 ml of absolute dimethylformamide are added dropwise. The mixture is stirred at room temperature overnight, poured into ice-water and acidified with hydrochloric acid, and the solid is filtered off with suction, washed with ice-water and cleaner's naphtha and dried in the air.

Yield: 3 g (quantitative).

Melting point: 220–225° C.

The following compounds of the formula I-3-a were prepared analogously to Example I-3-a-1 and/or in accordance with the general statements on the preparation of compounds of the formula (I-3-a):

TABLE 9

I-3-a

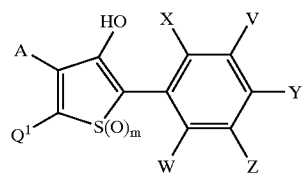

| Ex. No. | V | W | X | Y | Z | A | $Q^1$ | m | m.p. ° C. |
|---|---|---|---|---|---|---|---|---|---|
| I-3-a-2 | H | H | Cl | —O—$CH_2$—O— | | —CH=CH—CH=CH— | | 2 | 210–214 |
| I-3-a-3 | H | H | Cl | Cl | H | —CH=CH—CH=CH— | | 2 | 152–157 |
| I-3-a-4 | H | H | Cl | $CHF_2$ | Cl | —CH=CH—CH=CH— | | 2 | 177–182 |
| I-3-a-5 | H | H | $CH_3$ | $CH_3$ | $CH_3$ | —CH=CH—CH=CH— | | 2 | 179–182 |
| I-3-a-6 | H | H | F | $CF_3$ | H | —CH=CH—CH=CH— | | 2 | 109–112 |
| I-3-a-7 | $CH_3$ | $CH_3$ | $CH_3$ | $CH_3$ | H | —CH=CH—CH=CH— | | 2 | 143–145 |
| I-3-a-8 | H | H | $CH_3$ | $CH_3$ | H | —CH=CH—CH=CH— | | 2 | 188 |
| I-3-a-9 | H | H | Br | $CH_3$ | Br | —CH=CH—CH=CH— | | 2 | 204–208 |
| I-3-a-10 | Br | $CH_3$ | $CH_3$ | $CH_3$ | H | —CH=CH—CH=CH— | | 2 | 160–163 |
| I-3-a-11 | H | H | Cl | Cl | Cl | —CH=CH—CH=CH— | | 2 | 178 |
| I-3-a-15 | H | H | $CH_3$ | H | $CH_3$ | —CH=CH—CH=CH— | | 2 | 178 |
| I-3-a-16 | H | H | $CH_3$ | $OCH_3$ | $CH_3$ | —CH=CH—CH=CH— | | 2 | 177 |
| I-3-a-17 | Phenyl | H | $CH_3$ | H | H | —CH=CH—CH=CH— | | 2 | 204 |
| I-3-a-19 | H | H | $OCH_3$ | Cl | Br | —CH=CH—CH=CH— | | 2 | 98 |
| I-3-a-20 | H | H | $CF_3$ | Cl | H | —CH=CH—CH=CH— | | 2 | 184 |
| I-3-a-21 | H | H | $CF_3$ | $CF_3$ | H | —CH=CH—CH=CH— | | 2 | 141 |
| I-3-a-22 | Cl | H | F | F | Cl | —CH=CH—CH=CH— | | 2 | |

TABLE 9-continued

I-3-a

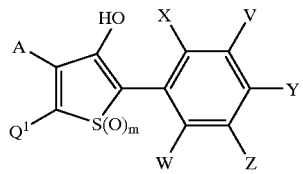

| Ex. No. | V | W | X | Y | Z | A | Q$^1$ | m | m.p. ° C. |
|---|---|---|---|---|---|---|---|---|---|
| I-3-a-23 | H | CH$_3$ | CH$_3$ | CH$_3$ | H | —(CH$_2$)$_3$— | | 2 | 172 |
| I-3-a-24 | H | Cl | Cl | H | H | —(CH$_2$)$_3$— | | 2 | 179 |
| I-3-a-25 | Cl | Cl | H | H | H | —(CH$_2$)$_3$— | | 2 | 157 |
| I-3-a-26 | H | H | Cl | Cl | H | —(CH$_2$)$_3$— | | 2 | 180 |
| I-3-a-27 | H | H | OCH$_3$ | CH$_3$ | Cl | —(CH$_2$)$_3$— | | 2 | 116 |
| I-3-a-29 | H | CH$_3$ | CH$_3$ | CH$_3$ | H | —(CH$_2$)$_2$—C(CH$_3$)$_2$—CH$_2$— | | 2 | 157 |

Example I-3-i-1

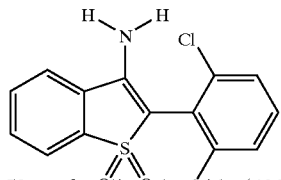

0.52 g of sodium hydride (60%) is initially charged in 8 ml of anhydrous dimethylformamide, and with ice-cooling, 4.2 g of the compound according to Example XVIII-3'-1, dissolved in 8 ml of anhydrous dimethylformamide, are added dropwise. The mixture is stirred at room temperature overnight, poured into ice-water and neutralized with hydrochloric acid, and the solid is filtered off with suction and dried.

Yield: 4.2 g ($\triangleq$ 100% of theory), m.p. 242–245° C.

Example I-3-i-2 of melting point 268–270° C. is obtained analogously to Example I-3-i-1.

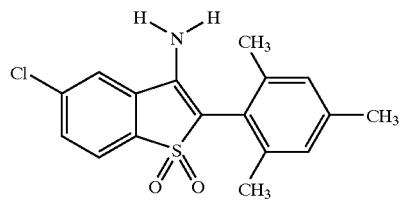

Example IV-1

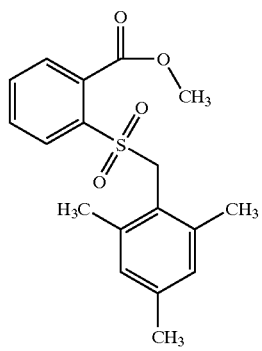

2.9 g (9.65 mmol) of methyl 2-[[(2,4,6-trimethylphenyl)methyl]thio]-benzoate are initially charged in 30 ml of CH$_2$Cl$_2$, and 6.66 g (19.3 mmol) of m-chloroperbenzoic acid (50% strength) are added a little at a time. The mixture is stirred at room temperature overnight and filtered off with suction, and the filtrate is admixed with 0.5 ml of dimethyl sulphide and stirred at room temperature for 1 hour. The filtrate is admixed with 50 ml of saturated NaHCO$_3$ solution and stirred at room temperature for 30 minutes. The aqueous phase is separated off and extracted twice with CH$_2$Cl$_2$, and the combined organic phases are dried and concentrated.

Yield: 3.3 g (quantitative), melting point: 132–136° C.

The following compounds of the formula (IV) are obtained analogously to Example IV-1 and/or in accordance with the general statements of the preparation of compounds of the formula (IV):

TABLE 10

(IV)

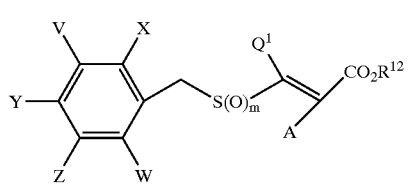

| Ex. No. | V | W | X | Y | Z | A | Q$^1$ | m | R$^{12}$ | m.p. ° C. |
|---|---|---|---|---|---|---|---|---|---|---|
| IV-2 | H | H | Cl | —CH$_2$—O—CH$_2$— | | —CH=CH—CH=CH— | | 2 | CH$_3$ | 148–154 |
| IV-3 | H | H | Cl | Cl | H | —CH=CH—CH=CH— | | 2 | CH$_3$ | 69–71 |

TABLE 10-continued (IV)

| Ex. No. | V | W | X | Y | Z | A | Q¹ | m | R¹² | m.p. ° C. |
|---|---|---|---|---|---|---|---|---|---|---|
| IV-4 | H | H | Cl | CHF$_2$ | Cl | —CH=CH—CH=CH— | | 2 | CH$_3$ | 114–119 |
| IV-5 | H | H | CH$_3$ | CH$_3$ | CH$_3$ | —CH=CH—CH=CH— | | 2 | CH$_3$ | oil |
| IV-6 | H | H | F | CF$_3$ | H | —CH=CH—CH=CH— | | 2 | CH$_3$ | 99–103 |
| IV-7 | CH$_3$ | CH$_3$ | CH$_3$ | CH$_3$ | H | —CH=CH—CH=CH— | | 2 | CH$_3$ | oil |
| IV-8 | H | H | CH$_3$ | CH$_3$ | H | —CH=CH—CH=CH— | | 2 | CH$_3$ | oil |
| IV-9 | H | H | Br | CH$_3$ | Br | —CH=CH—CH=CH— | | 2 | CH$_3$ | 160–163 |
| IV-10 | Br | CH$_3$ | CH$_3$ | CH$_3$ | H | —CH=CH—CH=CH— | | 2 | CH$_3$ | 137–138 |
| IV-11 | H | H | Cl | Cl | Cl | —CH=CH—CH=CH— | | 2 | CH$_3$ | 160–165 |
| IV-15 | H | H | CH$_3$ | H | CH$_3$ | —CH=CH—CH=CH— | | 2 | CH$_3$ | 164–168 |
| IV-16 | H | H | CH$_3$ | OCH$_3$ | CH$_3$ | —CH=CH—CH=CH— | | 2 | CH$_3$ | 154–157 |
| IV-17 | phenyl | H | CH$_3$ | H | H | —CH=CH—CH=CH— | | 2 | CH$_3$ | 113–115 |
| IV-19 | H | H | F | Cl | Br | —CH=CH—CH=CH— | | 2 | CH$_3$ | 136–139 |
| IV-20 | H | H | CF$_3$ | Cl | H | —CH=CH—CH=GH— | | 2 | CH$_3$ | 119–123 |
| IV-21 | H | H | CF$_3$ | CF$_3$ | H | —CH=CH—CH=CH— | | 2 | CH$_3$ | 94 |
| IV-22 | Cl | H | F | F | Cl | —CH=CH—CH=CH— | | 2 | CH$_3$ | 168–170 |
| IV-23 | H | CH$_3$ | CH$_3$ | CH$_3$ | H | —(CH$_2$)$_3$— | | 2 | CH$_3$ | 145 |
| IV-24 | H | Cl | Cl | H | H | —(CH$_2$)$_3$— | | 2 | CH$_3$ | oil |
| IV-25 | Cl | Cl | H | H | H | —(CH$_2$)$_3$— | | 2 | CH$_3$ | oil |
| IV-26 | H | H | Cl | Cl | H | —(CH$_2$)$_3$— | | 2 | CH$_3$ | oil |
| IV-27 | H | H | OCH$_3$ | CH$_3$ | Cl | —(CH$_2$)$_3$— | | 2 | CH$_3$ | oil |
| IV-29 | H | CH$_3$ | CH$_3$ | CH$_3$ | H | —(CH$_2$)$_2$—C(CH$_3$)$_2$—CH$_2$— | | 2 | CH$_3$ | 165 |

Example XXXI-1

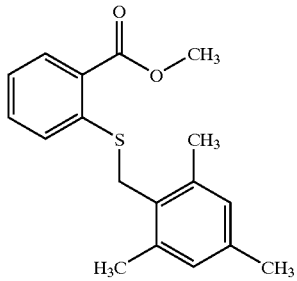

0.864 g (16 mmol) of sodium methoxide is dissolved in 15 ml of absolute methanol, 2.52 g (15 mmol) of methyl thiosalicylate are added and 2.53 g (15 mmol) of 2,4,6-trimethylbenzyl chloride are then slowly added dropwise. The mixture is stirred at room temperature overnight, concentrated and admixed with water, and the crystals are filtered off with suction, washed with cleaner's naphtha and dried in the air.

Yield: 2.98 g (66.1% of theory), melting point: 115–118° C.

The following compounds of the formula (XXXI) were prepared analogously to Example XXXI-1 and/or in accordance with the general statements on the preparation of compounds of the formula (XXXI):

TABLE 11

(XXXI)

| Ex. No. | V | W | X | Y | Z | A | Q¹ | R¹² | m.p. ° C. |
|---|---|---|---|---|---|---|---|---|---|
| XXXI-2 | H | H | Cl | —O—CH$_2$—O— | | —CH=CH—CH=CH— | | CH$_3$ | 120–123 |
| XXXI-3 | H | H | Cl | Cl | H | —CH=CH—CH=CH— | | CH$_3$ | 111–115 |
| XXXI-4 | H | H | Cl | CHF$_2$ | Cl | —CH=CH—CH=CH— | | CH$_3$ | 126–129 |
| XXXI-5 | H | H | CH$_3$ | CH$_3$ | CH$_3$ | —CH=CH—CH=CH— | | CH$_3$ | 104–106 |
| XXXI-6 | H | H | F | CF$_3$ | H | —CH=CH—CH=CH— | | CH$_3$ | 112–115 |
| XXXI-7 | CH$_3$ | CH$_3$ | CH$_3$ | CH$_3$ | H | —CH=CH—CH=CH— | | CH$_3$ | 131–134 |
| XXXI-8 | H | H | CH$_3$ | CH$_3$ | H | —CH=CH—CH=CH— | | CH$_3$ | 79 |

TABLE 11-continued (XXXI)

| Ex. No. | V | W | X | Y | Z | A | $Q^1$ | $R^{12}$ | m.p. ° C. |
|---|---|---|---|---|---|---|---|---|---|
| XXXI-9 | H | H | Br | $CH_3$ | Br | —CH=CH—CH=CH— | | $CH_3$ | 143 |
| XXXI-10 | Br | $CH_3$ | $CH_3$ | $CH_3$ | H | —CH=CH—CH=CH— | | $CH_3$ | 125 |
| XXXI-11 | H | H | F | Cl | Br | —CH=CH—CH=CH— | | $CH_3$ | 106 |
| XXXI-12 | H | H | $CF_3$ | Cl | H | —CH=CH—CH=CH— | | $CH_3$ | 82–83 |
| XXXI-13 | H | H | $CF_3$ | $CF_3$ | H | —CH=CH—CH=CH— | | $CH_3$ | 108–111 |
| XXXI-14 | Cl | H | F | F | Cl | —CH=CH—CH=CH— | | $CH_3$ | 132–135 |
| XXXI-15 | H | H | Cl | Cl | Cl | —CH=CH—CH=CH— | | $CH_3$ | 148 |
| XXX1-19 | H | H | $CH_3$ | H | $CH_3$ | —CH=CH—CH=CH— | | $CH_3$ | 135–139 |
| XXXI-20 | H | H | $CH_3$ | $OCH_3$ | $CH_3$ | —CH=CH—CH=CH— | | $CH_3$ | 143–146 |
| XXXI-21 | phenyl | H | $CH_3$ | H | H | —CH=CH—CH=CH— | | $CH_3$ | 91 |

Example XVIII-3'-1

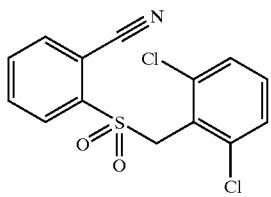

4.7 g of the compound according to Example XXXVI-1 are initially charged in 90 ml of methylene chloride and, at room temperature, 11.03 g of m-chloroperbenzoic acid are added. The mixture is stirred overnight, the precipitate is filtered off with suction and the filtrate is admixed with 0.5 ml of dimethyl sulphide and stirred for 1 hour. 50 ml of saturated sodium bicarbonate solution are added and the mixture is then extracted twice with methylene chloride and the extract is dried and concentrated. The residue is stirred with isopropanol and the crystals are filtered off with suction.

Yield: 4.9 g ($\hat{=}$ 94% of theory), m.p. 187–189° C.

Example XVIII-3'-2 of m.p. 190–193° C. is obtained analogously to Example XVIII-3'-1.

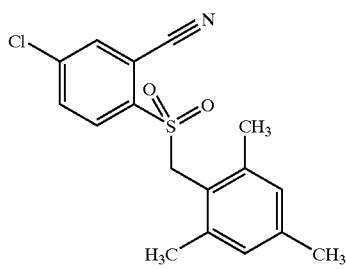

Example XXXVI-1

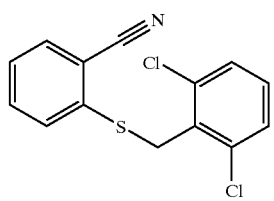

0.8 g of sodium hydride (60%) is initially charged in 10 ml of anhydrous dimethylformamide (DMF), and, at 0° C., 3.86 g of 2,6-dichlorobenzylmercaptan in 10 ml of anhydrous DMF are added dropwise. After 30 minutes, 2.42 g of 2-fluorobenzonitrile are added dropwise at 0° C., the mixture is stirred at room temperature overnight and then poured into water and filtered off with suction, and the residue is stirred with isopropanol, again filtered off with suction and dried.

Yield: 4.89 g ($\hat{=}$ 83% of theory), m.p. 111° C.

Example XXXVI-2 of m.p. 146° C. is obtained analogously to Example XXXVI-1

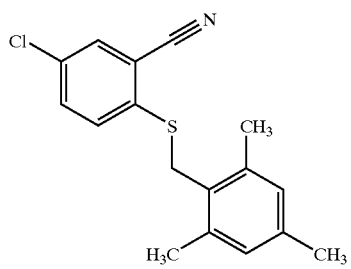

Example XXXI-23

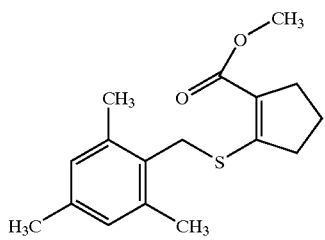

1.42 g (10 mmol) of methyl cyclopentanonecarboxylate, 2 g (12 mmol) of 2,4,6-trimethylbenzyl mercaptan and 1.9 g (10 mmol) of p-toluenesulphonic acid hydrate in 20 ml of acetic acid are stirred at room temperature overnight. The mixture is poured into water and the solid is filtered off with suction, washed with water and cleaner's naphtha and dried in the air.

Yield: 0.914 g (31.5% of theory), m.p. 139° C.

The following compounds of the formula (XXXI) were prepared analogously to Example XXXI-23 and/or in accordance with the general statements on the preparation of compounds of formula (XXXI) (variant 2):

TABLE 12

(XXXI)

| Ex. No. | V | W | X | Y | Z | A | $Q^1$ | $R^{12}$ | m.p. °C. |
|---|---|---|---|---|---|---|---|---|---|
| XXXI-24 | H | Cl | Cl | H | H | —$(CH_2)_3$— | | $CH_3$ | 152 |
| XXXI-25 | Cl | Cl | H | H | H | —$(CH_2)_3$— | | $CH_3$ | oil |
| XXXI-26 | H | H | Cl | Cl | H | —$(CH_2)_3$— | | $CH_3$ | 129 |
| XXXI-27 | H | H | $OCH_3$ | $CH_3$ | Cl | —$(CH_2)_3$— | | $CH_3$ | oil |
| XXXI-29 | H | $CH_3$ | $CH_3$ | $CH_3$ | H | —$(CH_2)_4$— | | $C_2H_5$ | oil |
| XXXI-30 | H | $CH_3$ | $CH_3$ | $CH_3$ | H | —$(CH_2)_2$—$C(CH_3)_2$—$CH_2$— | | $CH_3$ | 87 |

USE EXAMPLES

Example A

*Nephotettix* Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Rice seedlings (*Oryza sativa*) are treated by being dipped into the preparation of active compound of the desired concentration and are populated with the green rice leaf hopper (*Nephotettix cincticeps*) whilst the leaves are still moist.

After the desired period of time, the kill in % is determined. 100% means that all leaf hoppers have been killed; 0% means that none of the leaf hoppers have been killed.

In this test, for example, the compounds of Preparation Examples I-1-a-1 and I-1-a-11 effect, at an exemplary active compound concentration of 0.1%, a kill of 100% after 6 days.

Example B

*Plutella* Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moth (*Plutella xylostella*) while the leaves are still moist After the desired period of time, the kill in % is determined. 100% means that all caterpillars have been killed; 0% means that none of the caterpillars have been killed.

In this test, for example, the compounds of Preparation Example I-1-i-5 exhibits, at an exemplary active compound concentration of 0.1%, a kill of 100% after 7 days.

Example C

*Plutella* Test/Synthetic Feed

Solvent: 100 parts by weight of acetone

Emulsifier: 1900 parts by weight of methanol

To produce a suitable preparation of active compound, 1 part by weight of active compound is mixed with the stated amount of solvent, and the concentrate is diluted with methanol to the desired concentrations.

A stated amount of the preparation of active compound of the desired concentration is pipetted onto a standardized amount of synthetic feed. After the methanol has evaporated, a film box lid covered with approximately 100 *Plutella* eggs is placed onto each cavity. The freshly hatched larvae migrate onto the treated synthetic feed.

In this test, for example, the compound of Preparation Example I-2-i-3 exhibited, at an exemplary active compound concentration of 0.1%, an effect of 95% after 7 days.

What is claimed is:
1. A compound of the formula (I):

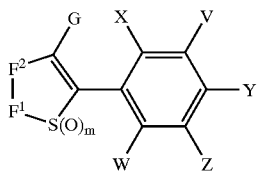

(I)

wherein
V, W, X, Y and Z independently of one another each represent hydrogen, halogen, nitro, cyano, alkyl, alkenyl, alkynyl, alkoxy, $S(O)_n$-alkyl, halogenoalkyl, halogenoalkoxy, or optionally substituted aryl, phenylalkyl, aryloxy, phenylalkyloxy or aryl-$S(O)_n$—, with the proviso that at least one of V, W, X, Y or Z is not hydrogen;
n represents the numbers 0 to 2;
m represents the numbers 1 and 2;

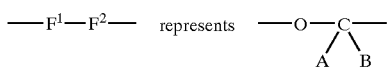

wherein
A represents hydrogen, in each case optionally halogen-substituted alkyl, alkenyl, alkoxyalkyl, polyalkoxyalkyl, or alkylthioalkyl, or represents optionally halogen-, alkyl-, halogenoalkyl-, alkoxy-, halogenoalkoxy-, cyano- or nitro-substituted aryl or arylalkyl;
B represents hydrogen, alkyl or alkoxyalkyl, and
G represents (a) hydroxyl or represents one of the groups:

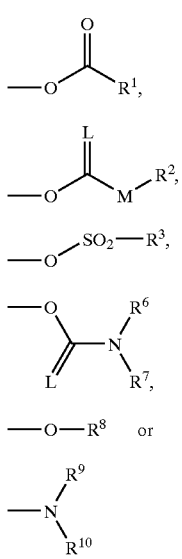

wherein
L represents oxygen or sulphur,
M represents oxygen or sulphur,
$R^1$ represents optionally halogen-substituted alkyl, alkenyl, alkoxyalkyl, alkylthioalkyl, or polyalkoxyalkyl, or represents optionally substituted phenyl, phenylalkyl, or phenoxyalkyl,
$R^2$ represents in each case optionally halogen-substituted alkyl, alkenyl, alkoxyalkyl, or poly- alkoxyalkyl or represents optionally substituted cycloalkyl, phenyl or benzyl,
$R^3$ represent optionally halogen-substituted alkyl, alkoxy, alkylamino, dialkylamino, alkylthio, alkenylthio, or cycloalkylthio or represents optionally substituted phenyl, benzyl, phenoxy or phenylthio, and
$R^6$ and $R^7$ independently of one another each represent hydrogen, optionally halogen-substituted alkyl, cycloalkyl, alkenyl, alkoxy, or alkoxyalkyl, represent optionally substituted phenyl, or represent optionally substituted benzyl,
$R^8$ represents optionally halogen-substituted alkyl, alkoxyalkyl, alkenyl, alkenyloxyalkyl, alkynyl, alkynyloxyalkyl, alkylcarbonylalkyl, alkoxycarbonylalkyl or represents optionally substituted cycloalkyl or represents optionally substituted arylalkyl, arylcarbonylalkyl or phenoxyalkyl, and
$R^9$ represents hydrogen, alkyl, alkenyl, alkoxyalkyl, or alkylthioalkyl, or represents optionally substituted phenyl, phenylalkyl, or phenoxyalkyl,
$R^{10}$ represents hydrogen, alkyl, alkenyl, alkoxyalkyl, or alkylthioalkyl, represents optionally substituted phenyl, phenylalkyl, phenoxyalkyl, or represents the group CO—$R^{11}$, where
$R^{11}$ represents hydrogen, optionally halogen-substituted alkyl, alkenyl, or alkoxy, or represents optionally substituted aryl, arylalkyl, arylalkyloxy or phenoxy, possible substituents being halogen, nitro, cyano, alkyl, alkoxy, halogenoalkyl and halogenoalkoxy.

2. The compound of claim 1 wherein
V represents hydrogen, halogen, $C_1$–$C_6$-alkyl, $C_1$–$C_6$-halogenoalkyl, $C_1$–$C_6$-alkoxy, $C_1$–$C_6$-halogenoalkoxy, phenyl, nitro or cyano,
W represents hydrogen, halogen, $C_1$–$C_6$-alkyl, $C_1$–$C_6$-halogenoalkyl, $C_1$–$C_6$-alkoxy, $C_1$–$C_6$-halogenoalkoxy, nitro or cyano,
X represents hydrogen, halogen, $C_1$–$C_6$-alkyl, $C_1$–$C_6$-halogenoalkyl, $C_1$–$C_6$-alkoxy, $C_2$–$C_6$-alkenyl, $C_2$–$C_6$-alkynyl, $C_1$–$C_6$-alkylthio, $C_1$–$C_6$-alkylsulphinyl, $C_1$–$C_6$-alkylsulphonyl, $C_1$–$C_6$-halogenoalkoxy, nitro, or cyano or represents optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl, phenoxy, phenylthio, benzyloxy or benzylthio,
Y and Z independently of one another each represent hydrogen, halogen, $C_1$–$C_6$-alkyl, $C_1$–$C_6$-halogenoalkyl, $C_1$–$C_6$-alkoxy, $C_2$–$C_6$-alkenyl, $C_2$–$C_6$-alkynyl, $C_1$–$C_6$-alkylthio, $C_1$–$C_6$-alkylsulphinyl, $C_1$–$C_6$-alkylsulphonyl, $C_1$–$C_6$-halogenoalkoxy, nitro, or cyano or represents optionally halogen-, $C_1$–$C_6$-alkyl-, $C_1$–$C_6$-alkoxy-, $C_1$–$C_4$-halogenoalkyl-, $C_1$–$C_6$-halogenoalkoxy-, nitro- or cyano-substituted phenyl, phenyl-$C_1$–$C_4$-alkyl, phenoxy, phenylthio, benzyloxy or benzylthio,
with the proviso that at least one of V, W, X, Y or Z is not hydrogen,
m represents the numbers 1 and 2,

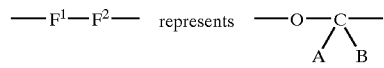

wherein
A represents hydrogen or optionally halogen-substituted $C_1$–$C_{12}$-alkyl, $C_3$–$C_8$-alkenyl, $C_1$–$C_{10}$- alkoxy-$C_1$–$C_8$-alkyl, di-, tri- or tetra-$C_1$–$C_8$-alkoxy-$C_1$–$C_8$-alkyl, $C_1$–$C_{10}$-alkylthio-$C_1$–$C_6$-alkyl, or represents optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted $C_6$- or $C_{10}$-aryl (phenyl or naphthyl), or $C_6$- or $C_{10}$-aryl-$C_1$–$C_6$-alkyl (phenyl-$C_1$–$C_6$-alkyl or naphthyl-$C_1$–$C_6$-alkyl), B represents hydrogen, $C_1$–$C_{12}$-alkyl or $C_1$–$C_8$-alkoxy-$C_1$–$C_6$-alkyl, and G represents hydroxyl (a) or represents one of the groups:

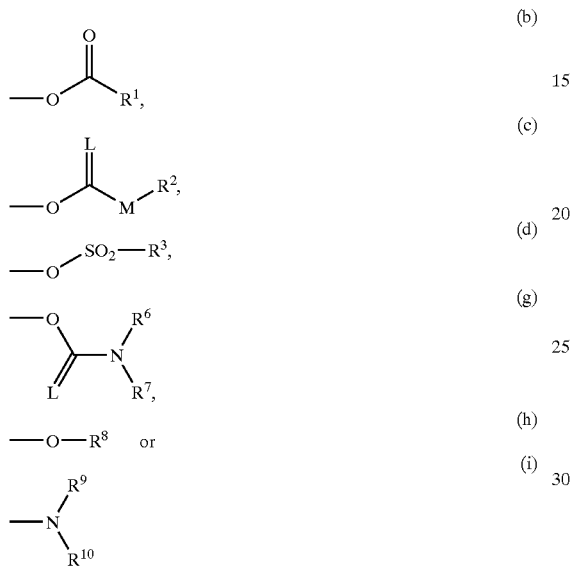

in which

L represents oxygen or sulphur,

M represents oxygen or sulphur, $R^1$ represents optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, or poly-$C_1$–$C_8$-alkoxy-$C_1$–$C_8$-alkyl represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, or represents optionally halogen- or $C_1$–$C_6$-alkyl-substituted phenoxy-$C_1$–$C_6$-alkyl, $R^2$ represents optionally halogen-substituted $C_1$–$C_{20}$-alkyl, $C_2$–$C_{20}$-alkenyl, $C_1$–$C_8$-alkoxy-$C_2$–$C_8$-alkyl, or poly-$C_1$–$C_8$-alkoxy-$C_2$–$C_8$-alkyl, represents optionally halogen-, $C_1$–$C_6$-alkyl- or $C_1$–$C_6$-alkoxy-substituted $C_3$–$C_8$-cycloalkyl, or represents optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl, $R^3$ represents optionally halogen-substituted $C_1$–$C_8$-alkyl or represents optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl, $R^6$ and $R^7$ independently of one another each represent hydrogen, represent optionally halogen-substituted $C_1$–$C_8$-alkyl, $C_3$–$C_8$-cycloalkyl, $C_1$–$C_8$-alkoxy, $C_3$–$C_8$-alkenyl, or $C_1$–$C_8$-alkoxy-$C_1$–$C_8$-alkyl, represent optionally halogen-, $C_1$–$C_8$-halogenoalkyl-, $C_1$–$C_8$-alkyl- or $C_1$–$C_8$-alkoxy-substituted phenyl, or represent optionally halogen-, $C_1$–$C_8$-alkyl-, $C_1$–$C_8$-halogenoalkyl- or $C_1$–$C_8$-alkoxy-substituted benzyl, $R^8$ represents optionally halogen-substituted $C_1$–$C_{10}$-alkyl, $C_3$–$C_8$-alkenyl, $C_3$–$C_8$-alkynyl, $C_1$–$C_8$-alkoxy-$C_1$–$C_4$-alkyl, $C_3$–$C_8$-alkenyloxy-$C_1$–$C_4$-alkyl, $C_3$–$C_8$-alkynyloxy-$C_1$–$C_4$-alkyl, $C_1$–$C_8$-alkylcarbonyl-$C_1$–$C_4$-alkyl, or $C_1$–$C_8$-alkoxycarbonyl-$C_1$–$C_4$-alkyl, represents optionally fluorine-, $C_1$–$C_4$-alkyl- or $C_1$–$C_4$-alkoxy-substituted cycloalkyl or represents optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl-$C_1$–$C_4$-alkyl, phenylcarbonyl-$C_1$–$C_4$-alkyl or phenoxy-$C_1$–$C_4$-alkyl, $R^9$ represents hydrogen, optionally halogen-substituted $C_1$–$C_{10}$-alkyl, $C_3$–$C_{10}$-alkenyl, $C_1$–$C_8$-alkoxy-$C_1$–$C_8$-alkyl, or $C_1$–$C_8$-alkylthio-$C_1$–$C_8$-alkyl, or represents phenyl, phenyl-$C_1$–$C_6$-alkyl or phenoxy-$C_1$–$C_6$-alkyl, each of which is optionally mono- to trisubstituted by identical or different substituents from the group consisting of halogen, $C_1$–$C_6$-alkyl, $C_1$–$C_6$-alkoxy, $C_1$–$C_4$-halogenoalkyl, $C_1$–$C_4$-halogenoalkoxy, cyano and nitro, $R^{10}$ represents hydrogen, $C_1$–$C_{10}$-alkyl, $C_3$–$C_{10}$-alkenyl or represents a group CO—$R^{11}$, and $R^{11}$ represents hydrogen, optionally halogen-substituted $C_1$–$C_{10}$-alkyl, $C_3$–$C_{10}$-alkenyl, or $C_1$–$C_{10}$-alkoxy, or represents optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, phenyl-$C_1$–$C_6$-alkyl, benzyloxy or phenoxy.

3. The compound claim 1 wherein

X represents hydrogen, fluorine, chlorine, bromine, $C_1$–$C_4$-alkyl, $C_1$–$C_4$-alkoxy, $C_1$–$C_4$-halogenoalkyl, $C_1$–$C_4$-halogenoalkoxy, nitro or cyano or represents optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy or benzyloxy, V represents hydrogen, fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, phenyl, nitro or cyano, W represents hydrogen, fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, nitro or cyano, Y and Z independently of one another each represent hydrogen, fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano, or nitro or represent optionally fluorine-, chlorine-, bromine-, $C_1$–$C_4$-alkyl-, $C_1$–$C_2$-halogenoalkyl-, $C_1$–$C_4$-alkoxy-, $C_1$–$C_2$-halogenoalkoxy-, cyano- or nitro-substituted phenyl, phenoxy or benzyloxy, with the proviso that at least one of the V, W, X, Y or Z is not hydrogen, m represents the numbers 1 and 2,

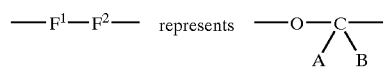

wherein

A represents hydrogen, optionally fluorine- or chlorine-substituted $C_1$–$C_{10}$-alkyl, or $C_1$–$C_8$-alkoxy-$C_1$–$C_6$- alkyl, or represents phenyl or phenyl-$C_1$–$C_2$-alkyl, each of which is optionally mono- to disubstituted by fluorine, chlorine, bromine, $C_1$–$C_4$-alkyl, $C_1$–$C_2$-halogenoalkyl, $C_1$–$C_4$-alkoxy, $C_1$–$C_2$-halogenoalkoxy, cyano or nitro, B represents hydrogen or $C_1$–$C_6$-alkyl, and G represents hydroxyl (a) or represents one of the groups:

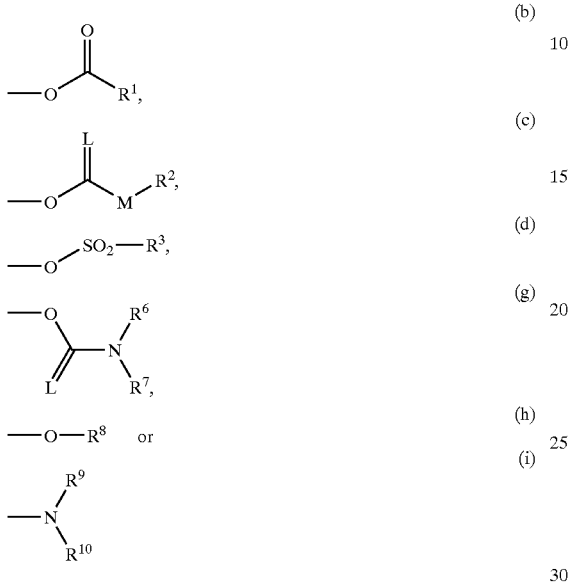

in which

L represents oxygen or sulphur,

M represents oxygen or sulphur, $R^1$ represents $C_1$–$C_{16}$-alkyl, $C_2$–$C_{16}$-alkenyl, $C_1$–$C_6$-alkoxy-$C_1$–$C_6$-alkyl, or $C_1$–$C_6$-alkylthio-$C_1$–$C_4$-alkyl, each of which is optionally mono- to trisubstituted by fluorine or chlorine, represents phenyl which is optionally mono- to disubstituted by fluorine, chlorine, bromine, cyano, nitro, $C_1$–$C_4$-alkyl, $C_1$–$C_4$-alkoxy, $C_1$–$C_2$-halogenoalkyl, $C_1$–$C_2$-halogenoalkoxy, $C_1$–$C_2$-alkylthio or $C_1$–$C_2$-alkylsulphonyl, or represents phenyl-$C_1$–$C_4$-alkyl which is optionally mono- to di-substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, $R^2$ represents $C_1$–$C_{16}$-alkyl, $C_2$–$C_{16}$-alkenyl or $C_1$–$C_6$-alkoxy-$C_2$–$C_6$-alkyl, each of which is optionally mono- to trisubstituted by fluorine, or represents phenyl or benzyl, each of which is optionally mono- to disubstituted by fluorine, chlorine, bromine, cyano, nitro, $C_1$–$C_4$-alkyl, $C_1$–$C_3$-alkoxy, $C_1$–$C_2$-halogenoalkyl or $C_1$–$C_2$-halogenoalkoxy, $R^3$ represents $C_1$–$C_6$-alkyl which is optionally mono- to trisubstituted by fluorine, or represents phenyl which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, $R^6$ represents $C_1$–$C_6$-alkyl, $C_3$–$C_6$-cycloalkyl, $C_1$–$C_6$-alkoxy, $C_3$–$C_6$-alkenyl, or $C_1$–$C_6$-alkoxy-$C_1$–$C_6$-alkyl, represents phenyl which is optionally mono- to disubstituted by fluorine, chlorine, bromine, $C_1$–$C_3$-halogenoalkyl, $C_1$–$C_4$-alkyl or $C_1$–$C_4$-alkoxy, or represents benzyl which is optionally mono- to disubstituted by fluorine, chlorine, bromine, $C_1$–$C_4$-alkyl, $C_1$–$C_3$-halogenoalkyl or $C_1$–$C_4$-alkoxy, $R^7$ represents hydrogen, $C_1$–$C_6$-alkyl or $C_3$–$C_6$-alkenyl, $R^8$ represents $C_1$–$C_6$-alkyl, $C_3$–$C_6$-alkenyl, $C_3$–$C_6$-alkynyl, $C_1$–$C_6$-alkoxy-$C_1$–$C_2$-alkyl, $C_3$–$C_6$-alkenyloxy-$C_1$–$C_2$-alkyl, $C_3$–$C_8$-alkynyloxy-$C_1$–$C_2$-alkyl, $C_1$–$C_6$-alkylcarbonyl-$C_1$–$C_2$-alkyl, or $C_1$–$C_6$-alkoxycarbonyl-$C_1$–$C_2$-alkyl, each of which is optionally mono- to trisubstituted by fluorine or chlorine, or represents phenyl-$C_1$–$C_2$-alkyl, phenylcarbonyl-$C_1$–$C_4$-alkyl or phenoxy-$C_1$–$C_2$-alkyl, each of which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, $R^9$ represents hydrogen, represents $C_1$–$C_6$-alkyl or $C_3$–$C_6$-alkenyl, each of which is optionally mono- to trisubstituted by fluorine or chlorine, represents phenyl-$C_1$–$C_2$-alkyl which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, $R^{10}$ represents hydrogen, $C_1$–$C_6$-alkyl, or $C_3$–$C_6$-alkenyl or represents a group CO—$R^{11}$, $R^{11}$ represents hydrogen, represents $C_1$–$C_6$-alkyl, $C_3$–$C_6$-alkenyl, or $C_1$–$C_6$-alkoxy, each of which is optionally mono- to trisubstituted by fluorine or chlorine, or represents phenyl which is optionally mono- to disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

4. The compound of claim 1 wherein

V represents hydrogen, fluorine, chlorine, bromine, nitro, methyl, phenyl, methoxy or trifluoromethyl, W represents hydrogen, fluorine, chlorine, bromine, methyl, ethyl, trifluoromethyl, methoxy, X represents hydrogen, bromine, fluorine, chlorine, methyl, ethyl, n-propyl, iso-propyl, methoxy, ethoxy, n-propoxy, iso-propoxy, trifluoromethyl, difluoromethoxy, trifluoromethoxy, nitro or cyano, or represents phenyl, phenoxy or benzyloxy, each of which is optionally mono- to disubstituted by fluorine, chlorine, bromine, methyl, tert-butyl, trifluoromethyl, methoxy, trifluoromethoxy, nitro or cyano, Y represents hydrogen, fluorine, chlorine, bromine, methyl, ethyl, i-propyl, tert-butyl, trifluoromethyl, difluoromethyl, methoxy, ethoxy, isopropoxy, trifluoromethoxy, difluoromethoxy, cyano, or nitro or represents phenyl which is optionally mono- to disubstituted by fluorine, chlorine, bromine, methyl, trifluoromethyl, methoxy, trifluoromethoxy, cyano or nitro, Z represents hydrogen, fluorine, chlorine, bromine, methyl, trifluoromethyl, methoxy, trifluoromethoxy, cyano, or nitro or represents phenyl which is optionally mono- to disubstituted by fluorine, chlorine, bromine, methyl, trifluoromethyl, methoxy, trifluoromethoxy, cyano or nitro, with the proviso that at least one of V, W, X, Y or Z is not hydrogen, m represents the number 2,

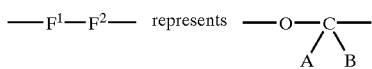

wherein
- A represents hydrogen, optionally fluorine-substituted $C_1$–$C_6$-alkyl, or represents phenyl or benzyl, each of which is optionally mono- to disubstituted by fluorine, chlorine, bromine, methyl, iso-propyl, tert-butyl, methoxy, trifluoromethyl, trifluoromethoxy, cyano or nitro,
- B represents hydrogen or $C_1$–$C_4$-alkyl, and
- G represents hydroxyl (a) or represents one of the groups:

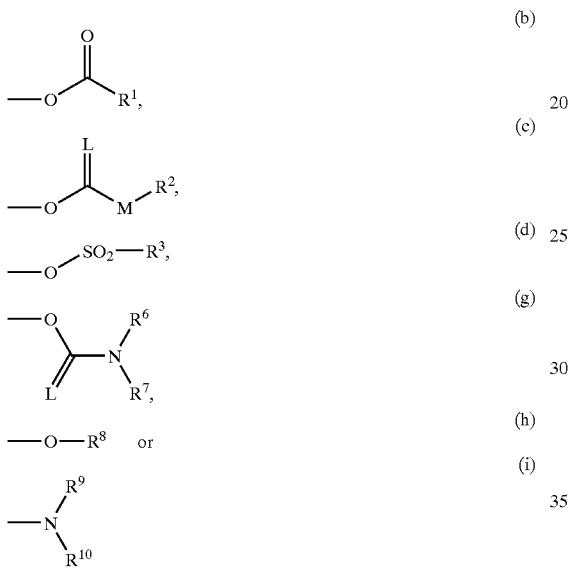

in which
- L represents oxygen or sulphur,
- M represents oxygen or sulphur,
- $R^1$ represents $C_1$–$C_{14}$-alkyl, $C_2$–$C_{14}$-alkenyl, $C_1$–$C_4$-alkoxy-$C_1$–$C_4$-alkyl, or $C_1$–$C_4$-alkylthio-$C_1$–$C_2$-alkyl, each of which is optionally mono- to trisubstituted by fluorine or chlorine, or represents phenyl which is optionally mono- to disubstituted by fluorine, chlorine, bromine, cyano, nitro, methyl, ethyl, i-propyl, methoxy, ethoxy, trifluoromethyl or trifluoromethoxy,
- $R^2$ represents $C_1$–$C_{10}$-alkyl, $C_2$–$C_{10}$-alkenyl or $C_1$–$C_4$-alkoxy-$C_2$–$C_4$-alkyl, each of which is optionally mono- to trisubstituted by fluorine, or represents phenyl or benzyl, each of which is optionally mono- to disubstituted by fluorine, chlorine, cyano, nitro, methyl, ethyl, i-propyl, methoxy, ethoxy, trifluoromethyl or trifluoromethoxy,
- $R^3$ represents methyl, ethyl, n-propyl, or isopropyl, each of which is optionally mono- to trisubstituted by fluorine, or represents phenyl which is optionally monosubstituted by fluorine, chlorine, bromine, methyl, tert-butyl, methoxy, trifluoromethyl, trifluoromethoxy, cyano or nitro,
- $R^6$ represents $C_1$–$C_4$-alkyl, $C_3$–$C_6$-cycloalkyl, $C_1$–$C_4$-alkoxy, $C_3$–$C_4$-alkenyl, or $C_1$–$C_4$-alkoxy-$C_1$–$C_4$-alkyl, represents phenyl which is optionally mono- to disubstituted by fluorine, chlorine, bromine, trifluoromethyl, methyl or methoxy, or represents benzyl which is optionally mono- to disubstituted by fluorine, chlorine, bromine, methyl, trifluoromethyl or methoxy,
- $R^7$ represents hydrogen, $C_1$–$C_4$-alkyl or $C_3$–$C_4$-alkenyl, or
- $R^8$ represents $C_1$–$C_4$-alkyl, $C_3$–$C_4$-alkenyl, $C_1$–$C_4$-alkoxy-methyl, $C_3$–$C_4$-alkenyloxy-methyl, $C_3$–$C_4$-alkynyloxy-methyl, $C_1$–$C_4$-alkylcarbonyl-methyl, or $C_1$–$C_4$-alkoxycarbonyl-methyl, each of which is optionally mono- to trisubstituted by fluorine or chlorine, or represents benzyl, phenylcarbonyl-methyl or phenoxy-methyl, each of which is optionally mono- to disubstituted by fluorine, chlorine, bromine, methyl, methoxy, trifluoromethyl, trifluoromethoxy, cyano or nitro,
- $R^9$ represents hydrogen, represents $C_1$–$C_4$-alkyl, or allyl, each of which is optionally mono- to trisubstituted by fluorine or chlorine, or represents benzyl which is optionally mono- to disubstituted by fluorine, chlorine, bromine, methyl, ethyl, iso-propyl, tert-butyl, methoxy, iso-propoxy, trifluoromethyl, trifluoromethoxy, cyano or nitro,
- $R^{10}$ represents hydrogen, $C_1$–$C_4$-alkyl, or allyl or represents a group CO—$R^{11}$, and
- $R^{11}$ represents hydrogen, represents $C_1$–$C_4$-alkyl, $C_3$–$C_4$-alkenyl, or $C_1$–$C_4$-alkoxy, each of which is optionally mono- to trisubstituted by fluorine or chlorine, or represents phenyl which is optionally mono- to disubstituted by fluorine, chlorine, bromine, methyl, methoxy, trifluoromethyl, trifluoromethoxy, cyano or nitro.

5. A crop protection agent selected from the group consisting of pesticides, herbicides and fungicides comprising one or more compounds of formula (I) of claim 1 and a member selected from the group consisting of extenders, surfactants and mixtures thereof.

* * * * *